(12) United States Patent
Fathallah et al.

(10) Patent No.: US 12,016,836 B2
(45) Date of Patent: *Jun. 25, 2024

(54) COMPOSITIONS AND METHODS FOR REDUCING IMMUNE INTOLERANCE AND TREATING AUTOIMMUNE DISORDERS

(71) Applicant: Lapix Therapeutics, Inc., Boston, MA (US)

(72) Inventors: Anas M. Fathallah, Wakefield, MA (US); Scott D. Larsen, Gobles, MI (US); Abdulraouf Ramadan, Malden, MA (US)

(73) Assignee: Lapix Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,128

(22) Filed: Feb. 13, 2023

(65) Prior Publication Data

US 2023/0263760 A1 Aug. 24, 2023

Related U.S. Application Data

(63) Continuation of application No. 17/886,926, filed on Aug. 12, 2022, now Pat. No. 11,648,225.

(60) Provisional application No. 63/233,039, filed on Aug. 13, 2021.

(51) Int. Cl.
| | | |
|---|---|---|
| A61K 31/198 | (2006.01) | |
| A61K 9/00 | (2006.01) | |
| A61K 9/08 | (2006.01) | |
| A61K 31/357 | (2006.01) | |
| A61K 31/4184 | (2006.01) | |
| A61K 31/44 | (2006.01) | |
| A61K 31/472 | (2006.01) | |
| A61K 47/40 | (2006.01) | |
| A61P 25/28 | (2006.01) | |
| A61P 37/06 | (2006.01) | |
| C07C 235/34 | (2006.01) | |
| C07D 213/65 | (2006.01) | |
| C07D 217/02 | (2006.01) | |
| C07D 235/06 | (2006.01) | |
| C07D 319/18 | (2006.01) | |

(52) U.S. Cl.
CPC .......... *A61K 31/198* (2013.01); *A61K 9/0053* (2013.01); *A61K 9/08* (2013.01); *A61K 31/357* (2013.01); *A61K 31/4184* (2013.01); *A61K 31/44* (2013.01); *A61K 31/472* (2013.01); *A61K 47/40* (2013.01); *A61P 25/28* (2018.01); *A61P 37/06* (2018.01); *C07C 235/34* (2013.01); *C07D 213/65* (2013.01); *C07D 217/02* (2013.01); *C07D 235/06* (2013.01); *C07D 319/18* (2013.01)

(58) Field of Classification Search
CPC ............................. C07D 213/65; A61K 31/198
See application file for complete search history.

(56) References Cited

U.S. PATENT DOCUMENTS

| | | |
|---|---|---|
| 6,004,955 A | 12/1999 | Jin et al. |
| 11,648,225 B2 | 5/2023 | Fathallah et al. |
| 2007/0099982 A1 | 5/2007 | Salama |
| 2016/0243220 A1 | 8/2016 | Balu-Iyer et al. |
| 2019/0151426 A1 | 5/2019 | Balu-Iyer et al. |
| 2023/0089267 A1 | 3/2023 | Fathallah et al. |

FOREIGN PATENT DOCUMENTS

| | | |
|---|---|---|
| WO | 96/38426 A1 | 12/1996 |
| WO | 2018009507 A1 | 1/2018 |
| WO | 2019046321 A1 | 3/2019 |
| WO | 2022192899 A9 | 9/2022 |
| WO | 2023/019242 A1 | 2/2023 |
| WO | 2023/019244 A1 | 2/2023 |

OTHER PUBLICATIONS

International Search Report and Written Opinion received for PCT Patent Application No. PCT/US2022/071082, dated Jun. 28, 2022, 10 pages.

Albacker LA, Karisola P, Chang YJ, et al. TIM-4, a receptor for phosphatidylserine, controls adaptive immunity by regulating the removal of antigen-specific T cells. J Immunol. 2010; 185(11):6839-6849. doi:10.4049/jimmunol.1001360.

Freeman GJ, Casasnovas JM, Umetsu DT, DeKruyff RH. Tim genes: a family of cell surface phosphatidylserine receptors that regulate innate and adaptive immunity. Immunol Rev. 2010;235(1):172-189.

Glassman Fiona Y. et al: "Subcutaneous administration of Lyso-phosphatidylserine nanoparticles induces immunological tolerance towards Factor VIII in a Hemophilia A mouse model", International Journal of Pharmaceutics, vol. 548, No. 1, Sep. 1, 2018.

(Continued)

*Primary Examiner* — Golam M Shameem
(74) *Attorney, Agent, or Firm* — McNeill Baur PLLC

(57) ABSTRACT

Provided herein are compounds and their pharmaceutically acceptable salts, lipid particles comprising such compounds or pharmaceutically acceptable salts thereof and compositions of the foregoing that can be used to reduce immune intolerance in a subject, for example, to treat autoimmune disorders, or in combination with an antigenic therapy, such as a protein or gene therapy, to improve the efficacy of the antigenic therapy. The compounds have the following structural formula:

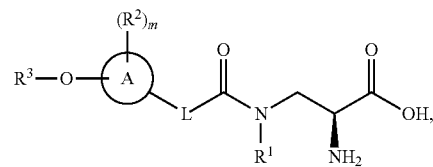

wherein values for the variables (e.g., Ring A, L, $R^1$, $R^2$, $R^3$, m) are as described herein.

21 Claims, 26 Drawing Sheets

(56) References Cited

OTHER PUBLICATIONS

Kelleher RJ Jr, Balu-Iyer S, Loyall J, et al. Extracellular Vesicles Present in Human Ovarian Tumor Microenvironments Induce a Phosphatidylserine-Dependent Arrest in the T-cell Signaling Cascade. Cancer Immunol Res. 2015;3(11):1269-1278. doi:10.1158/2326-6066.CIR-15-0086.

Kent, S. J., Karlik, S. J., Cannon, C., Hines, D. K., Yednock, T. A., Fritz, L. C., & Horner, H. C. (1995). A monoclonal antibody to α4 integrin suppresses and reverses active experimental allergic encephalomyelitis. Journal of neuroimmunology, 58(1), 1-10.

Ramadan A, Lucca LE, Carrie N, Desbois S, Axisa PP, Hayder M, Bauer J, Liblau RS, Mars LT. In situ expansion of T cells that recognize distinct self-antigens sustains autoimmunity in the CNS. Brain. May 2016;139(Pt 5):1433-46. doi: 10.1093/brain/aww032. Epub Mar. 21, 2016. PMID: 27000832.

Sabatos-Peyton, C. A. et al. Blockade of Tim-3 binding to phosphatidylserine and CEACAM1 is a shared feature of anti-Tim-3 antibodies that have functional efficacy. Oncoimmunology 7, e1385690 (2018).

Santiago C, Ballesteros A, Martínez-Muñoz L, et al. Structures of T cell immunoglobulin mucin protein 4 show a metal-Ion-dependent ligand binding site where phosphatidylserine binds. Immunity. 2007;27(6):941-951. doi:10.1016/j.immuni.2007.11.008.

Serre L, Girard M, Ramadan A, Menut P, Rouquié N, Lucca LE, Mahiddine K, Leobon B, Mars LT, Guerder S. Thymic-Specific Serine Protease Limits Central Tolerance and Exacerbates Experimental Autoimmune Encephalomyelitis. J Immunol. Dec. 1, 2017;199(11):3748-3756. doi: 10.4049/jimmunol.1700667. Epub Oct. 2, 20173. PMID: 29061767.

Wolf, Y., Anderson, A.C. & Kuchroo, V.K. TIM3 comes of age as an inhibitory receptor. Nat Rev Immunol 20, 173-185 (2020). https://doi.org/10.1038/s41577-019-0224-6.

Notification of Transmittal of the International Search Report and the Written Opinion of the International Searching Authority, or the Declarations for International Application No. PCT/US2022/074908, "Compositions and Methods For Reducing Immune Intolerance and Treating Autoimmune Disorders", dated Oct. 19, 2022.

Urwyler, S., et al., "Drug Design, in Vitro Pharmacology, and Structure-Activity Relationships of 3-Acylamino-2- aminopropionic Acid Derivatives, a Novel Class of Partial Agonists at the Glycine Site on the N-Methyl-D-aspartate (NMDA) Receptor Complex", Journal of Medicinal Chemistry, vol. 52, No. 16, Aug. 27, 2009.

Notice of Allowance for U.S. Appl. No. 17/886,926, "Compositions and Methods for Reducing Immune Intolerance and Treating Autoimmune Disorders" dated: Jan. 9, 2023.

International Search Report and Written Opinion issued in International Application No. PCT/US2022/070407, dated May 18, 2022, 16 pages.

Serrano et al., "Parallel synthesis and yeast growth inhibition screening of succinamic acid libraries," Journal of Combinatorial Chemistry 9(4):635-643 (2007).

COMPOSITIONS AND METHODS FOR REDUCING IMMUNE INTOLERANCE AND TREATING AUTOIMMUNE DISORDERS

RELATED APPLICATIONS

This application is a continuation of U.S. application Ser. No. 17/886,926, filed on Aug. 12, 2022, which claims the benefit of U.S. Provisional Application No. 63/233,039, filed on Aug. 13, 2021. The entire teachings of the above applications are incorporated herein by reference.

BACKGROUND

Enzyme and protein replacement therapy is a successful therapeutic strategy for treating congenital disorders where an endogenous protein is mutated, missing, or otherwise aberrant. However, clinical administration of foreign enzyme or protein is associated with the development of unwanted immune response toward the enzyme or protein. The unwanted immune response could lead to neutralization of the enzyme/protein, or alteration of its pharmacokinetics. In many circumstances, patients do not have alternative therapeutic options, making the unwanted immune response to therapy a major issue facing enzyme and protein replacement therapy recipients.

Similarly, gene therapy offers a promising approach to treat a number of congenital disorders and other diseases. Immunogenicity of the carrier and/or the genetic material carried within is a major challenge to the clinical application of gene therapy. Existing anti-carrier antibodies is a counter-indication to treatment with some approved gene therapies. Furthermore, nascent anti-carrier antibodies can prevent repeat dosing in subjects that receive the first dose of a gene therapy.

Autoimmune disorders are a collection of disorders in which the body lacks or loses tolerance to self-antigens. This results in the body's immune system attacking healthy cells, and can have debilitating and devastating effects. Current approaches to treating autoimmune disorders rely on general immune suppression at the humoral, cellular and/or complement level, rendering patients immunocompromised and susceptible to opportunistic infections.

Accordingly, there is a need for compositions that can reduce immune intolerance to exogenous antigens (e.g., enzyme replacement therapy, gene therapy) or endogenous antigens (e.g., self-antigens causing autoimmune disorders), for example, by mitigating the immunogenicity of enzyme and protein replacement therapy and/or gene therapy, or increasing self-tolerance to self-antigens.

SUMMARY

The technology described herein relates to tolerance induction for exogenous antigens (e.g., antigen-specific and/or antigen-exclusive tolerance induction), or for self-antigens. The technology is based on engaging and modulating (e.g., activating) the T-cell immunoglobulin mucin protein (TIM) family of receptors.

Provided herein is a compound of the following structural formula:

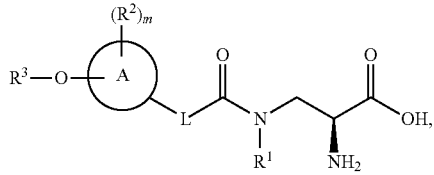

or a pharmaceutically acceptable salt thereof, wherein values for the variables (e.g., Ring A, L, $R^1$, $R^2$, $R^3$, m) are as described herein.

Also provided herein is a lipid particle comprising one or more lipids, or a pharmaceutically acceptable salt thereof, and a compound of the disclosure.

Also provided herein is a composition (e.g., pharmaceutical composition) comprising a compound of the disclosure.

Also provided herein is a composition (e.g., pharmaceutical composition) comprising a plurality of lipid particles described herein.

Also provided herein are methods of immunotolerizing a subject in need thereof. The methods comprise administering to the subject a therapeutically effective amount of a composition described herein.

Also provided herein are methods of immunotolerizing a subject in need thereof to an antigen and inhibiting or reducing an antigen-specific antibody titer in a subject. The methods comprise administering to the subject the antigen and a therapeutically effective amount of a composition described herein, or administering to the subject a composition described herein comprising the antigen, or an immunogenic fragment of the antigen.

Also provided herein are methods of inducing a population of regulatory T-cells in a subject (e.g., in response to an antigen) and increasing the activity or level of tolerogenic T-cells in a subject. The methods comprise administering to the subject a therapeutically effective amount of a composition described herein (e.g., a composition described herein comprising the antigen, or an immunogenic fragment of the antigen).

Also provided herein are methods of inducing a population of regulatory B-cells in a subject (e.g., in response to an antigen). The methods comprise administering to the subject a therapeutically effective amount of a composition described herein (e.g., a composition described herein comprising the antigen, or an immunogenic fragment of the antigen).

Also provided herein is a method of treating an autoimmune disorder in a subject in need thereof, comprising administering to the subject a therapeutically effective amount of a composition described herein (e.g., a composition described herein comprising self-antigen associated with the autoimmune disorder).

Also provided herein is a method of treating a disease, disorder or condition in a subject in need thereof with an antigenic therapy, comprising administering to the subject the antigenic therapy (e.g., a therapeutically effective amount of the antigenic therapy) and a composition described herein in an amount sufficient to immunotolerize the subject to the antigenic therapy, or a therapeutically effective amount of a composition described herein comprising the antigenic therapy.

Also provided herein is a compound of the disclosure or composition (e.g., pharmaceutical composition) for a use described herein (e.g., treatment of an autoimmune disorder; treatment of a disease, disorder or condition treatable with antigenic therapy), wherein the composition is a composition described herein. Also provided herein is use of a compound of the disclosure or composition described herein for the manufacture of a medicament for a use described herein (e.g., treatment of an autoimmune disorder; treatment of a disease, disorder or condition treatable with antigenic therapy).

BRIEF DESCRIPTION OF THE DRAWINGS

The foregoing will be apparent from the following more particular description of example embodiments.

DETAILED DESCRIPTION

Figure 1:
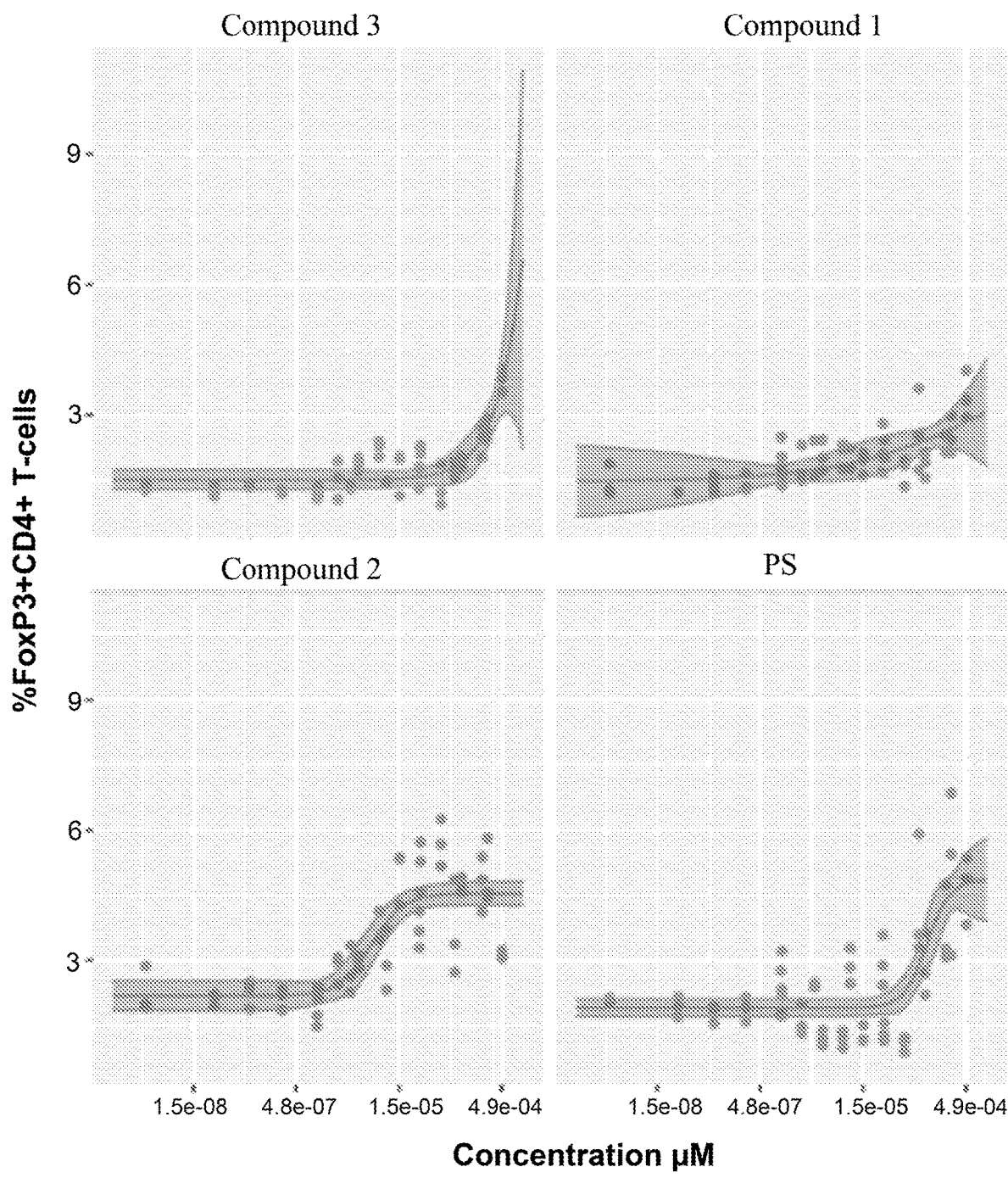
FIG. 1 shows changes in percent FoxP3+/CD4+ T-cells by treatment described in Example 2.

A description of example embodiments follows.
Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5$^{th}$ Ed.: Smith, M. B. and March, J., John Wiley & Sons, New York: 2001, the relevant contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

When introducing elements disclosed herein, the articles "a," "an," "the," and "said" are intended to mean that there are one or more of the elements. Further, the one or more elements may be the same or different.

"About" means within an acceptable error range for the particular value, as determined by one of ordinary skill in the art. Typically, an acceptable error range for a particular value depends, at least in part, on how the value is measured or determined, e.g., the limitations of the measurement system. For example, "about" can mean within an acceptable standard deviation, per the practice in the art. Alternatively, "about" can mean a range of ±20%, e.g., ±10%, ±5% or ±1% of a given value. It is to be understood that the term "about"

can precede any particular value specified herein, except for particular values used in the Exemplification.

"Alkyl" refers to a branched or straight-chain, monovalent, hydrocarbon radical having the specified number of carbon atoms. Thus, "$(C_1-C_8)$alkyl" refers to a radical having from 1-8 carbon atoms in a branched or linear arrangement. In some aspects, alkyl is $(C_1-C_{30})$alkyl, e.g., $(C_5-C_{30})$alkyl, $(C_1-C_{25})$alkyl, $(C_5-C_{25})$alkyl, $(C_1-C_{15})$alkyl, $(C_1-C_6)$alkyl, or $(C_1-C_5)$alkyl. Examples of alkyl groups include methyl, ethyl, n-propyl, isopropyl, n-butyl, isobutyl, sec-butyl, t-butyl, n-pentyl, isopentyl, neopentyl, 2-methylpentyl, n-hexyl, and the like. In some aspects, alkyl is optionally substituted, e.g., with one or more substituents described herein.

"Aryl" refers to a monocyclic or polycyclic (e.g., bicyclic, tricyclic), aromatic, hydrocarbon ring system having the specified number of ring atoms. Thus, "$(C_6-C_{15})$aryl" refers to a ring system having from 6-15 ring atoms. Examples of aryl include phenyl, naphthyl and fluorenyl. In some aspects, aryl is optionally substituted, e.g., with one or more substituents described herein.

"Heteroaryl" refers to a monocyclic or polycyclic (e.g., bicyclic, tricyclic), aromatic, hydrocarbon ring system having the specified number of ring atoms, wherein at least one carbon atom in the ring system has been replaced with a heteroatom selected from nitrogen, sulfur and oxygen. Thus, "$(C_5-C_{15})$heteroaryl" refers to a heteroaromatic ring system having from 5-15 ring atoms consisting of carbon, nitrogen, sulfur and oxygen. A heteroaryl can contain 1, 2, 3 or 4 (e.g., 1, 2 or 3) heteroatoms independently selected from nitrogen, sulfur and oxygen. Typically, heteroaryl is $(C_5-C_{20})$heteroaryl, e.g., $(C_5-C_{15})$heteroaryl, $(C_5-C_{12})$heteroaryl, $C_5$ heteroaryl or $C_6$ heteroaryl. Monocyclic heteroaryls include, but are not limited to, furan, oxazole, thiophene, triazole, triazene, thiadiazole, oxadiazole, imidazole, isothiazole, isoxazole, pyrazole, pyridazine, pyridine, pyrazine, pyrimidine, pyrrole, tetrazole and thiazole. Bicyclic heteroaryls include, but are not limited to, indolizine, indole, isoindole, indazole, benzimidazole, benzofuran, benzothiazole, purine, quinoline, isoquinoline, cinnoline, phthalazine, quinazoline, quinoxaline, naphthyridine and pteridine. In some aspects, heteroaryl is optionally substituted, e.g., with one or more substituents described herein.

"Alkoxy" refers to an alkyl radical attached through an oxygen linking atom, wherein alkyl is as described herein. Examples of alkoxy include, but are not limited to, methoxy, ethoxy, propoxy, isopropoxy, and the like.

"Halogen" and "halo" are used interchangeably herein and each refers to fluorine, chlorine, bromine, or iodine. In some aspects, halo is fluoro, chloro or bromo. In some aspects, halo is fluoro or chloro. In some aspects, halo is fluoro.

"Haloalkyl" includes mono, poly, and perhaloalkyl groups, wherein each halogen is independently selected from fluorine, chlorine, bromine and iodine (e.g., fluorine, chlorine and bromine), and alkyl is as described herein. In one aspect, haloalkyl is perhaloalkyl (e.g., perfluoroalkyl). Examples of haloalkyl include, but are not limited to, trifluoromethyl and pentafluoroethyl.

"Haloalkoxy" refers to a haloalkyl radical attached through an oxygen linking atom, wherein haloalkyl is as described herein. Examples of haloalkoxy include, but are not limited to, trifluoromethoxy.

The term "substituted" refers to replacement of a hydrogen atom with a suitable substituent. Typically, the suitable substituent replaces a hydrogen atom bound to a carbon atom, but a substituent may also replace a hydrogen bound to a heteroatom, such as a nitrogen, oxygen or sulfur atom. It will be understood that "substitution" or "substituted with" includes the implicit proviso that such substitution is in accordance with permitted valence of the substituted atom. It is also preferred that the substituent, and the substitution, result in a stable compound, e.g., which does not spontaneously undergo transformation such as by rearrangement, cyclization, elimination, etc. Suitable substituents for use herein include acyclic and cyclic, branched and unbranched, carbocyclic and heterocyclic, aromatic and non-aromatic substituents of organic compounds. For example, suitable substituents can include halogen, hydroxyl, carbonyl (such as carboxyl, alkoxycarbonyl, formyl, or acyl), thiocarbonyl (such as thioester, thioacetate, or thioformate), alkyl, alkoxy, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, cycloalkyl, heterocyclyl, aralkyl, aryl or heteroaryl. It will be understood by those skilled in the art that substituents can themselves be substituted, if appropriate. Accordingly, substituents can further include an acetamide, for example.

The permissible substituents can be one or more and the same or different for appropriate organic compounds. Thus, an "optionally substituted" group is, in some aspects, substituted with 0-5 (e.g., 0-3, 0, 1, 2, 3, 4, 5) substituents independently selected from halo, $(C_1-C_6)$alkoxy, $(C_1-C_6)$haloalkoxy, $(C_1-C_6)$alkyl or $(C_1-C_6)$haloalkyl, or optionally substituted $(C_6-C_{15})$aryl or $(C_5-C_{15})$heteroaryl. In some aspects, an optionally substituted aryl or heteroaryl is substituted with 0-5 (e.g., 0-3, 0, 1, 2, 3, 4, 5) substituents independently selected from halo, $(C_1-C_6)$alkoxy, $(C_1-C_6)$haloalkoxy, $(C_1-C_6)$alkyl or $(C_1-C_6)$haloalkyl (e.g., halo, $(C_1-C_5)$alkoxy, $(C_1-C_5)$haloalkoxy, $(C_1-C_5)$alkyl or $(C_1-C_5)$haloalkyl). In some aspects, an "optionally substituted" aryl or heteroaryl is substituted with 0-5 (e.g., 0-3, 0, 1, 2, 3, 4, 5) substituents independently selected from halo, $(C_1-C_3)$alkoxy, $(C_1-C_3)$haloalkoxy, $(C_1-C_3)$alkyl or $(C_1-C_3)$haloalkyl. In some aspects, an optionally substituted (e.g., substituted) alkyl is substituted with 0-5 (e.g., 0-3, 1 or 2, 0, 1, 2, 3, 4, 5) substituents independently selected from halo (e.g., fluoro), $(C_1-C_6)$alkoxy, $(C_1-C_6)$haloalkoxy (e.g., $(C_1-C_6)$ fluoroalkoxy), $(C_6-C_{15})$aryl or $(C_5-C_{15})$heteroaryl.

The term "optionally substituted", as used herein or denoted by a variable followed by a subscript numeral that includes the value 0, as in —$(R^{30})_p$ (wherein $R^{30}$ and p are as described herein), means that substitution is optional and, therefore, it is possible for the atom or moiety designated as "optionally substituted" to be unsubstituted or substituted. In some aspects, an optionally substituted group is unsubstituted. When an optionally substituted group denoted herein by a variable followed by a subscript numeral that includes the value 0 is unsubstituted, the subscript numeral following the variable is 0. In some aspects, an optionally substituted group is substituted. When an optionally substituted group denoted herein by a variable followed by a subscript numeral that includes the value 0 is substituted, the subscript numeral following the variable is other than 0. Unless otherwise indicated, e.g., as with the terms "substituted" or "optionally substituted," a group designated herein is unsubstituted.

As used herein, the term "compound of the disclosure" refers to a compound of any of the structural formulas depicted herein (e.g., a compound of Structural Formula I, an exemplified compound), as well as isomers, such as stereoisomers (including diastereoisomers, enantiomers and racemates) and tautomers thereof, isotopically labeled variants thereof (including those with deuterium substitutions), prodrugs (e.g., alkyl ester prodrugs), and inherently formed moieties (e.g., polymorphs and/or solvates, such as hydrates) thereof. When a moiety is present that is capable of forming a salt, then salts are included as well, in particular, pharmaceutically acceptable salts thereof.

Compounds of the disclosure may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemic mixtures, individual isomers (e.g., diastereomers, enantiomers, geometrical isomers (including cis and trans double bond isomers), conformational isomers (including rotamers and atropisomers), tautomers) and intermediate mixtures, with all possible isomers and mixtures thereof being included, unless otherwise indicated.

When a disclosed compound is depicted by structure without indicating the stereochemistry, and the compound has one or more chiral centers, it is to be understood that the structure encompasses one enantiomer or diastereomer of the compound separated or substantially separated from the corresponding optical isomer(s), a racemic mixture of the compound and mixtures enriched in one enantiomer or diastereomer relative to its corresponding optical isomer(s). When a disclosed compound is depicted by a structure indicating stereochemistry, and the compound has one or more chiral centers, the stereochemistry indicates absolute configuration of the substituents around the one or more chiral centers. "R" and "S" can also or alternatively be used to indicate the absolute configuration of substituents around one or more chiral carbon atoms. D- and L- can also or alternatively be used to designate stereochemistry.

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms.

"Racemate" or "racemic mixture," as used herein, refer to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left|\frac{R-S}{R+S}\right| \times 100\%,$$

where R and S represent the respective fractions of each enantiomer in a mixture, such that R+S=1. An enantiomer may be present in an ee of at least or about 50%, about 60%, about 70%, about 80%, about 90%, about 95%, about 98%, about 99% or about 99.9%.

Percent diastereomeric excess (de) is defined as the absolute difference between the mole fraction of each diastereomer multiplied by 100% and can be represented by the following equation:

$$de = \left|\frac{D1 - (D2+D3+D4...)}{D1 + (D2+D3+D4...)}\right| \times 100\%,$$

where D1 and (D2+D3+D4 . . . ) represent the respective fractions of each diastereomer in a mixture, such that D1+(D2+D3+D4 . . . )=1. A diastereomer may be present in a de of at least or about 50%, about 60%, about 70%, about 80%, about 90%, about 95%, about 98%, about 99% or about 99.9%.

Unless otherwise stated, compounds of the disclosure include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention. In all provided structures, any hydrogen atom can also be independently selected from deuterium (2H), tritium (3H) and/or fluorine ($^{18}$F). Such compounds are useful, for example, as analytical tools, as probes in biological assays, or as therapeutic agents in accordance with the present invention.

The phrase "pharmaceutically acceptable" means that the substance or composition the phrase modifies is, within the scope of sound medical judgment, suitable for use in contact with the tissues of humans and lower animals without undue toxicity, irritation, allergic response and the like, and are commensurate with a reasonable benefit/risk ratio.

As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids, and suitable inorganic and organic bases.

Examples of salts derived from suitable acids include salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art, such as ion exchange. Other pharmaceutically acceptable salts derived from suitable acids include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like.

Either the mono-, di- or tri-acid salts can be formed, and such salts can exist in either a hydrated, solvated or substantially anhydrous form.

Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine and picoline, or $N^+((C_1-C_4)alkyl)_4$ salts. Representative alkali or alkaline earth metal salts include sodium, lithium, potassium, calcium, magnesium, barium and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Compounds described herein can be provided in prodrug form, e.g., as ester prodrugs. As used herein, the term "prodrug" refers to a compound that can be hydrolyzed, oxidized, metabolized and/or otherwise react under biological conditions (e.g., in vivo) to provide a compound of Structural Formula I, or a salt thereof (e.g., pharmaceutically acceptable salt thereof). Prodrugs may become active upon reaction under biological conditions (e.g., and be biologically inactive), or they may have activity in their unreacted forms. A prodrug may undergo reduced metabolism under physiological conditions (e.g., due to the presence of a hydrolyzable group), thereby resulting in improved circulating half-life of the prodrug (e.g., in the blood). Thus, in some aspects, a prodrug includes a hydrolyzable group, as in an ester prodrug, e.g., an alkyl ester prodrug. Prodrugs can typically be prepared using well-known methods, such as those described by Burger's Medicinal Chemistry and Drug Discovery (1995) 172-178, 949-982 (Manfred E. Wolff ed., 5$^{th}$ ed).

As used herein, the term "hydrolyzable group" refers to a moiety that, when present in a prodrug, yields a carboxylic acid or salt thereof upon hydrolysis. Hydrolysis can occur, for example, spontaneously under acidic or basic conditions in a physiological environment (e.g., blood, metabolically active tissues such as, for example, liver, kidney, lung, brain), or can be catalyzed by an enzyme(s), (e.g., esterase, peptidases, hydrolases, oxidases, dehydrogenases, lyases or ligases). A hydrolyzable group can confer upon a prodrug advantageous properties in vivo, such as improved water solubility, improved circulating half-life in the blood, improved uptake, improved duration of action, or improved onset of action.

Examples of hydrolyzable groups include $(C_1-C_{10})$alkyl, $(C_2-C_{10})$alkenyl, $(C_2-C_{10})$alkynyl, $(C_1-C_{10})$alkoxy$(C_1-C_{10})$alkyl or $(C_1-C_{10})$alkoxy$(C_1-C_{10})$alkoxy$(C_1-C_{10})$alkyl, each optionally substituted with one or more independently selected halo (e.g., fluoro). For example, a hydrolyzable group may be $(C_1-C_{10})$alkyl, such as methyl, ethyl, n-propyl, isopropyl, n-butyl, sec-butyl, isobutyl, tert-butyl, pentyl, hexyl or heptyl, allyl, ethoxymethyl, methoxyethyl, methoxyethoxymethyl or methoxyethoxyethyl. It will be appreciated that when a compound of Structural Formula I is provided in ester prodrug form, the hydrogen of the carboxylic acid of the compound of Structural Formula I is replaced with a hydrolyzable group, such a hydrolyzable group described herein (e.g., a $(C_1-C_{10})$alkyl optionally substituted with one or more independently selected halo (e.g., fluoro)).

Compounds described herein can also exist as "solvates" or "hydrates." A "hydrate" is a compound that exists in a composition with one or more water molecules. A hydrate can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared. The source of such solvate or hydrate can be from the solvent of crystallization, inherent in the solvent of preparation or crystallization, or adventitious to such solvent.

"Pharmaceutically acceptable carrier" refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Antigen," as used herein, refers to any substance that can be recognized by the immune system. "Antigen" broadly encompasses proteins, such as enzymes, peptides, such as polypeptides, carbohydrates, such as polysaccharides, haptens, nucleic acids and grafts. An antigen can be a self-antigen, an antigen produced, under normal conditions or as part of a disorder, by the body, or a foreign antigen, a non-self-antigen. Examples of self-antigens include self-antigens associated with autoimmune disorders, including any of the self-antigens described herein. Examples of foreign antigens include antigenic therapies (e.g., therapeutic proteins, gene therapies, cellular therapies), allergens and alloantigens.

"Treating," as used herein, refers to taking steps to deliver a therapy to a subject, such as a mammal, in need thereof (e.g., as by administering to a mammal one or more therapeutic agents). "Treating" includes inhibiting the disease or condition (e.g., as by slowing or stopping its progression or causing regression of the disease or condition), and relieving the symptoms resulting from the disease or condition.

"A therapeutically effective amount" is an amount effective, at dosages and for periods of time necessary, to achieve a desired therapeutic result (e.g., induction of immune tolerance, reduction of immune intolerance, treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual.

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some aspects, a subject is a human.

Compounds

A first embodiment is a compound of the following structural formula:

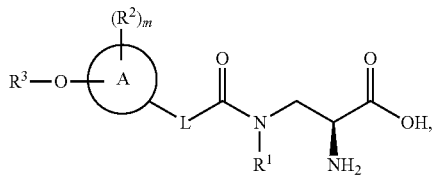

(I)

or a prodrug thereof, or a pharmaceutically acceptable salt of the foregoing, wherein:

Ring A is phenyl or $(C_5-C_6)$heteroaryl;
L is $—(CH_2)_n—$, $—C(O)—$ or $—C(OH)_2—$;
$R^1$ is H or $(C_1-C_5)$alkyl;
each $R^2$ is independently chloro or fluoro;
$R^3$ is $(C_1-C_3)$alkyl substituted with one or more independently selected $(C_6-C_{15})$aryl or $(C_5-C_{15})$heteroaryl, wherein the $(C_6-C_{15})$aryl and $(C_5-C_{15})$heteroaryl are each independently substituted with $—(R^{30})_p$;
each $R^{30}$ is independently halo, $(C_1-C_5)$alkoxy, $(C_1-C_5)$ haloalkoxy, $(C_1-C_5)$alkyl or $(C_1-C_5)$haloalkyl, or two $R^{30}$ attached to adjacent ring atoms, taken together, form $—(CH_2)_q—$ or $—O(CH_2)_rO—$;
n is 1, 2 or 3;
m is 0, 1, 2, 3 or 4;
each p is independently 0, 1, 2, 3, 4, 5, 6, 7, 8, 9 or 10;
each q is independently 3, 4, 5 or 6; and
each r is independently 1, 2, 3 or 4.

In a first aspect of the first embodiment, Ring A is phenyl or pyridinyl. Values for the remaining variables are as described in the first embodiment.

In a second aspect of the first embodiment, Ring A is phenyl. Values for the remaining variables are as described in the first embodiment, or first aspect thereof.

In a third aspect of the first embodiment, $R^1$ is H. Values for the remaining variables are as described in the first embodiments, or first or second aspect thereof.

In a fourth aspect of the first embodiment, $R^3$ is methyl substituted with one, two or three independently selected $(C_6-C_{15})$aryl or $(C_5-C_{15})$heteroaryl, each independently substituted with $—(R^{30})_p$. Values for the remaining variables, including $R^{30}$ and p, are as described in the first embodiment, or first through third aspects thereof.

In a fifth aspect of the first embodiment, $R^3$ is $(C_1-C_3)$ alkyl (and, in some preferred aspects, methyl) substituted with one or more (e.g., one, two or three) independently selected $(C_6-C_{15})$aryl or $(C_5-C_{15})$heteroaryl independently selected from phenyl, naphthyl, pyridinyl, quinolinyl, isoquinolinyl or benzo[d]imidazolyl, each independently substituted with $—(R^{30})_p$. Values for the remaining variables, including $R^{30}$ and p, are as described in the first embodiment, or first through fourth aspects thereof.

In a sixth aspect of the first embodiment, $R^3$ is $(C_1-C_3)$ alkyl (and, in some preferred aspects, methyl) substituted with one or two independently selected $(C_6-C_{15})$aryl or $(C_5-C_{15})$heteroaryl (and, in some preferred aspects, a $(C_6-C_{15})$aryl or $(C_5-C_{15})$heteroaryl independently selected from phenyl, naphthyl, pyridinyl, quinolinyl, isoquinolinyl or benzo[d]imidazolyl), each independently substituted with $—(R^{30})_p$. Values for the remaining variables, including $R^{30}$ and p, are as described in the first embodiment, or first through fifth aspects thereof.

In a seventh aspect of the first embodiment, n is 1. Values for the remaining variables are as described in the first embodiment, or first through sixth aspects thereof.

In an eighth aspect of the first embodiment, m is 0. Values for the remaining variables are as described in the first embodiment, or first through seventh aspects thereof.

In a ninth aspect of the first embodiment, each p is independently 0, 1 or 2. Values for the remaining variables are as described in the first embodiment, or first through eighth aspects thereof.

In a tenth aspect of the first embodiment, each p is 0. Values for the remaining variables are as described in the first embodiment, or first through ninth aspects thereof.

In an eleventh aspect of the first embodiment, each q is independently 3 or 4. Values for the remaining variables are as described in the first embodiment, or first through tenth aspects thereof.

In a twelfth aspect of the first embodiment, each r is independently 1 or 2. Values for the remaining variables are as described in the first embodiment, or first through eleventh aspects thereof.

In a thirteenth aspect of the first embodiment, the $—OR^3$ is attached to the ring atom of Ring A which is meta or para to L. Values for the variables, including $R^3$, are as described in the first embodiment, or first through twelfth aspects thereof.

In a fourteenth aspect of the first embodiment, the $—OR^3$ is attached to the ring atom of Ring A which is para to L. Values for the variables, including $R^3$, are as described in the first embodiment, or first through thirteenth aspects thereof.

In a fifteenth aspect of the first embodiment, n is 1 or 2. Values for the remaining variables are as described in the first embodiment, or first through fourteenth aspects thereof.

A second embodiment is a compound of the following structural formula:

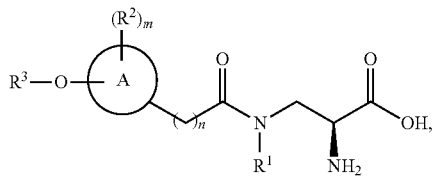

(II)

or a prodrug thereof, or a pharmaceutically acceptable salt of the foregoing. Values for the variables (e.g., Ring A, $R^1$, $R^2$, $R^3$, n, m) are as described in the first embodiment, or any aspect thereof.

In a first aspect of the second embodiment, the $—OR^3$ is attached to the ring atom of Ring A which is meta or para to $—(CH_2)_n—$. Values for the variables, including $R^3$, are as described in the first embodiment, or any aspect thereof.

In a second aspect of the second embodiment, the $—OR^3$ is attached to the ring atom of Ring A which is para to $—(CH_2)_n—$. Values for the variables, including $R^3$, are as described in the first embodiment, or any aspect thereof.

A third embodiment is a compound of the following structural formula:

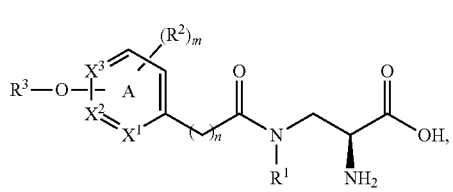
(III)

or a prodrug thereof, or a pharmaceutically acceptable salt of the foregoing, wherein:
$X^1$, $X^2$ and $X^3$ are each >C(H);
$X^1$ is N, and $X^2$ and $X^3$ are each >C(H);
$X^1$ and $X^2$ are each >C(H), and $X^3$ is N; or
$X^1$ and $X^3$ are each >C(H), and $X^2$ is N.

Values for the remaining variables (e.g., $R^1$, $R^2$, $R^3$, n, m) are as described in the first embodiment, or any aspect thereof.

In a first aspect of the third embodiment, $X^1$, $X^2$ and $X^3$ are each >C(H). Values for the remaining variables are as described in the first embodiment, or any aspect thereof, or the third embodiment.

In a second aspect of the third embodiment, $X^1$ is N, and $X^2$ and $X^3$ are each >C(H). Values for the remaining variables are as described in the first embodiment, or any aspect thereof, or the third embodiment.

In a third aspect of the third embodiment, the —$OR^3$ is attached to the ring atom of Ring A which is meta or para to —$(CH_2)_n$—. Values for the variables, including $R^3$, are as described in the first embodiment, or any aspect thereof, or the third embodiment, or first or second aspect thereof.

In a fourth aspect of the third embodiment, the —$OR^3$ is attached to the ring atom of Ring A which is para to —$(CH_2)_n$—. Values for the variables, including $R^3$, are as described in the first embodiment, or any aspect thereof, or the third embodiment, or first or second aspect thereof.

A fourth embodiment is a compound of Structural Formula I, or a pharmaceutically acceptable salt thereof, wherein values for the variables (e.g., Ring A, L, $R^1$, $R^2$, $R^3$, m) are as described in the first embodiment, or any aspect thereof.

A fifth embodiment is a compound of Structural Formula II, or a pharmaceutically acceptable salt thereof, wherein values for the variables (e.g., Ring A, $R^1$, $R^2$, $R^3$, n, m) are as described in the first or second embodiment, or any aspect thereof.

A sixth embodiment is a compound of Structural Formula III, or a pharmaceutically acceptable salt thereof, wherein values for the variables (e.g. $R^1$, $R^2$, $R^3$, n, m, $X^1$, $X^2$, $X^3$) are as described in the first or third embodiment, or any aspect thereof.

Examples of compounds of Structural Formula I include the compounds listed in Table 1, or a prodrug thereof, or a pharmaceutically acceptable salt of the foregoing. In some aspects, a compound of Structural Formula I is selected from the compounds listed in Table 1, or a pharmaceutically acceptable salt thereof.

Methods of making compounds of the disclosure are described herein in the Exemplification, and/or within the abilities of a person skilled in the art.

Compositions and Kits

Typically, for administration to a subject, a compound of the disclosure is formulated with one or more pharmaceutically acceptable carriers. The disclosure provides such compositions, including pharmaceutical compositions. Thus, one embodiment is a composition (e.g., pharmaceutical composition) comprising a compound of the disclosure and a pharmaceutically acceptable carrier. The compositions described herein can be used in the methods described herein, e.g., to supply a compound of the disclosure.

Compounds and compositions described herein can also be in the form of formulations of lipid particles, such as liposomal formulations. Thus, one embodiment is a lipid particle (e.g., a liposome) comprising one or more lipids and a compound of the disclosure.

Also provided herein is a solid lipid particle (e.g., liposome) comprising at least one phospholipid (e.g., a phospholipid containing a $C_4$-$C_{30}$ acyl chain, such as a saturated $C_4$-$C_{30}$ acyl chain, as in dimyristoylphosphatidylcholine (DMPC)) and a therapeutic agent (e.g., a compound of the disclosure) that can embed in a lipid bilayer of the lipid particle. It has been found that oral administration of such solid lipid particles can be used to target the lipid particle (and thereby the therapeutic agent) to immune cells and/or lymph node(s), for example, and thereby enhance colocalization of the lipid particles and immune cells (e.g., in the lymph nodes) and/or enhance lymph node uptake of the lipid particles.

As used herein, "lipid particle" refers to a particle comprising at least one lipid, e.g., a phospholipid, such as a lysophospholipid. Examples of lipid particles include, liposomes, micelles and lipid nanoparticles. Lipid particles, such as liposomes, can be unilamellar or multilamellar. Lipid particles, such as liposomes, can have fluidic lipid membranes, or gel-like or solid lipid membranes, for example, lipid membranes that melt above normal body temperature of a human, or about 37° C. In some aspects, a lipid particle is a liposome. In some aspects, a lipid particle is a lipid nanoparticle. In some aspects, a lipid particle is solid. In some aspects, a lipid particle has a melting temperature above about 37° C., e.g., above about 40° C., above about 45° C., above about 50° C., above about 55° C. or about 55° C.

Examples of phospholipids include dimyristoylphosphatidylcholine (DMPC), 1,2-dioleoyl-sn-glycero-3-phosphocholine 18:1 Δ9-Cis PC (DOPC), 1,2-distearoyl-sn-glycero-3-phosphocholine 18:0 (DSPC), 1-palmitoyl-2-oleoyl-glycero-3-phosphocholine 16:0-18:1 (POPC), phosphatidylserine (PS), phosphatidylcholine (PC), phosphatidylethanolamine, phosphatidyl inositol, bisphosphatidyl glycerol, phosphatidic acid, phosphatidyl alcohol and phosphatidyl glycerol. Phospholipids can be saturated or unsaturated, i.e., contain one or more units of unsaturation, and can contain acyl chains of a variety of lengths. In some aspects, a phospholipid contains a $C_4$-$C_{30}$ acyl chain, e.g., a $C_8$-$C_{26}$, $C_{12}$-$C_{22}$, $C_{10}$-$C_{25}$, $C_{14}$-$C_{18}$ or $C_{16}$-$C_{26}$ acyl chain. Phospholipids can be obtained from various sources, both natural and synthetic. For example, PS can be obtained from porcine brain PS or plant-based soy (soya bean) PS. Egg PC and PS and synthetic PC are available commercially. In some aspects, a phospholipid is not PS, or a salt thereof (e.g., pharmaceutically acceptable salt thereof).

Other lipids suitable for inclusion in the lipid particles described herein include $N^4$-cholesteryl-spermine, or a salt thereof, such as $N^4$-cholesteryl-spermine HCl salt. $N^4$-cholesteryl-spermine HCl salt is also known as Genzyme Lipid 67 (GL67), and is a cholesterol derivatized with spermine to create a cationic lipid HCl salt.

Typically, the molar percentage of a therapeutic agent (e.g., compound of the disclosure) in a lipid particle (e.g., liposome) comprising the therapeutic agent will be from about 1% to about 50%, e.g., from about 1% to about 35%, from about 1% to about 25%, from about 1% to about 15%, from about 3% to about 10%, from about 5% to about 50%, from about 5% to about 45%, from about 15% to about 40%, from about 25% to about 35%, about 1%, about 2%, about 3%, about 4%, about 5%, about 6%, about 7%, about 8%, about 9%, about 10%, about 15%, about 25%, about 30% or about 35%. In some aspects, the molar percentage of a therapeutic agent (e.g., compound of the disclosure) in a lipid particle (e.g., liposome) comprising the therapeutic agent will be less than 35%, e.g., less than 30%, less than 15%, or from about 1% to about 10%.

Typically, the molar percentage of lipid (taken individually or collectively) in a lipid particle (e.g., liposome) described herein will be from about 50% to about 99%, e.g., from about 50% to about 75%, from about 85% to about 99%, about 70%, about 75%, about 85%, about 90%, about 91%, about 92%, about 93%, about 94%, about 95%, about 96%, about 97%, about 98% or about 99%. The molar percentage of each lipid in a lipid particle (e.g., liposome) described herein can be from about 1% to about 99%, e.g., from about 1% to about 50%, from about 1% to about 35%, from about 1% to about 25%, from about 1% to about 15%, from about 3% to about 10%, from about 5% to about 50%, from about 5% to about 45%, from about 15% to about 40%, from about 25% to about 35%, about 1%, about 2%, about 3%, about 4%, about 5%, about 6%, about 7%, about 8%, about 9%, about 10%, about 15%, about 25%, about 30% or about 35%.

A compound of the disclosure can be encapsulated within a lipid particle, such as a liposome, described herein, bound (covalently or non-covalently) to a lipid head group or, preferably, embedded, in whole or in part, covalently or non-covalently, in a lipid bilayer (e.g., of a liposome). Without wishing to be bound by any particular theory, it is believed that compounds of the disclosure may embed in a lipid bilayer of a liposome so as to leave the amino acid residue of the compound of the disclosure exposed to the exterior of the liposome, thereby mimicking the natural surface presentation of, for example, PS.

In some aspects, the one or more lipids comprises a phospholipid, or a pharmaceutically acceptable salt thereof, e.g., 1,2-dimyristoyl-sn-glycero-3-phosphocholine (DMPC), or a pharmaceutically acceptable salt thereof. In some aspects, the phospholipid is a saturated phospholipid, e.g., a saturated phospholipid containing a $C_4$-$C_{30}$ acyl chain. In some aspects, the phospholipid is unsaturated, e.g., an unsaturated phospholipid containing a $C_4$-$C_{30}$ acyl chain. In some aspects, the phospholipid is selected from DMPC, DSPC, DOPC or POPC, or a pharmaceutically acceptable salt of the foregoing. In some aspects, the phospholipid is DMPC or DSPC, or a pharmaceutically acceptable salt of the foregoing.

In some aspects, a lipid particle (e.g., liposome) further comprises an antigen, such as any of the antigens described herein. Thus, in some aspects, a lipid particle further comprises a gene therapy. In some further aspects, the gene therapy comprises DNA and/or RNA and a viral vector. In some aspects, the viral vector is derived from an adeno-associated virus (AAV), such as a recombinant AAV. In some aspects, the AAV is AAV9. Other examples of viral vectors suitable for use in the context of the present disclosure include viral vectors derived from retrovirus, herpes virus, adenovirus, lentivirus, rabies virus, lentivirus, VSV, poxvirus (e.g., vaccinia virus, variola virus, canarypox), reovirus, semliki forest virus, yellow fever virus, sindbis virus, togavirus, baculovirus, bacteriophages, alphavirus, and flavavirus. In some aspects, the antigen, e.g., gene therapy comprising DNA and/or RNA and a viral vector, is encapsulated within the lipid particle.

Lipid particles further comprising an antigen, and formulations comprising such lipid particles, are expected to be particularly useful for applications involving delivery of a gene therapy (e.g., a gene therapy comprising DNA and/or RNA) to a subject. The lipid particles are expected to promote co-presentation of the gene therapy and the compound of the disclosure to the immune system. Such particles can be formulated for oral and/or parenteral (e.g., subcutaneous, intramuscular, intravenous, intradermal) administration, e.g., as by injection.

Another embodiment is a composition (e.g., pharmaceutical composition) comprising a plurality of lipid particles (e.g., a plurality of lipid particles comprising a compound of the disclosure). In some aspects, a composition further comprises a pharmaceutically acceptable carrier.

Compositions described herein and, hence, compounds of the disclosure, may be administered orally, parenterally (including subcutaneously, intramuscularly, intravenously and intradermally), by inhalation spray, topically, rectally, nasally, buccally, vaginally or via an implanted reservoir. The terms "parenteral" and "parenterally," as used herein, include subcutaneous, intracutaneous, intravenous, intramuscular, intraocular, intravitreal, intra-articular, intra-arterial, intra-synovial, intrasternal, intrathecal, intralesional, intrahepatic, intraperitoneal, intralesional and intracranial injection or infusion techniques. In some aspects, a composition described herein is administrable intravenously and/or intraperitoneally. In some aspects, a composition described herein is administrable orally. In some aspects, a composition described herein is administrable subcutaneously. Preferably, a composition described herein is administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. In addition to the compound of the disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the disclosure can also be in microencapsulated form with one or more excipients, as noted above. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another aspect, a compound of the disclosure can be provided in an extended (or "delayed" or "sustained") release composition. This delayed-release composition comprises the compound of the disclosure and a delayed-release component. Such a composition allows targeted release of the compound, for example, into the lower gastrointestinal tract, for example, into the small intestine, the large intestine, the colon and/or the rectum. In certain aspects, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition can provide controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered subcutaneously, intraperitoneally or intravenously, e.g., in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, dextrose, water, Ringer's solution, lactated Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Compositions described herein can also be administered in the form of suppositories for rectal administration. These can be prepared by mixing a compound of the disclosure with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents.

Suitable carriers include, but are not limited to, mineral oil, sorbitan monostearate, polysorbate 60, cetyl esters wax, cetearyl alcohol, 2-octyldodecanol, benzyl alcohol and water. Suitable carriers also include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition, for example, consequences for red blood cells.

Other pharmaceutically acceptable carriers that can be used in the compositions described herein include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives thereof, such as hydroxyalkylcyclodextrins, including hydroxypropyl-β-cyclodextrins, such as 2- and/or 3-hydroxypropyl-β-cyclodextrins, or other solubilized derivatives thereof can also be advantageously used as a pharmaceutically acceptable carrier in the compositions described herein, e.g., to enhance delivery of agents described herein.

One embodiment is a composition comprising a compound of the disclosure and a cyclodextrin or chemically modified derivative thereof. In some aspects, the cyclodextrin or chemically modified derivative thereof comprises a hydroxyalkylcylclodextrin, e.g., a hydroxypropyl-β-cyclodextrin. In some aspects, the compound of the disclosure and the cyclodextrin (e.g., hydroxyalkylcylclodextrin, such as hydroxypropyl-β-cyclodextrin) are present in a ratio of from about 1 to about 50 weight/weight (w/w) to about 1 to about 250 w/w, e.g., from about 1 to about 50 w/w to about 1 to about 100 w/w, about 1 to about 80 w/w or about 1 to about 166 w/w. In some aspects, the composition further comprises a diluent, such as water. In some aspects, the composition further comprises a sweetening agent and/or flavoring agent.

In some aspects, the composition is a liquid dosage form; in further aspects, the composition is a liquid dosage form for oral administration.

In some aspects, a composition described herein further includes one or more additional therapeutic agents, e.g., for use in combination with a compound of the disclosure.

Some embodiments provide a combination (e.g., pharmaceutical combination) comprising a compound of the disclosure (e.g., a composition described herein comprising a compound of the disclosure) and one or more additional therapeutic agents (e.g., one or more compositions comprising one or more additional therapeutic agents). Such combinations are particularly useful as, for example, when the compound of the disclosure and the one or more additional therapeutic agents are to be administered separately. In a combination provided herein, the compound of the disclosure and the one or more additional therapeutic agents can be administrable by the same route of administration or by different routes of administration.

One embodiment is a kit comprising a compound of the disclosure (e.g., a composition described herein comprising a compound of the disclosure) and an antigen (e.g., any of the antigens described herein, such as an antigenic therapy). In one aspect, the kit comprises a therapeutically effective amount of the compound of the disclosure (e.g., an amount sufficient to immunotolerize a subject to an antigen with which it is intended to be administered; a therapeutically effective amount of the compound to treat a disease, disorder or condition described herein). In some aspects, wherein the antigen is an antigenic therapy, the kit comprises a therapeutically effective amount of the antigenic therapy to treat the disease, disorder or condition. In some aspects, a kit further comprises an additional therapeutic agent(s) (e.g., a composition comprising an additional therapeutic agent(s)). In some aspects, the kit further comprises written instructions for administering the compound of the disclosure and/or the antigen and/or the additional agent(s) to a subject to treat a disease, disorder or condition described herein.

Suitable additional therapeutic agents include those described herein with respect to combination therapies.

The compositions described herein can be provided in unit dosage form. The amount of active ingredient that can be combined with a carrier to produce a unit dosage form will vary depending, for example, upon the subject being treated and the particular mode of administration. Typically, a unit dosage form will contain from about 1 to about 1,000 mg of active ingredient(s), e.g., from about 1 to about 500 mg, from about 1 to about 250 mg, from about 1 to about 150 mg, from about 0.5 to about 100 mg, or from about 1 to about 50 mg of active ingredient(s). In some aspects, a unit dosage form contains from about 0.01 mg to about 100 mg of active ingredient(s), e.g., from about 0.1 mg to about 50 mg, from about 0.1 mg to about 10 mg, from about 0.5 mg to about 50 mg of active ingredient(s). In some aspects, a unit dosage form contains from about 1 mg to about 5,000 mg of active ingredient(s) e.g., from about 10 mg to about 2,500 mg, from about 15 mg to about 1,000 mg or from about 100 mg to about 1,000 mg of active ingredient(s). In some aspects, a unit dosage form contains about 15 mg, about 30 mg, about 50 mg, about 100 mg, about 125 mg or about 150 mg of active ingredient(s).

In some aspects, the concentration of one or more therapeutic agents provided in a pharmaceutical composition is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v; and/or greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some aspects, the concentration of one or more therapeutic agents provided in a pharmaceutical composition is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% w/w, w/v or v/v. In some embodiments, the concentration of one or more therapeutic agents provided in a pharmaceutical composition is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

Methods of Use

It has now been found that various compounds of the present disclosure and compositions described herein are capable of binding TIM, e.g., with higher affinity than its natural ligand, phosphatidyl serine, and diminishing the immune response.

One embodiment is a method of modulating the expression or activity of a T cell immunoglobulin and mucin domain (TIM) receptor, comprising contacting a cell (e.g., a cell expressing a TIM receptor, such as an immune cell) with a compound of the disclosure (e.g., a therapeutically effective amount of a compound of the disclosure). UM receptors are type 1 cell-surface glycoproteins, and TIM1, TIM3 and TIM4, TIM receptors expressed in humans, have been identified as phosphatidylserine receptors. TIM1 is preferentially expressed on T-helper 2 cells, and operates as a potent costimulatory molecule for T-cell activation. TIM3 is preferentially expressed on T-helper 1 cells, type 1 T-cells and dendritic cells, and generates an inhibitory signal resulting in apoptosis of T-helper 1 cells and type 1 T-cells. TIM4 is expressed on antigen-presenting cells, and mediates phagocytosis of apoptotic cells, thereby promoting tolerance. In some aspects, the TIM receptor is a TIM3 receptor. In some aspects, the TIM receptor is a TIM4 receptor. In some aspects, the TIM receptor is a TIM1 receptor. "TIM" is also referred to, for example, in the literature, as "Tim."

It has now also been found that agonists of TIM receptors inhibit the activity of at least toll-like receptor (TLR) 3 and TLR7, without substantially inhibiting the activity of TLRs 2 and 4, which largely recognize patterns presented by bacteria. Toll-like receptors (TLRs) form a family of pattern recognition receptors that are expressed on innate immune cells, and constitute the immune system's first line of defense against microbes. To date, ten human subtypes of TLRs have been identified. TLRs 1, 2, 4, 5, 6 and 10 are expressed on the cell surface, and TLRs 3, 7, 8 and 9 are localized to the endoplasmic reticulum, endosomes and lysosomes. TLRs 1, 2 and 6 recognize and bind to bacterial lipoproteins and glycolipids. TLRs 3, 7, 8 and 9 recognize and bind to nucleic acids, such as viral dsRNA (TLR3), ssRNA (TLR7, TLR8) and unmethylated CpG DNA (TLR9). TLR4 recognizes and binds to fibronectin and LPS. TLR5 recognizes and binds to bacterial flagellin. Without wishing to be bound by any particular theory, it is believed that compounds of the disclosure do not result in general immunosuppression, but may exert their effects in a more selective and specific manner.

Another embodiment is a method of modulating (e.g., inhibiting) the activity of TLR3, TLR7, TLR8 and/or TLR9, comprising contacting a cell (e.g., a cell expressing TLR3, TLR7, TLR8 and/or TLR9; an immune cell) with a compound of the disclosure (e.g., a therapeutically effective amount of a compound of the disclosure). In some aspects, the compound of the disclosure selectively modulates (e.g., inhibits) the activity of TLR3, TLR7, TLR8 and/or TLR9, e.g., modulates (e.g., inhibits) the activity of TLR3, TLR7, TLR8 and/or TLR9 to a greater extent than it modulates the activity of TLRs 1, 2, 4, 5, 6 and/or 10. For example, modulation (e.g., inhibition) of the activity of TLR3, TLR7, TLR8 and/or TLR9 by a compound of the disclosure can be more than two-fold greater, e.g., more than five-fold, more than 10-fold, more than 25-fold or more than 100-fold greater, than modulation (e.g., inhibition) of the activity of TLRs 1, 2, 4, 5, 6 and/or 10 by the compound. In some aspects, the compound does not modulate (e.g., inhibit) the activity of TLRs 1, 2, 4, 5, 6 and/or 10 to a measurable extent.

In some aspects of the methods described herein, the cell is an immune cell, e.g., a T-cell, such as a regulatory T-cell, a natural killer (NK) cell, a macrophage, a neutrophil, a myeloid-derived suppressor cell or a dendritic cell. In some aspects, an immune cell is FoxP3+ and/or CD4+, such as a FoxP3+ and/or CD4+ T-cell. In some aspects, the immune cell is a B-cell, such as a regulatory B-cell. In some aspects, an immune cell (e.g., regulatory B-cell) is CD19+, CD71+, IgM+, CD24+, CD38+ and/or CD27+.

In some aspects of the methods described herein, the method is conducted in vitro. In other aspects of the methods described herein, the method is conducted in vivo. In some aspects, therefore, the cell (e.g., immune cell) is in a subject (e.g., a subject having a disease, disorder or condition described herein).

Another embodiment is a method of immunotolerizing a subject in need thereof (e.g., a subject having an autoimmune disorder, such as an autoimmune disorder described herein), comprising administering to the subject a therapeutically effective amount of a compound of the disclosure, e.g., in the form of a composition described herein.

Another embodiment is a method of immunotolerizing a subject in need thereof to an antigen (e.g., an antigenic therapy), comprising administering to the subject a therapeutically effective amount of a compound of the disclosure, e.g., in the form of a composition described herein. Some aspects comprise administering to the subject the antigen, or an immunogenic fragment thereof, and a therapeutically effective amount of a compound of the disclosure, e.g., in the form of a composition described herein. Some aspects comprise administering to the subject a composition described herein comprising the compound of the disclosure and the antigen, or an immunogenic fragment thereof, e.g., a composition comprising a plurality of lipid particles, wherein each lipid particle comprises the compound of the disclosure and the antigen, or an immunogenic fragment thereof. In some aspects, the antigen, or an immunogenic fragment thereof, and the compound of the disclosure are administered to the subject in separate formulations.

"Immunotolerizing," as used herein, refers to diminishing and/or eliminating an immune response, e.g., to an antigen. An immune response can, for example, be evidenced by immunological hyperactivity, inflammatory cytokine release and/or activation of immune cells such as macrophages, neutrophils, eosinophils, T-cells and B-cells. "Immunotolerizing," as used herein, contemplates, for example, decreasing immunological hyperactivity, inhibiting inflammatory cytokine release and/or inhibiting activation and/or neutralizing immune cells such as macrophages, neutrophils, eosinophils, T-cells and B-cells. In a clinical setting, immunotolerizing may be evidenced, for example, by reduced severity of autoimmune disease and/or improved activity of administered antigenic therapy.

Thus, the process of immunotolerizing can be viewed along a continuum that ranges from immunological hyperactivity to immunological hypoactivity to immunological non-responsiveness, e.g., to an antigen. "Immunotolerizing" contemplates incremental improvements along this continuum towards immunological non-responsiveness as well as inducing immunological hypoactivity or immunological non-responsiveness. In other words, immunotolerizing includes reducing the level of immune intolerance and inducing immune tolerance. In certain preferred embodiments described herein, the method induces immune tolerance.

In some aspects, a subject showing immune intolerance or an immune intolerant subject has a measurable immune response, e.g., to an antigen, such as measurable antibody production in response to an antigen. In some aspects, a subject showing immune tolerance or an immune tolerant subject, does not have a measurable immune response, e.g., to an antigen, such as measurable antibody production in response to an antigen. ELISA and/or activity assays, including those described herein, are known in the art, and can be used to measure antibody production indicative of immune intolerance.

In some autoimmune diseases, antibodies are not always present. Immune intolerance in such cases can be evident by clinical symptoms of autoimmune disease and/or the presence of self-reactive T-cells or B-cells and/or an increase in other inflammatory immune cells, such as neutrophils, eosinophils, etc. In some aspects, a subject showing immune intolerance or an immune intolerant subject (e.g., subject having an autoimmune disease, such as an autoimmune disease described herein) has a measurable cytokine response. For example, a subject having rheumatoid arthritis may have a measurable TNF-alpha response. In some aspects, a subject showing immune tolerance or an immune tolerant subject (e.g., subject having an autoimmune disease, such as an autoimmune disease described herein) does not have a measurable cytokine response.

Immunotolerizing can be achieved in a general or antigen-specific manner, resulting, for example, in general or antigen-specific immune tolerance (e.g., general or specific, acquired or adaptive, immune tolerance), respectively. Indicators of general immunotolerization include, for example: (a) absence and/or diminishment of immunological hyperactivity and/or anti-inflammatory cytokine release; (b) neutralization of immune cells such as macrophages, neutrophils, eosinophils, T-cells and B-cells; (c) an increase in number of regulatory T-cells and/or in the activity or level of tolerogenic T-cells (e.g., FoxP3+/CD4+ T-cells; CD4+/CD25$^{hi}$/Foxp3+/CTLA4+/Tim3+/NRP1+/ICOS− T-cells; CD4+/CD25$^{hi}$/Foxp3+/CTLA4+/Tim3+ T-cells; and/or CD4+/CD25$^{hi}$/Foxp3+/CTLA4+/NRP1+/ICOS− T-cells); and/or (d) an increase in the number of regulatory B-cells (e.g., CD19+/CD71+/IgM+/CD24+/CD38+/CD27+ B-cells; and/or CD19+/CD71+/IgM+B-cells). Indicators of antigen-specific immunotolerization include, for example: (a) an increase in the number of antigen-specific regulatory T-cells (e.g., CD$+/FoxP3+ T-cells; CD4+/CD25$^{hi}$/Foxp3+/CTLA4+/Tim3+/NRP1+/ICOS− T-cells; CD4+/CD25$^{hi}$/Foxp3+/CTLA4+/Tim3+ T-cells; and/or CD4+/CD25$^{hi}$/Foxp3+/CTLA4+/NRP1+/ICOS− T-cells); (b) a decrease in antigen-specific antibody titer and/or number of B cells, including antigen-specific memory B cells; (c) a decrease in IL-6 and/or IL-17; (d) an increase in TGF-beta, IL-10, IL-35, CD40, CD80 and/or CD86; (e) hyporesponsiveness following re-challenge with an antigen; and/or (f) an increase in the number of antigen-specific regulatory B-cells (e.g., CD19+/CD71+/IgM+/CD24+/CD38+/CD27+B-cells; and/or CD19+/CD71+/IgM+B-cells). Techniques for evaluating these indicators are known in the art and described herein. For example, certain of the aforementioned indicators can be evaluated using culture conditions.

In autoimmune diseases, treatment with compounds of the disclosure leads to expansion of natural regulatory T-cells. Such treatment does not interfere with innate immune response, such as that mounted by innate immune cells responding to danger signals from pathogens, but results in general adaptive immunotolerization. Thus, immunotolerizing can be achieved herein without general innate immune suppression, such that, for example, a subject can still mount an innate immune response to an antigen (e.g., pathogen). In some aspects, immunotolerizing is general adaptive immunotolerization. In some aspects, immunotolerizing is antigen-specific, for example, resulting in reduced immune intolerance to a particular antigen(s) or immune tolerance to the particular antigen(s).

It will be understood that antigen-specific immunotolerizing can be achieved in accordance with the methods described herein not only by administering to a subject the specific antigen and a therapeutically effective amount of a compound of the disclosure or composition described herein, but also or alternatively by administering to a subject an immunogenic fragment of the specific antigen and a therapeutically effective amount of a compound of the disclosure or composition described herein.

As used herein, an "immunogenic fragment" of an antigen refers to a fragment of the antigen that induces an immune response to the antigen. An immunogenic fragment of an antigen may induce an immune response in a subject that is similar in extent to the immune response induced by the antigen itself, but need not induce the same extent of immune response as the antigen itself, so long as, when administered in accordance with the methods described herein, it has an immunotolerizing effect.

Another embodiment is a method of inhibiting or reducing an antigen-specific antibody titer in a subject, comprising administering to the subject the antigen, or an immunogenic fragment thereof, and a therapeutically effective amount of a compound of the disclosure, e.g., in the form of a composition described herein. Some aspects comprise administering to the subject a composition described herein comprising the compound of the disclosure and the antigen, or an immunogenic fragment thereof, e.g., a composition comprising a plurality of lipid particles, wherein each lipid particle comprises the compound of the disclosure and the antigen, or an immunogenic fragment thereof. In some aspects, the antigen, or an immunogenic fragment thereof, and the compound of the disclosure are administered to the subject in separate formulations.

In some aspects of a method described herein, the antigen is an allergen, such as a food allergen or latex allergen. Examples of food allergens include peanut allergen, such as Ara h I or Ara h II; walnut allergen, such as Jug r I; brazil nut allergen, such as albumin; shrimp allergen, such as Pen a I; egg allergen, such as ovomucoid; milk allergen, such as bovine β-lactoglobin; wheat gluten antigen, such as gliadin); and fish allergen, such as parvalbumins. An example of a latex allergen is Hev b 7. Other allergens include antigen E, or Amb a I (ragweed pollen); protein antigens from grass, such as Lol p 1 (grass); dust mite allergens, such as, Der pI and Der PII (dust mites); Fel d I (domestic cat); and protein antigens from tree pollen, such as Bet v1 (white birch), and Cry j 1 and Cry j 2 (Japanese cedar). The allergen source listed in parentheses next to each allergen indicates the source with which the indicated allergen is typically associated.

Another embodiment is a method of inducing a population of regulatory T-cells in a subject, comprising administering to the subject a therapeutically effective amount of a compound of the disclosure, e.g., in the form of a composition described herein. Some aspects further comprise administering to the subject an antigen, or an immunogenic fragment thereof, in response to which the population of regulatory T-cells is being induced. Some aspects comprise administering to the subject a composition described herein comprising the compound of the disclosure and the antigen, or an immunogenic fragment thereof, e.g., a composition comprising a plurality of lipid particles, wherein each lipid particle comprises the compound of the disclosure and the antigen, or an immunogenic fragment thereof. In some aspects, the antigen, or an immunogenic fragment thereof, and the compound of the disclosure are administered to the subject in separate formulations.

Without wishing to be bound by any particular theory, it is believed that the compounds of the disclosure induce a population of regulatory T-cells primarily by expanding the population of natural regulatory T-cells (nTregs, e.g., regulatory T-cells which are FoxP3+/NRP1+). The compounds of the disclosure also induce or upregulate inducible regulatory T-cells (iTregs, e.g., FoxP3+ T-cells, FoxP3+/TIM3+ T-cells). Accordingly, in some aspects, a method of inducing a population of regulatory T-cells is a method of expanding a population of natural regulatory T-cells (e.g., regulatory T-cells which are FoxP3+/NRP1+), for example, without substantially inducing inducible regulatory T-cells. Neuropilin-1 (Nrp1) expression can be used to distinguish between natural and inducible regulatory T-cells, for example, as described herein. Thus, in some aspects, a method of inducing a population of regulatory T-cells is a method of inducing a population of regulatory T-cells expressing Nrp1 (e.g., FoxP3+/NRP1+ T-cells) as, for example, by expanding a population of natural regulatory T-cells. Without wishing to be bound by any particular theory, it is expected that the ability to expand a population of natural regulatory T-cells (e.g., regulatory T-cells which are FoxP3+/NRP1+), for example, without substantially inducing inducible regulatory T-cells, will be beneficial in treating autoimmune diseases without effecting general immunosuppression.

In some aspects, regulatory T-cells are FoxP3+, e.g., FoxP3+/TIM3+, FoxP3+/NRP1+. Whether a regulatory T-cell is positive (+) or negative (−) for any of the aforementioned markers can be determined, for example, by flow cytometry analysis.

Another embodiment is a method of increasing the activity or level of tolerogenic T-cells in a subject, comprising administering to the subject a therapeutically effective amount of a compound of the disclosure, e.g., in the form of a composition described herein.

Another embodiment is a method of inducing a population of regulatory B-cells in a subject, comprising administering to the subject a therapeutically effective amount of a compound of the disclosure, e.g., in the form of a composition described herein. Some aspects further comprise administering to the subject an antigen, or an immunogenic fragment thereof, in response to which the population of regulatory B-cells is being induced. Some aspects comprise administering to the subject a composition described herein comprising the compound of the disclosure and the antigen, or an immunogenic fragment thereof, e.g., a composition comprising a plurality of lipid particles, wherein each lipid particle comprises the compound of the disclosure and the antigen, or an immunogenic fragment thereof. In some aspects, the antigen, or an immunogenic fragment thereof, and the compound of the disclosure are administered to the subject in separate formulations.

It has been found that the compounds of the disclosure increase expression of certain regulatory markers on B-cells, such as CD19, CD71 and IgM, and thereby induce a population of CD19+/CD71+/IgM+ B-cells. In some aspects, regulatory B-cells are CD19+, CD71+, IgM+, CD24+, CD38+ and/or CD27+, e.g., CD19+/CD71+/IgM+. Whether a regulatory B-cell is positive (+) or negative (−) for any of the aforementioned markers can be determined, for example, by flow cytometry analysis.

Another embodiment is a method of treating an autoimmune disorder in a subject (e.g., a subject in need thereof), comprising administering to the subject a therapeutically effective amount of the disclosure, e.g., in the form of a composition described herein. It will be appreciated that in autoimmune disorders, it may be desirable to induce general adaptive immunotolerization (e.g., immune tolerance) as, for example, by inducing a population of regulatory T-cells, or specific immunotolerization (e.g., immune tolerance) as, for example, by immunotolerizing a subject to a self-antigen associated with the autoimmune disorder, or an immunogenic fragment thereof. Thus, in some aspects of a method of treating an autoimmune disorder, the method further comprises administering (e.g., co-administering) a self-antigen associated with the autoimmune disorder, or an immunogenic fragment thereof, to the subject. Some aspects comprise administering to the subject a composition described herein comprising the compound of the disclosure and the self-antigen, or an immunogenic fragment thereof, e.g., a composition comprising a plurality of lipid particles, wherein each lipid particle comprises the compound of the disclosure and the self-antigen, or an immunogenic fragment thereof. In some aspects, the self-antigen, or an immunogenic fragment thereof, and the compound of the disclosure are administered to the subject in separate formulations.

Specific examples of autoimmune disorders treatable according to the methods described herein include achalasia, Addison's disease, adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal and neuronal neuropathy (AMAN), Baló disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss Syndrome (CSS) or eosinophilic granulomatosis (EGPA), cicatricial pemphigoid, Cogan's syndrome, cold agglutinin disease, congenital heart block, Coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (acne inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, Lyme disease chronic, Meniere's disease, microscopic polyangiitis (MPA), mixed connective tissue disease (MCTD), Mooren's ulcer, Mucha-Habermann disease, multifocal motor neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonage-Turner syndrome, pemphigus, peripheral neuropathy, perivenous encephalomyelitis, pernicious anemia (PA), POEMS syndrome, polyarteritis nodosa, polyglandular syndromes type I, II and III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis/giant cell arteritis, thrombocytopenic purpura (TTP), thyroid eye disease (TED), Tolosa-Hunt syndrome (THS), transverse myelitis, Type 1 diabetes, ulcerative colitis (UC), undifferentiated connective tissue disease (UCTD), uveitis, vasculitis, vitiligo and Vogt-Koyanagi-Harada Disease.

In some aspects, the autoimmune disorder is a neurological autoimmune disorder. Examples of neurological autoimmune disorders include multiple sclerosis, neuromyelitis optica, myasthenia gravis, anti-myelin oligodendrocyte glycoprotein antibody disease (MOG), a MOG antibody-associated disorder (MOGAD, e.g., MOG-associated childhood demyelinating disease), autoimmune encephalitis, acute disseminated encephalomyelitis (ADEM), chronic meningitis, central nervous system vasculitis, Guillain-Barre syndrome, Hashimoto's thyroiditis, steroid responsive encephalopathy associated with autoimmune thyroiditis (SREAT), neurosarcoidosis, optic neuritis and transverse myelitis.

In some aspects, the autoimmune disorder is rheumatoid arthritis, systemic lupus erythematosus, inflammatory bowel disease (IBD), multiple sclerosis, type 1 diabetes mellitus, Guillain-Barre syndrome, chronic inflammatory demyelinating polyneuropathy, psoriasis, Graves' disease, Hashimoto's thyroiditis, myasthenia gravis or vasculitis. In some aspects, the autoimmune disorder is systemic lupus erythematosus. In some aspects, the autoimmune disorder is IBD.

In some aspects, the autoimmune disorder is multiple sclerosis, neuromyelitis optica, myelin oligodendrocyte glycoprotein antibody-associated disease (MOGAD), rheumatoid arthritis or myasthenia gravis. In some aspects, the autoimmune disorder is multiple sclerosis. In some aspects, the autoimmune disorder is neuromyelitis optica. In some aspects, the autoimmune disorder is MOGAD. In some aspects, the autoimmune disorder is rheumatoid arthritis. In some aspects, the autoimmune disorder is myasthenia gravis.

Another embodiment is a method of treating multiple sclerosis in a subject in need thereof, comprising administering to the subject a therapeutically effective amount of a compound of the disclosure, e.g., in the form of a composition described herein.

The clinical management of multiple sclerosis typically follows one of two paradigms: the escalation paradigm or the induction/maintenance paradigm. In the escalation paradigm, disease-modifying therapies (DMTs) of increasing efficacy and potency (and with greater risks of serious adverse events) are given following treatment failure with a lower-potency and lower-efficacy DMT. Typically, standard of care therapy in the escalation paradigm involves treatment with glatiramer acetate, interferon beta and/or teriflunimude, which is escalated upon treatment failure to fingolimod and/or dimethyl fumarate, which is further escalated upon treatment failure to natalizumab and/or anti-B-cell, which is yet further escalated upon treatment failure to alemtuzumab and/or mitoxantrone.

The induction/maintenance treatment paradigm for clinical management of multiple sclerosis includes an induction phase followed by a maintenance phase. Patients are treated with high potency DMTs to induce disease control during the induction phase, and are subsequently switched to a safer, lower potency DMT for maintenance therapy during the maintenance phase.

Disease-modifying therapies (DMT) used in the treatment of multiple sclerosis include interferon beta-la (e.g., AVONEX®, REBIF®), interferon beta-lb (e.g., BETASERON®, EXTAVIA®), glatiramer acetate (e.g., COPAXONE®, GLATOPA®), ofatumumab (e.g., KESIMPTA®), peginterferon beta-la (e.g., PLEGRIDY®), teriflunomide (e.g., AUBAGIO®), monomethyl fumarate (e.g., BAFIERTAM™), dimethyl fumarate (e.g., TECFIDERA®), fingolimod (e.g., GILENYA®), cladribine (e.g., MAVENCLAD®), siponimod (e.g., MAYZENT®), ponesimob (e.g., PONVORY®), diroximel fumarate (e.g., VUMERITY®), ozanimob (e.g., ZEPOSIA®), alemtuzumab (e.g., LEMTRADA®), mitoxantrone (e.g., NOVANTRONE®), ocrelizumab (e.g., OCREVUS®) and natalizumab (e.g., TYSABRI®). Examples of high-potency DMTs include, but are not limited to, natalizumab, alemtuzumab, anti-B-cell and mitoxantrone. Examples of lower potency DMTs include, but are not limited to, glatiramer acetate, interferon beta, teriflunimide, DMF and fingolimob.

Natalizumab is a recombinant humanized IgG4κ monoclonal antibody produced in murine myeloma cells. Natalizumab binds to the α4-subunit of α4β1 and α4β7 integrins expressed on the surface of all leukocytes except neutrophils, and inhibits the α4-mediated adhesion of leukocytes to their counter-receptor(s). Natalizumab injection is indicated as monotherapy for the treatment of relapsing forms of multiple sclerosis, including clinically isolated syndrome, relapsing-remitting disease, and active secondary progressive disease, in adults. Glatiramer acetate injection is indicated for the treatment of relapsing forms of multiple sclerosis, including clinically isolated syndrome, relapsing-remitting disease, and active secondary progressive disease, in adults. Dimethylfumarate for oral use is indicated for the treatment of relapsing forms of multiple sclerosis.

In some aspects, the multiple sclerosis is previously untreated. In alternative aspects, the multiple sclerosis is previously treated, e.g., with a standard of care therapy, such as natalizumab (TYSABRI®), glatiramer acetate and/or dimethyl fumarate, or a DMT.

In some aspects, multiple sclerosis is primary progressive multiple sclerosis (PPMS). In some aspects, multiple sclerosis is relapsing remitting multiple sclerosis (RRMS). In some aspects, multiple sclerosis is clinically isolated syndrome (CIS). In some aspects, multiple sclerosis is secondary progressive multiple sclerosis (SPMS).

In some aspects (e.g., wherein the autoimmune disease is multiple sclerosis), the method comprises administering to the subject a therapeutically effective amount of an induction therapy comprising a compound of the disclosure, e.g., in the form of a pharmaceutical composition. In some aspects (e.g., wherein the autoimmune disease is multiple sclerosis), the method comprises administering to the subject a therapeutically effective amount of a maintenance therapy comprising a compound of the disclosure, e.g., in the form of a pharmaceutical composition. In some aspects (e.g., wherein the autoimmune disease is multiple sclerosis), the method comprises administering to the subject a therapeutically effective amount of an induction therapy comprising a compound of the disclosure, e.g., in the form of a pharmaceutical composition, and (e.g., followed by) a therapeutically effective amount of a maintenance therapy comprising the compound of the disclosure, e.g., in the form of a pharmaceutical composition.

In some aspects (e.g., wherein the autoimmune disease is multiple sclerosis), a compound of the disclosure is administered in combination with a DMT, such as natalizumab and/or glatiramer acetate and/or dimethylfumarate, and, in some further aspects, the method further comprises administering a DMT, such as natalizumab and/or glatiramer acetate and/or dimethyl fumarate, to the subject.

In some aspects, an autoimmune disorder is previously untreated. In alternative aspects, an autoimmune disorder is previously treated, e.g., with a standard of care therapy, such as natalizumab (TYSABRI®) or glatiramer acetate for multiple sclerosis.

Examples of self-antigens associated with autoimmune disorders include thyroid stimulating hormone receptor of the thyroid gland (Grave's disease); thyroid antigens, such as thyroid peroxidase (Hashimoto's thyroiditis); β cell antigens, such as glutamic acid decarboxylase and insulin (type I diabetes); cytochrome P450 antigens (Addison's disease); myelin proteins, such as myelin basic protein (multiple sclerosis); uveal antigens (uveitis); gastric parietal cell antigens, such as $H^+/ATPase$ and intrinsic factor (pernicious anemia); transglutaminase (gluten enteropathy); myocardial cell proteins, such as myosin (myocarditis, rheumatic heart disease); platelet antigens, such as GP IIb/IIIa (idiopathic thrombocytopenic purpura); red blood cell membrane proteins (autoimmune hemolytic anemia); neutrophil membrane proteins (autoimmune neutropenia); basement membrane antigens, such as type IV collagen .alpha.3 chain, (Goodpasture's disease); intrahepatic bile duct/mitochondrial antigens, such as 2-oxoacid dehydrogenase complexes (primary biliary cirrhosis); hepatocyte antigens, such as cytochrome P450 and 206 (autoimmune hepatitis); acetylcholine receptors (myasthenia gravis); desmogleins (pemphigus and other bullous diseases). The disorder listed in parentheses next to each self-antigen indicates the autoimmune disorder with which the indicated self-antigen is typically associated.

Compounds of the disclosure and compositions described herein are expected to be useful adjunctive therapies in the context of antigenic therapy, such as gene therapy, e.g., as by inhibiting an undesirable immune response to the antigenic therapy and/or enabling dosing and/or repeat dosing of the antigenic therapy. Another embodiment is a method of treating a disease, disorder or condition in a subject in need thereof with an antigenic therapy, comprising administering to the subject a compound of the disclosure, e.g., in the form of a composition described herein. In some aspects, the compound of the disclosure is administered in an amount sufficient to immunotolerize the subject to the antigenic therapy. In some aspects, the method further comprises administering (e.g., co-administering) to the subject the antigenic therapy (e.g., a therapeutically effective amount of the antigenic therapy), for example, concurrently or sequentially with the compound of the disclosure. Some aspects comprise administering to the subject a composition described herein comprising the compound of the disclosure and the antigenic therapy, e.g., a composition comprising a plurality of lipid particles, wherein each lipid particle comprises the compound of the disclosure and the antigenic therapy. In some aspects, the antigenic therapy and the compound of the disclosure are administered to the subject in separate formulations.

In some aspects, the antigenic therapy is an antibody therapy (e.g., monoclonal antibody therapy), including chimeric, humanized and fully-human antibody therapies. Specific examples of antibody therapies include anti-tumor necrosis factor (anti-TNF) therapies, such as adalimumab (Humira®; for rheumatoid arthritis, juvenile idiopathic arthritis, psoriatic arthritis, ankylosing spondylitis, Crohn's disease, ulcerative colitis, plaque psoriasis, hidradenitis suppurativa, uveitis) and infliximab (Remicade®, for Crohn's disease, pediatric Crohn's disease, ulcerative colitis, pediatric ulcerative colitis, rheumatoid arthritis, ankylosing spondylitis, psoriatic arthritis, plaque psoriasis), golimumab (Simponi®, for rheumatoid arthritis, psoriatic arthritis, ankylosing spondylitis, polyarticular juvenile idiopathic arthritis), etanercept (Enbrel®, for rheumatoid arthritis, polyarticular juvenile idiopathic arthritis, psoriatic arthritis, ankylosing spondylitis, plaque psoriasis) and certolizumab pegol (Cimzia®, for Crohn's disease, rheumatoid arthritis, psoriatic arthritis, ankylosing spondylitis, non-radiographic axial spondyloarthritis, plaque psoriasis).

In some aspects, the antigenic therapy is a protein replacement therapy, for example, enzyme replacement therapy. Examples of protein replacement therapies include replacement therapies for coagulation disorders, such as Factor VIII and Factor IX for hemophilia A and B; enzyme replacement therapies for lysosomal storage diseases, such as alglucosidase alfa (Myozyme® and Lumizyme®) for Pompe disease; alpha-L-iduronidase for Hurler syndrome; and adenosine deaminase for adult-type adenosine deaminase deficiency.

In some aspects, the antigenic therapy is a gene therapy. Gene therapies typically work by one of the following three mechanisms: (1) by supplying a subject with a healthy copy of a disease-causing gene (as does voretigene neparvovec-rzyl (Luxturna®), for example); (2) by inactivating a disease-causing gene (as may ASOs and siRNA, for example); or (3) by introducing a gene into the body to help treat a disease. Gene therapies include DNA (e.g., antisense oligonucleotides (ASOs)) and/or RNA (e.g., siRNA), which can be delivered to a subject in vivo or ex vivo via a variety of products. In vivo gene delivery products include plasmid DNA, viral vectors (e.g., AAV, such as AAV9) and non-viral vectors, such as bacterial vectors or lipid nanoparticles. Other examples of non-viral vectors suitable for in vivo gene delivery include exosomes, polymeric particles, inorganic particles and lipid-polymer hybrid particles. Ex vivo gene delivery products include subject-derived cellular gene therapy products. Gene therapies also include gene editing technologies, such as CRISPR. Gene editing technologies, such as CRISPR, can conveniently be delivered to a subject via any of the products for in vivo gene delivery described herein. Specific examples of gene therapies include voretigene neparvovec-rzyl (Luxturna®, for retinal dystrophy); and onasemnogene abeparvovec-xioi (Zolgensma®, for pediatric spinal muscular atrophy).

In some aspects, the gene therapy comprises DNA and/or RNA and a viral vector. In some aspects, the viral vector is derived from an adeno-associated virus (AAV), such as a recombinant AAV. In some aspects, the AAV is AAV9. Other examples of viral vectors suitable for use in the context of the present disclosure include viral vectors derived from retrovirus, herpes virus, adenovirus, lentivirus, rabies virus, lentivirus, VSV, poxvirus (e.g., vaccinia virus, variola virus, canarypox), reovirus, semliki forest virus, yellow fever virus, sindbis virus, togavirus, baculovirus, bacteriophages, alphavirus, and flavavirus.

In some aspects, the antigenic therapy is a cellular therapy. An example of a cellular therapy is axicabtagene ciloleucel (Yescarta®, for relapsed or refractory large B-cell lymphoma). Another example of a cellular therapy is CAR-T cells.

Alloantigens, antigens present in some but not all individuals of a species and recognized as foreign by those that lack it, are often the basis for graft rejection reactions. Accordingly, another embodiment is a method of treating graft-versus-host disease in a subject in need thereof, comprising administering to the subject a therapeutically effective amount of compound of the disclosure or composition described herein.

Examples of alloantigens include, but are not limited to, major histocompatability complex (MEW) class I and class II antigens, minor histocompatability antigens, endothelial glycoproteins, such as blood group antigens, and carbohydrate determinants.

Another embodiment is a method for promoting wound healing in a subject in need thereof, comprising administering to the subject a therapeutically effective amount of compound of the disclosure, e.g., in the form of a composition described herein.

In some aspects of any of the methods described herein, the method further comprises administering an antigen, or an immunogenic fragment thereof, to the subject. In some further aspects, the antigen, or an immunogenic fragment thereof, and the compound of the disclosure are co-administered. For example, it is sometimes desired to induce antigen-specific immune tolerance (e.g., when a compound of the disclosure is being administered to immunotolerize a subject to an antigenic therapy). When antigen-specific immune tolerance is desired, the antigen, or an immunogenic fragment thereof, and the compound of the disclosure, e.g., in the form of a composition described herein, are preferably co-administered.

As used herein, "co-administer," "co-administration" and the like refer to simultaneous or nearly simultaneous but sequential administration of two or more agents (e.g., a compound of the disclosure and an antigen) via the same route of administration at the same or nearly the same site on the body of a subject.

When co-administration is simultaneous (e.g., concurrent), a first agent (e.g., a compound of the disclosure) and a second agent (e.g., an additional therapeutic agent, an antigen, or an immunogenic fragment thereof) can be in separate formulations or the same formulation. Alternatively, the first and second agents can be administered sequentially as separate compositions. When co-administration is sequential, administration of subsequent composition(s) occurs within 24 hours of administration of a first composition and, preferably, within 12 hours, for example, within 10 hours, 5 hours, 4 hours, 3 hours, 2 hours, 60 minutes, 30 minutes, 15 minutes, 10 minutes or 5 minutes, of administration of the first composition. Typically, when co-administration is sequential, the administration of subsequent composition(s) follows immediately after completion of administration of the first composition, taking into account any manipulations that a clinician or subject administering the compositions may need to engage in to ready subsequent composition(s) for administration.

When co-administration is oral, the site of administration is the mouth, and the two or more agents being co-administered are administered at the same site, by mouth, whether or not they are given in a single formulation or separate formulations. When co-administration is by injection of two or more compositions, however, the site of administration is more typically nearly the same. In such situations, the anatomical sites of administration are typically less than 2 inches apart from one another, for example, less than about 0.5 inches, less than about 1 inch or less than about 1.5 inches from one another.

In some aspects, an antigen, or an immunogenic fragment thereof, and a compound of the disclosure are co-administered. In further aspects, administration of the antigen, or an immunogenic fragment thereof, precedes administration of the compound of the disclosure. In alternative further aspects, administration of the compound of the disclosure precedes administration of the antigen, or an immunogenic fragment thereof. In yet alternative further aspects, administration of the compound of the disclosure and the antigen, or an immunogenic fragment thereof, is concurrent.

Co-administration can occur by any route of administration described herein. In some aspects, a compound of the disclosure and an antigen, or an immunogenic fragment thereof, are co-administered orally. In some aspects, a compound of the disclosure and an antigen, or an immunogenic fragment thereof, are co-administered subcutaneously.

Without wishing to be bound by any particular theory, it is believed that it is sometimes desirable for a subject's immune system to encounter antigen and compound of the disclosure together, or for the antigen and compound of the disclosure to be "co-presented" to a subject's immune system. When a compound of the disclosure is co-administered with an antigen and the antigen is a protein, such as a protein replacement therapy, co-administration, as, for example, by injection of separate formulations of antigen and compound of the disclosure, is expected to provide for effective co-presentation of the compound of the disclosure and the antigen to a subject's immune system. In such applications, the compound of the disclosure may, but need not be, incorporated into a lipid particle. In preferred aspects of such applications, co-administration is subcutaneous, e.g., by injection. In applications involving delivery of a gene therapy (e.g., a gene therapy comprising DNA and/or RNA), it may be desirable, in order to promote effective co-presentation of the gene therapy and the compound of the disclosure to a subject's immune system, to formulate the gene therapy and the compound of the disclosure into lipid particles comprising the gene therapy and the compound of the disclosure. In preferred aspects, such particles are formulated for oral and/or parenteral (e.g., subcutaneous, intramuscular, intravenous, intradermal) administration, e.g., as by injection.

Also without wishing to be bound by any particular theory, it is believed that particular compounds of the disclosure identified herein embed in a liposome. Use of such compounds, e.g., in accordance with the methods disclosed herein, may be advantageous in aspects wherein effective co-presentation of the compound of the disclosure and the antigen to the subject's immune system is promoted by incorporation of compound of the disclosure and antigen into a lipid particle comprising the compound of the disclosure and the antigen.

A compound of the disclosure can also be administered in combination with one or more non-antigenic therapies to treat a disease, disorder or condition. When administered "in combination" with such non-antigenic therapies, the compound of the disclosure can be administered before, after or concurrently with the other therapy(ies) (e.g., additional therapeutic agent(s)). When administered simultaneously (e.g., concurrently), the compound of the disclosure and another therapy can be in separate formulations or the same formulation. Alternatively, the compound of the disclosure and another therapy can be administered sequentially, either at approximately the same time or at different times, as separate compositions. When the compound of the disclosure and the other therapy (e.g., therapeutic agent) are administered as separate formulations or compositions, the compound of the disclosure and the other therapy can be administered by the same route of administration or by different routes of administration. A skilled clinician can determine appropriate timing for administration of each therapy being used in combination (e.g., timing sufficient to allow an overlap of the pharmaceutical effects of the therapies). Typically, a combination therapy will provide beneficial effects of the drug combination in treating the diseases, conditions or disorders described herein.

In some aspects, a method described herein further comprises administering to the subject (e.g., a therapeutically effective amount of) an additional, non-antigenic therapy(ies), e.g., in combination with a compound of the disclosure or composition described herein. In some aspects, the compound of the disclosure or composition described herein is administered before the additional therapy(ies). In some aspects, the compound of the disclosure or composition described herein is administered after the additional therapy (ies). In some aspects, the compound of the disclosure or composition described herein is administered concurrently with the additional therapy(ies).

A therapeutically effective amount of an agent to be administered can be determined by a clinician of ordinary skill using the guidance provided herein and other methods known in the art. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

A compound of the disclosure, composition described herein, antigen or other therapeutic agent can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound, antigen and/or therapeutic agent, respectively, and the particular disease to be treated. Administration can be local or systemic as indicated. The preferred mode of administration can vary depending on the particular compound or agent.

In some aspects, administration (e.g., of a compound of the disclosure or composition described herein and/or an antigen) is oral. In some aspects, administration (e.g., of a compound of the disclosure or composition described herein and/or an antigen) is intravenous. In some aspects, administration (e.g., of a compound of the disclosure or composition described herein and/or an antigen) is subcutaneous.

A compound of the disclosure or composition described herein can be administered, in accordance with the methods disclosed herein, prophylactically, as when a subject with no known immune intolerance to an antigenic therapy is co-administered a compound of the disclosure or composition described herein with the antigenic therapy. A compound of the disclosure or composition described herein can also or alternatively be administered, in accordance with the methods disclosed herein, therapeutically, as when a subject has demonstrated immune intolerance to an antigen (e.g., an allergic reaction, graft rejection). Accordingly, in some aspects, a subject has no known immune intolerance to an antigen, for example, because the subject is naïve to the antigen. In some aspects, a subject has no known immune intolerance to an antigen after having been administered and/or exposed to the antigen. In some aspects, a subject is immune intolerant to an antigen, for example, developed immune intolerance after having been administered and/or exposed to the antigen or is inherently immune intolerant to the antigen.

The methods described herein are intended to reduce immune intolerance to an antigen for an extended period of time, for example, a period of time necessary to treat a disease, disorder or condition with an antigenic therapy described herein, for life of a subject. Accordingly, in some aspects of the methods described herein, the method further comprises administering the antigen, or an immunogenic fragment thereof (e.g., antigenic therapy, such as a therapeutically effective amount of the antigenic therapy), to the subject in the absence of the compound of the disclosure or composition described herein.

However, a subject's immune intolerance may increase over time following a method described herein, e.g., following subsequent exposure(s) to the antigen. In such cases, the methods described herein can be repeated, for example, as a "booster" vaccine is repeated, to re-immunotolerize the subject to the antigen.

A compound of the disclosure or other therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. In some embodiments, administration (e.g., of a compound of the disclosure) is oral. In some embodiments, administration (e.g., of a compound of the disclosure) is intravenous. The preferred mode of administration can vary depending on the particular compound or agent. Typically, a compound of the disclosure or other therapeutic agent will be administered from about 1 to about 6 (e.g., 1, 2, 3, 4, 5 or 6) times per day, also or alternatively, as an infusion (e.g., a continuous infusion). In some aspects, the administration (e.g., of a compound of the disclosure) is QD or BID (e.g., QD)). In some aspects, the administration (e.g., of a compound of the disclosure) is daily.

Orally administered liposomes, such as those described herein, can reach the lymph node, and colocalize with immune cells, including B-cell and T-cells, in the lymph node. Accordingly, also provided herein is a method of delivering a therapeutic agent (e.g., a compound of the disclosure) to a lymph node of a subject (e.g., a subject in need thereof), comprising orally administering to the subject a therapeutically effective amount of a composition comprising a plurality of lipid particles (e.g., solid lipid particles), wherein each lipid particle comprises at least one phospholipid (e.g., a phospholipid containing a $C_4$-$C_{30}$ acyl chain, such as a saturated $C_4$-$C_{30}$ acyl chain, as in dimyristoylphosphatidylcholine (DMPC)) and a therapeutic agent that can embed in a lipid bilayer of the lipid particle (e.g., a compound of the disclosure).

A compound of the disclosure or other therapeutic agent can be administered in a dosage ranging from about 0.001 mg/kg to about 100 mg/kg of body weight or, alternatively, in a dosage ranging from about 1 mg/dose to about 5,000 mg/dose, every 4 to 120 hours, or according to the requirements of the particular agent. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. In some aspects, a suitable dosage (e.g., daily dosage) is from about 0.1 mg/kg to about 10 mg/kg, e.g., from about 0.1 mg/kg to about 5 mg/kg, from about 0.1 mg/kg to about 2.5 mg/kg or about 0.2 mg/kg to about 2.4 mg/kg, body weight per treatment. Suitable dosages can be from about 0.001 mg/dose to about 100 mg/dose, from about 0.01 mg/dose to about 100 mg/dose, from about 0.1 mg/dose to about 50 mg/dose, from about 0.1 mg/dose to about 10 mg/dose, from about 0.5 mg/dose to about 50 mg/dose, from about 1 mg/dose to about 10,000 mg/dose, from about 1 mg/dose to about 7,500 mg/dose, from about 1 mg/dose to about 5,000 mg/dose, from about 10 mg/dose to about 2,500 mg/dose or from about 100 mg/dose to about 1,000 mg/dose. In some aspects, a suitable dosage (e.g., daily dosage) is from about 10 mg/dose to about 1,000 mg/dose, e.g., from about 15 mg/dose to about 1,000 mg/dose, from about 10 mg/dose to about 500 mg/dose, from about 10 mg/dose to about 250 mg/dose, from about 15 mg/dose to about 150 mg/dose, about 15 mg/dose, about 30 mg/dose, about 50 mg/dose, about 100 mg/dose, about 125 mg/dose or about 150 mg/dose.

Doses lower or higher than those recited above may be required. Specific dosage and treatment regimens for any particular patient will depend, for example, upon a variety of factors, such as the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. Determining the dosage for a particular agent, subject and disease, disorder or condition is within the abilities of one of skill in the art.

EXEMPLIFICATION

Example 1. Design of TIM Agonists

A co-crystal structure of dicaproyl phosphatidylserine (PS) bound to TIM4 was published in 2007, as was an "apo" structure of TIM4 in the presence of a high concentration of tartaric acid as precipitant in the same publication. Described herein are compounds designed to mimic PS, an endogenous ligand for the TIM-4 receptor that induces an agonistic effect.

To guide design of the compounds, a co-crystal structure of dicaproyl PS bound to TIM4 was used to define the "active" 3D conformation of the metal-ion-dependent ligand-binding site (MILIBS), and key interactions between the ligand and the MILIBS site. Docking was used to calculate the binding affinities of the compounds for TIM4.

In preparation for docking, the x-ray crystallographic protein structure (PDB ID: 3BIB) was downloaded from the PDB database. The endogenous ligand bound to the protein, phosphatidylserine (PS), was removed from the binding site. All water molecules were removed except one that is in the binding site and forming a bridge between PS and the protein through hydrogen bond interactions. Charges were calculated for all atoms in the protein at physiologic pH (7.4) which is the same pH that is used in in vitro experiments for measuring binding affinities. Charges for atoms in all docked molecules were calculated at physiologic pH as well. The docking method was validated by re-docking PS into its binding site. Both rigid and flexible docking were performed for all molecules and the top 20 binding poses were identified.

To validate the docking method, the endogenous ligand, PS, which had previously been removed from the protein complex, was re-docked into the binding site. The pose that is closest to the correct (native) pose had an RMSD of 2.213 Å and was identified among the top 11 poses. The binding affinity of PS to its protein was calculated computationally through docking and was 6.0 kcal/mol.

To calculate the binding affinities of the proposed compounds for TIM4, the proposed structures were docked. The proposed structures, as well as the range of the binding affinity values for the top 20 binding poses obtained for the proposed structures using rigid (and flexible) docking are listed in Table 1.

TABLE 1

| Compound No. | Compound Structure | Rigid (Flexible) Docking Score Range |
|---|---|---|
| PS | (phosphatidylserine structure with acetyl, hexanoyl esters, phosphate, and L-serine group) | −6.0−−5.1 (−5.9−−4.9) |
| 1 | (benzyloxy-phenyl-acetamido-L-2,3-diaminopropanoic acid) | −7.6−−6.1 (−8.2−−5.2) |
| 2 | (1-naphthylmethoxy-phenyl-acetamido-L-2,3-diaminopropanoic acid) CLogP: 1.2872 LogS: −2.852 | −8.2−−6.2 (−8.6−−7.0) |
| 3 | (diphenylmethoxy-phenyl-acetamido-L-2,3-diaminopropanoic acid) | −7.8−−6.0 (−8.7−−5.9) |
| 4 | (2-naphthylmethoxy-phenyl-acetamido-L-2,3-diaminopropanoic acid) CLogP: 1.2872 LogS: −2.85 | −8.2−−6.4 (−9.3−−7.2) |
| 5 | (2,3-dihydrobenzo[1,4]dioxin-5-ylmethoxy-phenyl-acetamido-L-2,3-diaminopropanoic acid) CLogP: 0.0371993 LogS: −1.602 | −7.5−−6.2 (−7.6−−5.6) |

TABLE 1-continued

| Compound No. | Compound Structure | Rigid (Flexible) Docking Score Range |
|---|---|---|
| 6 | CLogP: −0.209801<br>LogS: −2.013 | −8.0−−6.4<br>(−8.7−−6.5) |
| 7 | CLogP: 1.2872<br>LogS: −2.849 | −8.5−−6.7<br>(−8.8−−7.5) |
| 8 | CLogP: 0.291199<br>LogS: −2.03 | −8.2−−6.4<br>(−8.9−−6.6) |
| 9 | CLogP: 0.707199<br>LogS: −2.097 | −8.1−−6.7<br>(−8.6−−7.0) |
| 10 | CLogP: −0.463801<br>LogS: −1.653 | −7.7−−6.4<br>(−8.6−−5.6) |

The docking model showed the polar groups of Compound 2 aligned as well as the natural ligand, and formed similar interactions with the protein's binding site as did the natural ligand, PS.

Example 2. In Vitro Dose-Response Analysis of Compounds 1-3 in Murine T-Cells

All animal studies were conducted under IACUC number B2020-91 and in compliance with Tufts University/Tufts Medical Center & Human Nutrition Research Center on Aging. Animals were housed four in a cage and had access to food and water ad libitum. Anti-FoxP3 and anti-CD4 for flow cytometry were obtained from eBioscience. Compounds 1-3 were formulated with 10% DMPC in PBS. PS liposomes were synthesized at a 30:70 PS:lipid molar ratio.

Splenocytes from naïve C57BL/6 mice were stained with CFSE, seeded at $2\times10^5$ cells/well, and dosed with each compound from 1e-4 μM to 3.0e-9 μM using a log 2 dilution scheme. Cells were incubated for 72 hours before phenotyping for FoxP3+/CD4+ T-cells. Flow cytometer analysis was performed to assess changes in percent FoxP3+/CD4+

T-cells as a function of compound and dose. Concentration versus response was fitted to a 4-parameter, log-logistic model using the "drc" package in "R". Both $EC_{50}$ and $EC_{90}$ were obtained by model fitting.

Cells were observed via a microscope at the end of the incubation period. All cells looked healthy and suitable for flow cytometry analysis.

Visual inspection of the model fit suggested that a 4-parameter dose-response model was sufficient to capture the data for the tested compounds. FIG. 1 shows the resulting model fit of the data to a 4-parameter dose-response model. Table 2 summarizes $EC_{50}$ and $EC_{90}$ values obtained from the model fitting.

TABLE 2

Summary of Model Obtained $EC_{50}$ and $EC_{90}$ Values by Treatment:

| Treatment | EC50 mean (SE) µM | EC90 mean (SE) µM |
|---|---|---|
| Compound 3 | $3.76E^{-3}$ ($1.71E^{-2}$) | $2.04E^{-2}$ ($1.07E^{-1}$) |
| Compound 1 | $2.06E^{-3}$ ($9.91E^{-3}$) | $6.88E^{-1}$ (5.81) |
| Compound 2 | $6.02E^{-6}$ ($1.62E^{-6}$) | $1.99E^{-5}$ ($7.34E^{-6}$) |
| PS | $1.33E^{-4}$ ($3.62E^{-5}$) | $3.14E^{-4}$ ($1.94E^{-4}$) |

Lower and upper plateau values for the percent FoxP3+/CD4+ T-cells as a function of increasing doses of each compound were obtained from model fitting. The mean FoxP3+/CD4+ T-cells value increased from 1.32% (0.12), 1.47% (0.49), 2.20% (0.18) and 1.92% (0.10) mean (SEM) for low dose Compound 3, Compound 1, Compound 2 and PS liposomes, respectively, to 3.48% (153), 5.18% (4.36), 4.54 (0.14) and 4.87 (0.53) mean (SEM) for high dose Compound 3, Compound 1, Compound 2 and PS liposomes, respectively.

Compounds 1-3 resulted in a dose-dependent increase in FoxP3+/CD4+ T-cells, although only Compound 2 showed a clear plateau. Treatment with PS liposomes also resulted in a clear plateau, but the potency of Compound 3, as measured by $EC_{50}$ and $EC_{90}$, was two and one orders of magnitude higher (more potent) than PS, respectively. This is in line with the results of the molecular modeling described in Example 1, which showed that Compound 2 had the lowest docking score of Compounds 1-3, while Compounds 1 and 3 had docking scores that were closer to that of PS.

The increased potency and aqueous solubility of Compound 3 compared to PS makes it attractive.

Example 3. Dose Pharmacodynamics of Compound 2 after a Single Ascending Oral Dose in Mice In this study, the pharmacodynamic (PD) effects of a single SC dose of Compound 2 in mice after 5 days of dosing were evaluated.

All animal studies were conducted under IACUC number B2020-91 and in compliance with Tufts University/Tufts Medical Center & Human Nutrition Research Center on Aging. Animals were housed 4 per cage and had access to food and water ad libitum. Compound 2 was formulated with 10% DMSO in PBS buffer.

Figure 2A:
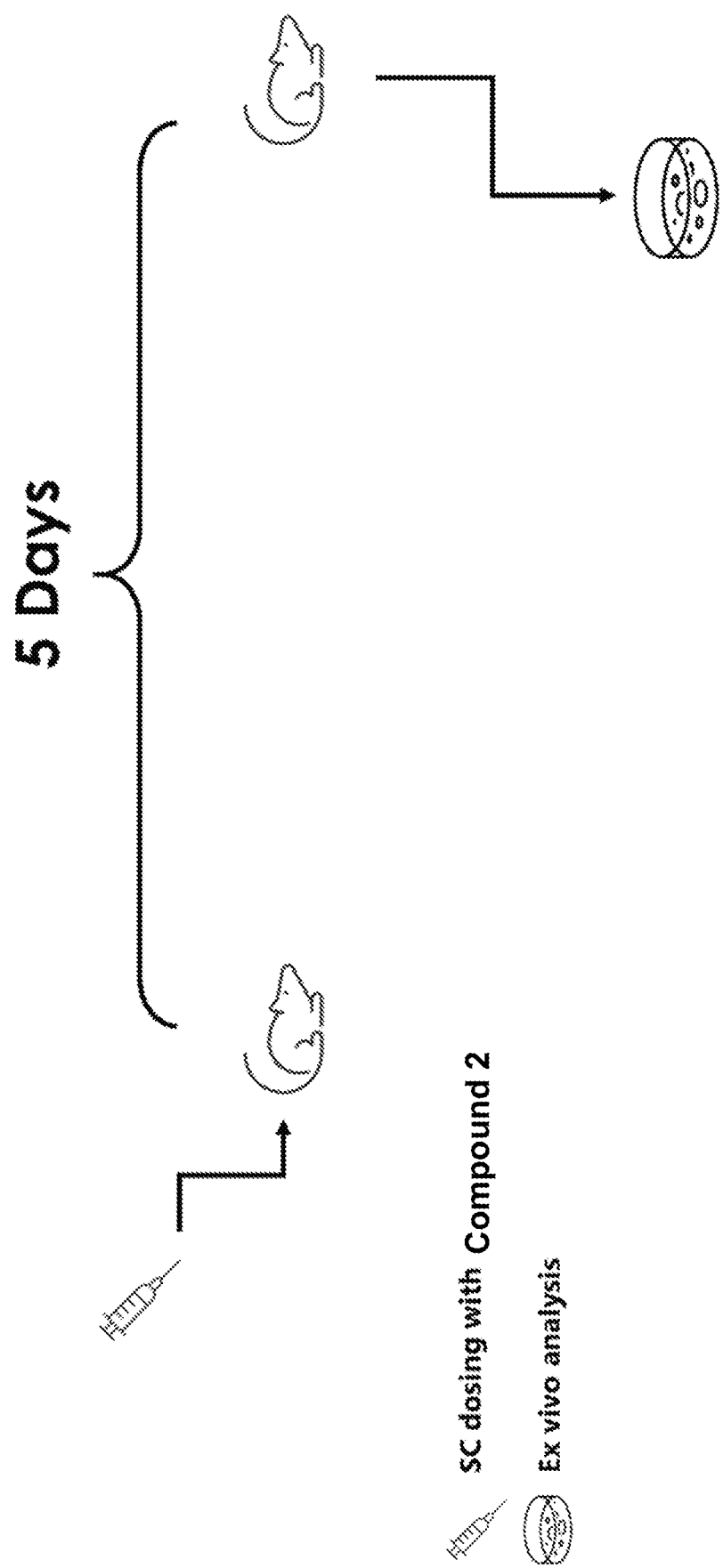
FIG. 2A is a diagram of the study described in Example 3.

This study was designed to evaluate the PD effects of a single dose of Compound 2 in mice. Animals were administered a single oral gavage, as per their group assignment. Details about the dosing groups are listed in Table 3. Five days after the oral dose, animals were sacrificed, and their spleens were collected for T-cell phenotyping. FIG. 2A is a schematic diagram of the study design.

TABLE 3

| Dosing groups | | | |
|---|---|---|---|
| | Dose, µg/mouse SC | Volume, µl | n |
| Compound 2 | 100 | 100 | 3 |
| | 30 | 100 | 3 |
| | 10 | 100 | 6 |
| | 1 | 100 | 3 |
| | 0.1 | 100 | 3 |
| | 0.01 | 100 | 3 |

For ex vivo analysis, spleens were collected for splenocyte analysis, and prepared into a single-cell suspension for cellular phenotyping by flow cytometry. Cells were stained and gated for CD4. Percent FoxP3+/CD4+ T-cells and percent FoxP3+/NRP1+ were evaluated using flow cytometry. For dose-response analysis, dose versus response was fitted to 4- and 5-parameters, log-logistic models using the "drc" package in "R". Both $EC_{50}$ and $EC_{90}$ were obtained by model fitting.

Figure 2B:
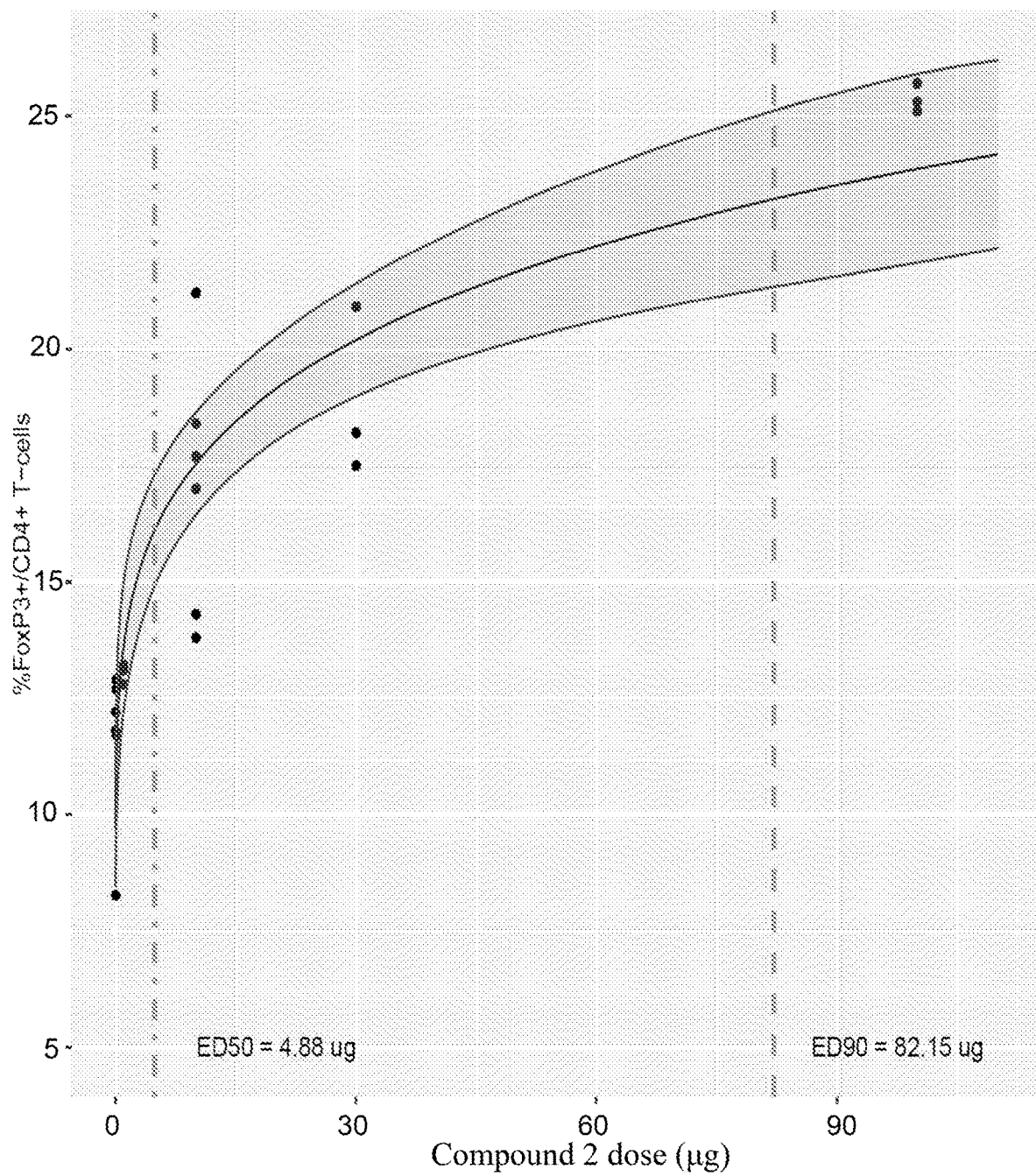
FIG. 2B shows the in vivo Compound 2 dose-response relationship for FoxP3+/CD4+ $T_{regs}$.

The percent of FoxP3+/CD4+ T-cells increased in a dose-dependent manner from a mean value of 10.7% (SD=2.2) in the lowest dose group to 25.4% (SD=0.31) in the highest dose group. The data were fitted to a four-parameter dose-response model. $ED_{50}$ was estimated at 4.88 µg, and $ED_{90}$ was estimated at 82.1 µg. FIG. 2B shows the dose-PD model fit and the associated confidence interval around the mean model predicted dose-PD. Overall, the model was able to capture the data well. Both $ED_{50}$ and $ED_{90}$ values are also shown in FIG. 2B.

Figure 2C:
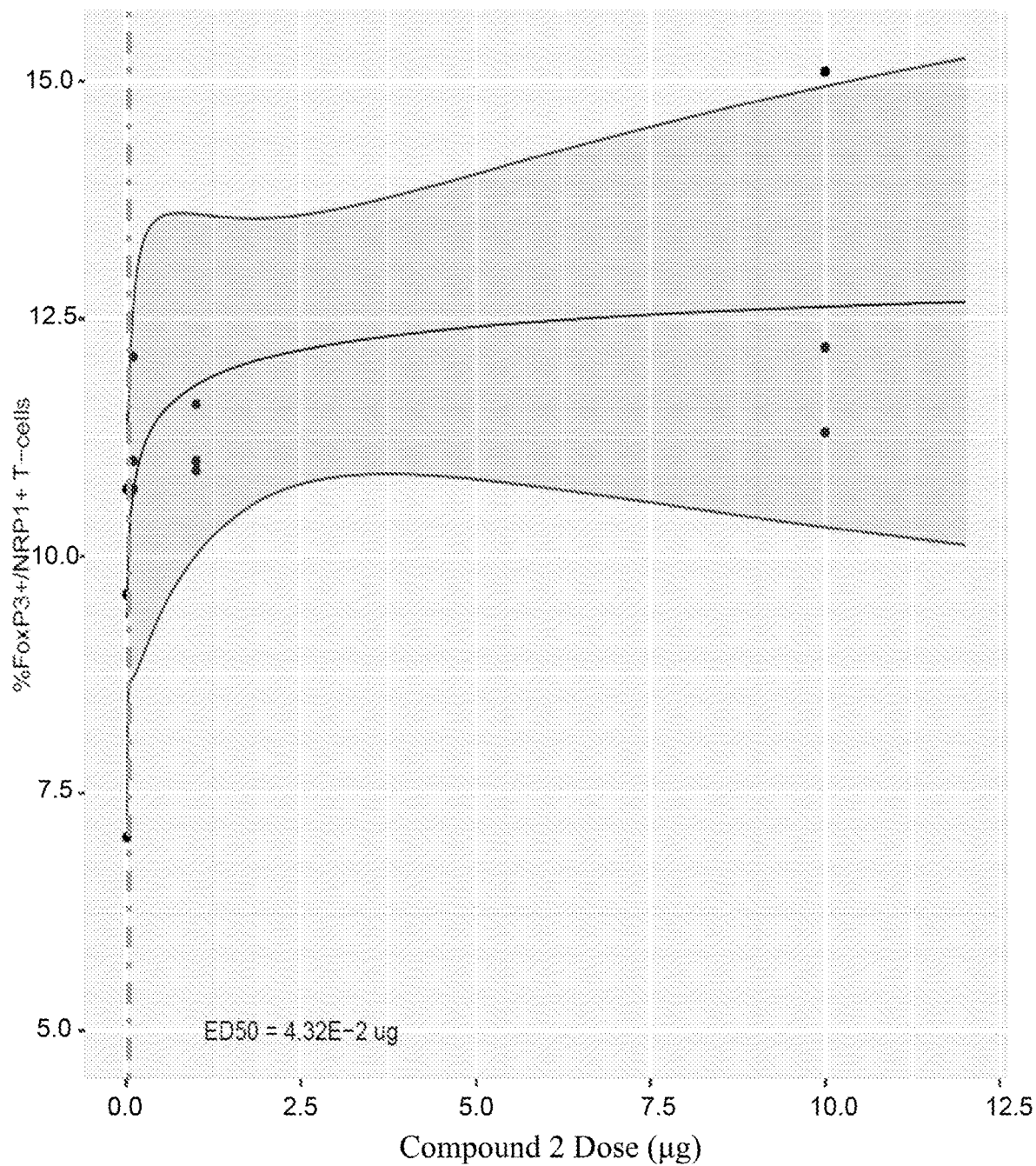
FIG. 2C shows the in vivo Compound 2 dose-response relationship for FoxP3+/NRP1+CD4+$T_{regs}$.

FoxP3+/CD4+ T-cell population was further analyzed for neuropilin-1 (NRP1) expression. Several reports correlate NRP1 expression on T-cells with a state of immune tolerance. Expression of NRP1 was observed at the low doses of Compound 2; this was almost a binary response, with $ED_{50}$ estimated at 4.32E' µg (FIG. 2C).

Data from this study support the hypothesis that Compound 2 can induce a tolerogenic immune response in a dose-dependent manner. The number of FoxP3+/CD4+ T-cells (T-reg) increased by 150% from the lowest dose to the highest dose group. Without wishing to be bound by any particular theory, it is believed that an increase above 100% (e.g., a doubling of FoxP3+/CD4+ T-cells) will increase tolerance toward a target antigen. Accordingly, it is believed that repeat dosing of Compound 2 at its $ED_{50}$ value would be sufficient for tolerance induction.

Example 4. Therapeutic Effects of Compound 2 in $MOG_{35-55}$-Induced Murine EAE Model Versus Standards of Care Anti-Alpha4 mAb and Glatiramer Acetate Multiple sclerosis is a chronic, often disabling, disease of the human central nervous system (CNS). Loss of tolerance to the myelin sheath causes the immune system to attack it and results in the clinical manifestation of the disease. This is mediated by pathogenic auto-reactive T-cells recognizing self-antigenic peptides in complex with major histocompatibility complex (MHC) molecules. There is no known cure for MS, however, blocking the ability of auto-reactive T-cells from entering the CNS proved to be an effective treatment option to ameliorate MS symptoms. Anti-α4 mAbs, such as Tysabri, have been approved for the management of MS, as has been glatiramer acetate. Other treatment options rely on generalized immune suppressive agents such as steroids.

Addressing the presence of auto-reactive T-cells and inducing a shift to higher tolerogenic T-cells may provide potentially curative therapy to MS. Compound 2 is a proposed T-cell immunoglobulin mucin protein family of receptors (TIM) agonist that can induce tolerogenic T-cells. TIM plays a key role in adaptive and innate immune response and has been associated with the regulation of autoimmunity and cancer. Several ligands are known to bind to TIM, including PS.

The affinity of PS to different members in the TIM family varies substantially, with TIM3 having a lower affinity to PS than TIM4. However, all anti-TIM3 antibodies that have shown any functional efficacy in vivo and in vitro interfere with TIM3 binding to PS, suggesting that PS-TIM3 interaction is key in the TIM3 function, even at lower affinity.

The tolerogenic potential of PS has been exploited by tumors. For example, PS in the human ovarian tumor microenvironment can induce T cell signaling arrest. Furthermore, the PS-mediated T cell arrest was blocked with anti-PS antibodies. Collectively, published data on TIM and its role in immune tolerance suggest TIM as a potential target for the treatment of autoimmune disorders.

This study evaluates the effects of Compound 2, a TIM agonist, on disease progression versus standards of care anti-alpha4 mAbs and glatiramer acetate. Furthermore, the study evaluates dose-response of Compound 2, and the effects of switching from anti-alpha4 mAbs treatment to treatment with Compound 2 in an experimental autoimmune (allergic) encephalomyelitis (EAE).

All animal studies were conducted under IACUC number B2020-91 and in compliance with Tufts University/Tufts Medical Center & Human Nutrition Research Center on Aging. Animals were housed at designated facilities within Tufts University-Tufts Medical Center & Human Nutrition Research Center on Aging. Animals were housed four in a cage and have access to food and water ad libitum.

Materials and reagents are provided in Table 4.

TABLE 4

| Materials and Reagents | |
| --- | --- |
| Mice C57/BL6 | CRL |
| $MOG_{35-55}$ | R&D |
| Complete Freund's Adjuvant (CFA) | Thermo Fisher Scientific, Waltham, MA |
| Pertussis Toxin (PT) | |

Experimental autoimmune (allergic) encephalomyelitis (EAE) is considered the best non-clinical model of multiple sclerosis (MS). EAE is characterized by immune responses against CNS tissue and can be induced in animals by immunizing them against proteins of the CNS. In the active EAE model, mice are immunized with $MOG_{35-55}$ peptide emulsified in Complete Freund's Adjuvant (CFA) by subcutaneous injection at the tail base (0.1 mL of emulsion/mouse) under anesthesia. On the day of injection (Day 0) and 2 days later, mice receive an intraperitoneal injection of Pertussis Toxin (PT) in PBS at 600 ng/mouse/dose (0.1 mL).

Symptoms typically develop in mice 9-14 days after immunization (Day 0). Daily observation and scoring of mice start on Day 9 and continue until the end of the study. Table 5 details the expected clinical symptoms and the scoring criteria used in this study.

TABLE 5

| Mouse EAE Clinical Symptoms and Scoring Criteria | |
| --- | --- |
| Score | Clinical observations |
| 0.0 | No obvious changes in motor function compared to non-immunized mice: When picked up by the base of the tail, the tail has tension and is erect. Hind legs are usually spread apart. When the mouse is walking, there is no gait or head tilting. |
| 0.5 | Tip of the tail is limp: When picked up by the base of the tail, the tail has tension except for the tip. Muscle straining is felt in the tail, while the tail continues to move. |
| 1.0 | Limp tail: When picked up by the base of the tail, instead of being erect, the whole tail drapes over one's finger. Hind legs are usually spread apart. No signs of tail movement are observed. |
| 1.5 | Limp tail and hind leg inhibition: When picked up by the base of the tail, the whole tail drapes over one's finger. When the mouse is dropped on a wire rack, at least one hind leg falls through consistently. Walking is very slightly wobbly. |
| 2.0 | Limp tail and weakness of hind legs: a) When picked up by the base of the tail, the legs are not spread apart but held closely together. When the mouse is observed walking, it has a clearly apparent wobbly walk. One foot may have toes dragging, but the other leg has no apparent inhibitions of movement. Or, b) Mouse appears to be at a score 0.0, but there are obvious signs of head tilting when the walk is observed. The balance is poor. |
| 2.5 | Limp tail and dragging of hind legs: a) Both hind legs have some movement, but both are dragging at the feet (mouse trips on hind feet). Or b) No movement in one leg/completely dragging one leg, but movement in the other leg. Or c) EAE severity appears mild when picked up (as score 0.0-1.5), but there is a strong head tilt that causes the mouse to occasionally fall over. |
| 3.0 | a) Limp tail and complete paralysis of hind legs (most common). Or b) Limp tail and almost complete paralysis of hind legs. One or both hind legs are able to paddle, but neither hind leg is able to move forward of the hind hip. Or c) Limp tail with paralysis of one front and one hind leg. Or d) ALL of the severe head tilting, Walking only along the edges of the cage, Pushing against the cage wall, Spinning when picked up by the base of the tail. |
| 3.5 | Limp tail and complete paralysis of hind legs. In addition: The mouse is moving around the cage, but when placed on its side, is unable to right itself. Hind legs are together on one side of the body. Or b) Mouse is moving around the cage, but the hindquarters are flat like a pancake, giving the appearance of a hump in the front quarters of the mouse. |

TABLE 5-continued

Mouse EAE Clinical Symptoms and Scoring Criteria

| Score | Clinical observations |
|---|---|
| 4.0 | Limp tail, complete hind leg, and partial front leg paralysis: Mouse is minimally moving around the cage but appears alert and feeding.<br>Often euthanasia is recommended after the mouse scores 4.0 for 2 days. However, with daily s.c. fluids most C57BL/6 mice may recover to 3.5 or 3.0, while SJL mice may fully recover even if they reach a score of 4.0 at the peak of disease. When the mouse is euthanized because of severe paralysis, a score of 5.0 is entered for that mouse for the rest of the experiment. |
| 4.5 | Complete hind and partial front leg paralysis, no movement around the cage. The mouse is not alert.<br>The mouse has minimal movement in the front legs. The mouse barely responds to contact.<br>Euthanasia is recommended. When the mouse is euthanized because of severe paralysis, a score of 5.0 is entered for that mouse for the rest of the experiment. |
| 5.0 | The mouse is spontaneously rolling in the cage (euthanasia is recommended). |

Figure 3A:
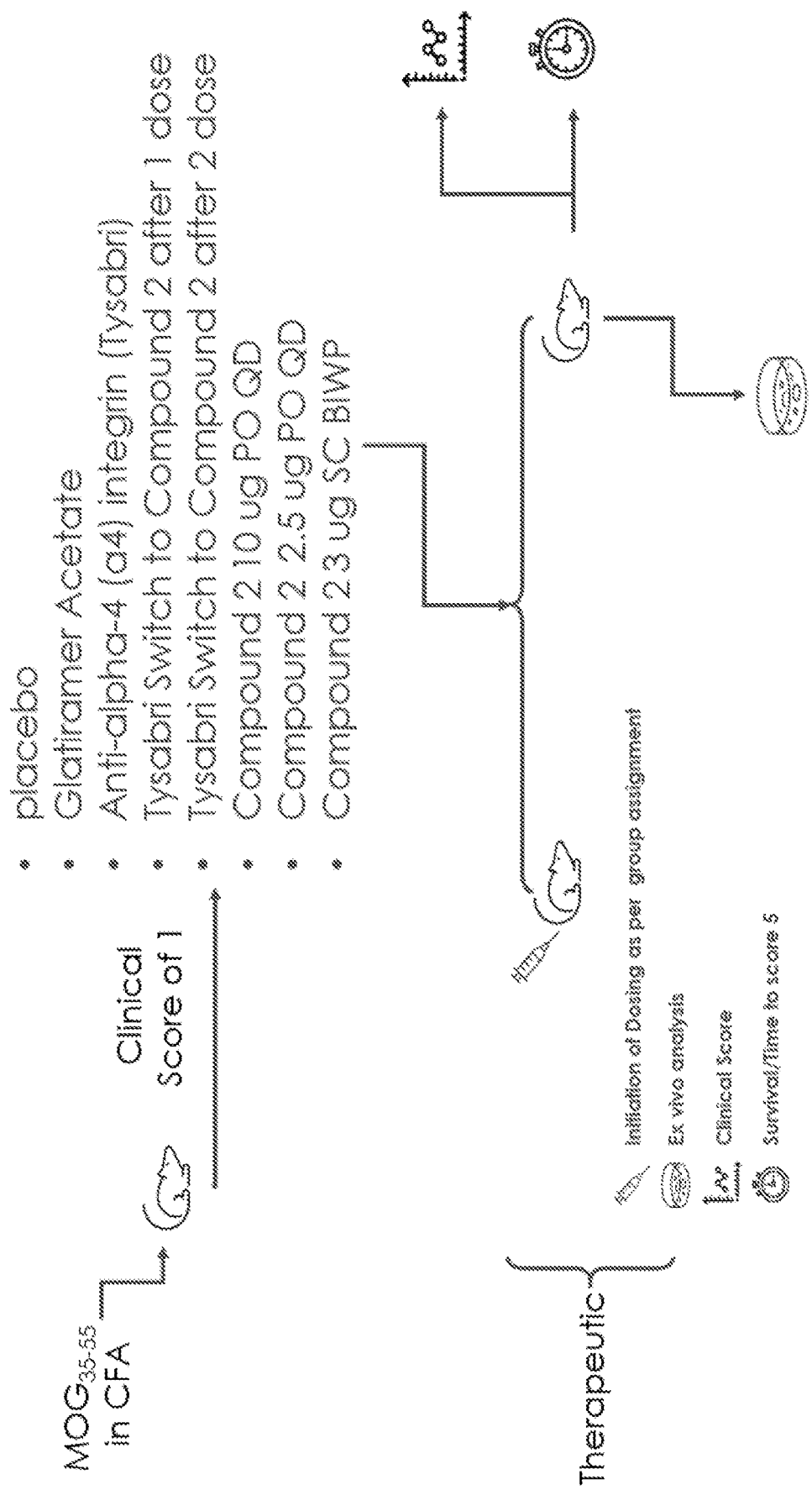
FIG. 3A is a diagram of the study described in Example 4.

FIG. 3A shows an outline of the study. To evaluate the therapeutic effects of Compound 2, treatment was initiated after the first clinical symptoms were observed. Once a mouse had a clinical score of 1, it was randomized to a treatment group listed in FIG. 3A or to receive placebo by random sampling algorithm. The treatment groups are listed in Table 6. Mice in all groups were monitored and scored daily for clinical symptoms.

TABLE 6

Treatment Groups

| Group | Treatment | Note(s) |
|---|---|---|
| 1 | Control | |
| 2 | Glatiramer Acetate | 0.2 mg/mouse/day subcutaneously |
| 3 | Anti-alpha-4 (α4) integrin (Tysabri) | 2 doses of 1.5 mg/mouse on the day of disease onset and 1.5 mg/mouse on day 3 after disease onset |
| 4 | Anti-alpha-4 (α4) integrin (Tysabri) switch 1 | One dose of 1 mg/kg each on the day of disease onset, then switch to Compound 2 10 µg/day orally |
| 5 | Anti-alpha-4 (α4) integrin (Tysabri) switch 2 | 2 doses of 1.5 mg/mouse on the day of disease onset and 1.5 mg/mouse on day 3 after disease onset, then switch to Compound 2 10 µg/day orally |
| 6 | Compound 2, 10 µg PO QD | Compound 2 10 µg/day orally |
| 7 | Compound 2, 2.5 µg PO QD | Compound 2 2.5 µg/day orally |
| 8 | Compound 2, 3 µg SC BIW | Compound 2 3 µg twice a week subcutaneously |

At the end of the study, spleens were collected from a representative sample of mice from each group for splenocyte analysis. A single-cell suspension was prepared for cellular phenotyping by flow cytometry. Cells were stained and gated for CD4$^+$T-cells. Percent FoxP3$^+$/CD4$^+$ T-cells were evaluated by flow cytometry.

Figure 3B:
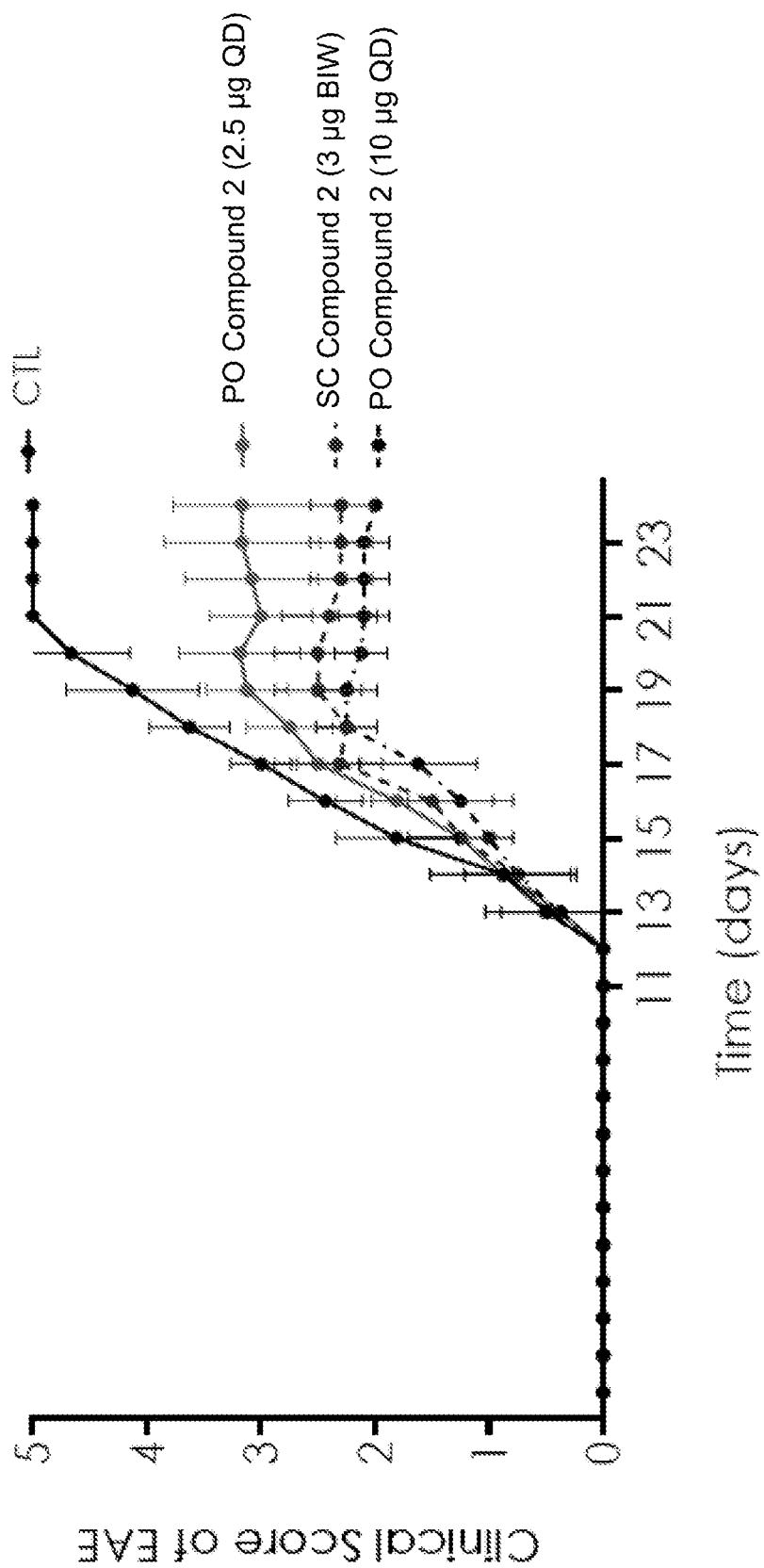
FIG. 3B shows the mean clinical score of mice treated with the indicated doses of Compound 2 in the murine EAE model described in Example 4.
Figure 3C:
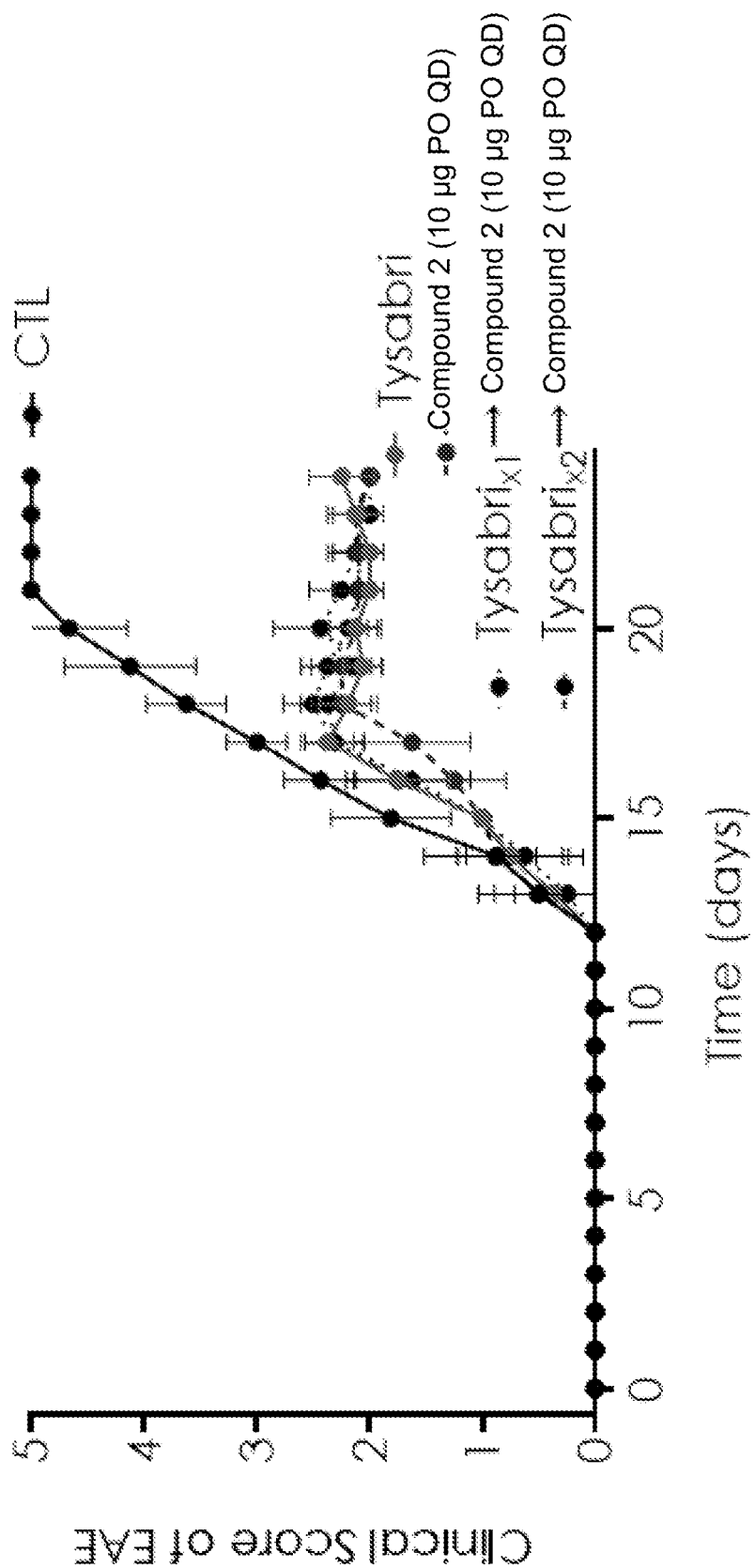
FIG. 3C shows the mean clinical score of mice treated with a full regimen of anti-alpha4 integrin, 10 μg Compound 2 PO QD, or one or two doses of anti-alpha4 integrin followed by 10 μg Compound 2 PO QD in the murine EAE model described in Example 4.
Figure 3D:
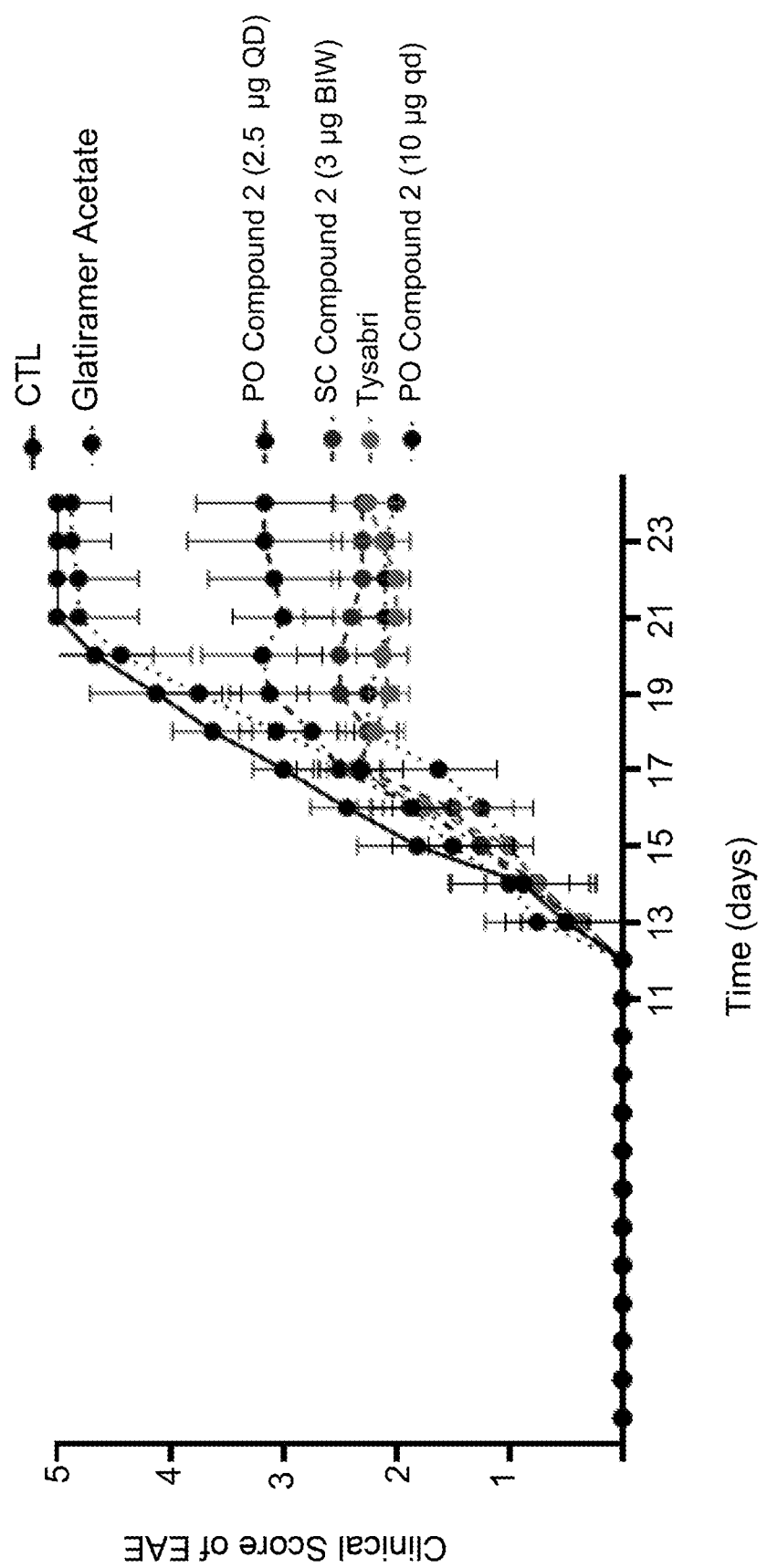
FIG. 3D shows the mean clinical score of mice treated with glatiramer acetate, anti-alpha4 integrin, or the indicated dose of Compound 2 in the murine EAE model described in Example 4.

FIG. 3B shows that Compound 2 reduced the MS clinical score after disease onset in a dose-dependent manner. FIG. 3C shows that a daily 10-µg oral dose of Compound 2 was as effective as a full regimen of anti-alpha4 integrin, corresponding to Tysabri, the third-line drug used for severe MS, in controlling MS symptoms after disease onset in the murine EAE model. Switching from anti-alpha4integrin to a 10-µg oral dose of Compound 2 following one or two injections of anti-alpha4 integrin also resulted in disease control after disease onset. FIG. 3D shows that all Compound 2 doses and regimens were more effective than glatiramer acetate, the FDA-approved first-line treatment for mild MS, in controlling MS symptoms after disease onset.

Example 5. Syntheses of Compounds 1-3

Compound 1 HCl, (S)-2-amino-3-(2-(4-(benzyloxy)phenyl)acetamido)propanoic acid, hydrochloride salt, was synthesized according to the following synthetic route:

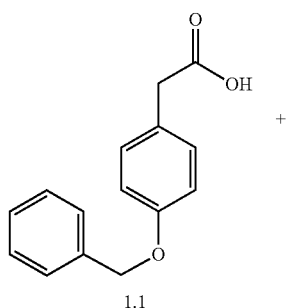

1.1

+

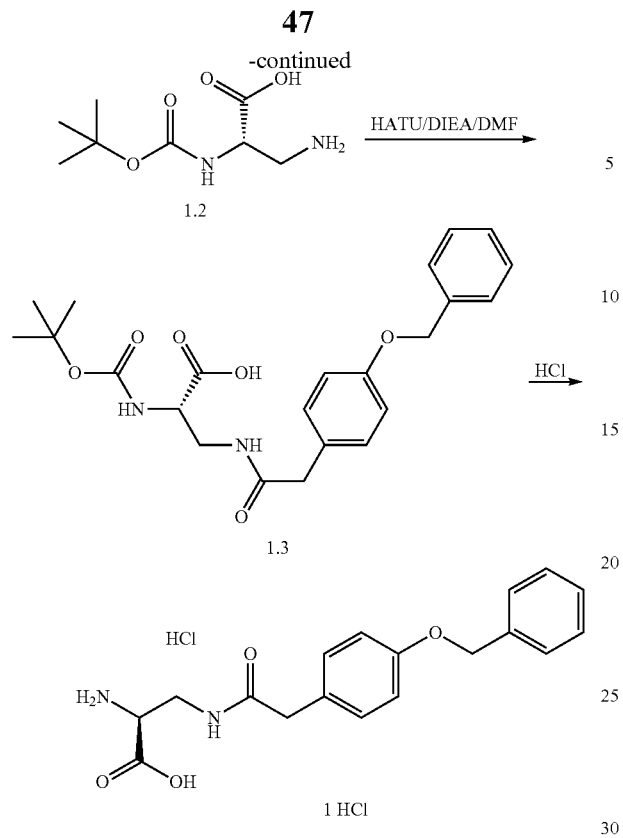

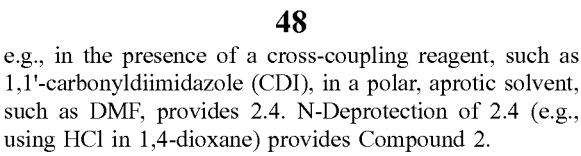

(S)-3-(2-(4-(Benzyloxy)phenyl)acetamido)-2-((tert-butoxycarbonyl)amino)propanoic acid 1.3. To a solution of benzylphenylacetic acid derivative 1.1 (0.60 g) in DMF (6 mL) were added DIEA (0.95 mL) and HATU (0.99 g). The reaction mixture was stirred at RT for 15 minutes. Then, Boc-Dap-OH (1.2, 0.506 g) was added, and the reaction mixture was stirred at RT for further 2 hours. Ice was added, and the solution acidified to pH 3. The separated product was extracted with EtOAc (2×25 mL), washed with water and dried (Na$_2$SO$_4$), and the solvent was removed under reduced pressure. The product was applied on a 10 g precolumn that was attached to 25 g Gold column and eluted with 50% (1% AcOH/EtOAc)/hexanes for 5 minutes followed by up to 1% AcOH/EtOAc over 20 minutes. Fractions were pooled after TLC. Trace acetic acid was removed by dissolving the residue in EtOAc and adding n-heptane and removing the volatiles at reduced pressure. The process was repeated with minimum EtOAc and n-heptane 3 times. The product was further purified by crystallizing from EtOAc/hexanes.

(S)-2-Amino-3-(2-(4-(benzyloxy)phenyl)acetamido)propanoic acid, 1, HCl. A solution of compound 1.3 (0.218 g) in 4N HCl/dioxane (7 mL) was stirred at 0° C. for 2 hours. Then it was allowed to warm up to RT and it was concentrated under reduced pressure to half volume. Then ether was added to precipitate the product. The product was filtered, washed with excess ether and the trace solvent was removed under high vacuum overnight to afford compound 1 HCl.

Compound 2 can be prepared by using a process that begins with O-alkylation of methyl-(4-hydoxyphenyl) acetate (3.1) with 1-(bromomethyl) naphthalene (2.1, e.g., in presence of an inorganic base, such as cesium carbonate, in a polar aprotic solvent, such as DMF) to provide 2.2. Ester hydrolysis of 2.2 (e.g., using potassium hydroxide in water) provides 2.3. Amide coupling of 2.3 with alpha-N-protected (S)-2,3-diaminopropionic acid, such as Boc-Dap-OH (1.2), e.g., in the presence of a cross-coupling reagent, such as 1,1′-carbonyldiimidazole (CDI), in a polar, aprotic solvent, such as DMF, provides 2.4. N-Deprotection of 2.4 (e.g., using HCl in 1,4-dioxane) provides Compound 2.

Compound 2 HCl, (S)-2-Amino-3-(2-(4-(naphthalen-1-ylmethoxy)phenyl)acetamido)propanoic acid, HCl, was synthesized according to the following synthetic route:

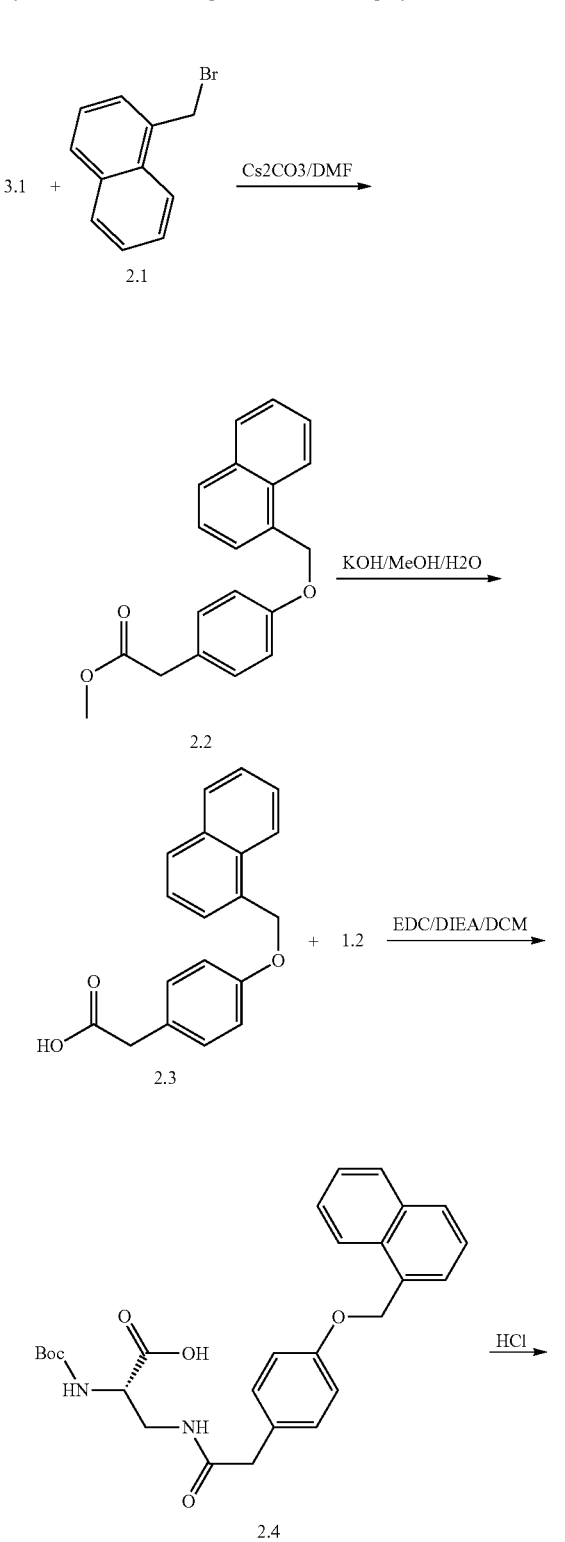

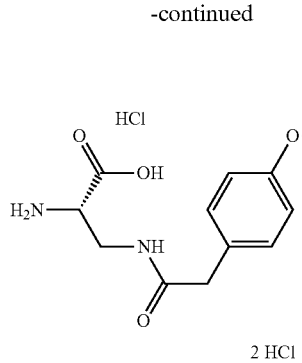

2 HCl

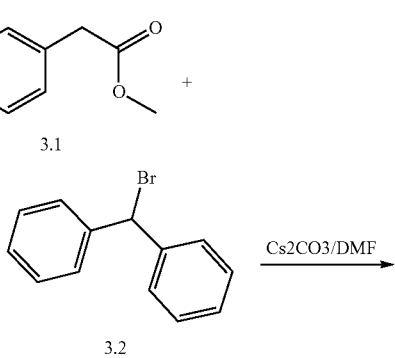

Methyl 2-(4-(naphthalen-1-ylmethoxy)phenyl)acetate 2.2. To a solution of compound 3.1 (0.810 g) in DMF (6 mL) were added $Cs_2CO_3$ (2.38 g) and 1-bromomethylnapthalene (1.13 g). The reaction mixture was stirred at RT overnight. The reaction mixture was quenched with ice and water. The solution was extracted with EtOAc (2×35 mL), washed with water (2×20 mL) and brine (20 mL), and dried ($Na_2SO_4$), and the solvent was removed under reduced pressure. The crude product was applied on a 25 g precolumn that was attached to 25 g Gold column and eluted with 5% EtOAc/Hexane for 10 minutes followed by 5-30% EtOAc/hexanes over 20 minutes.

2-(4-(naphthalen-1-ylmethoxy)phenyl)acetic acid 2.3. To a solution of compound 2.2 (1.32 g) in MeOH (60 mL) was added KOH (1.69 g) in water (15 mL). The reaction mixture was stirred at RT overnight. The solution was concentrated under reduced and ice was added before acidification to pH 3. The precipitated solid was filtered, washed with water, dried under suction and then under high vacuum overnight.

(S)-2-((tert-butoxycarbonyl)amino)-3-(2-(4-(naphthalen-1-ylmethoxy)phenyl)acetamido)-propanoic acid 2.4. To a solution of the napthylphenylacetic acid derivative 2.3 (0.500 g) in DCM (15 mL) were added DIEA (0.90 mL) and EDAC (0.328 g). The reaction mixture was stirred at RT for 15 minutes. Then Boc-Dap-OH (0.349 g) was added and the reaction mixture was stirred at RT for 3 days. The reaction mixture was washed with water (2×20 mL) and brine (15 mL), and dried ($Na_2SO_4$), and the solvent was removed under reduced pressure. The product was applied on a 10 g precolumn that was attached to 25 g Gold column and eluted with 30% (1% AcOH/EtOAc)/hexanes for 5 minutes followed by up to 1% AcOH/EtOAc over 20 minutes. Fractions were pooled after TLC. Trace acetic acid was removed by dissolving the residue in EtOAc and adding n-heptane and removing the volatiles at reduced pressure. The process was repeated with minimum EtOAc and n-heptane 3 times.

(S)-2-Amino-3-(2-(4-(naphthalen-1-ylmethoxy)phenyl) acetamido)propanoic acid, 3, HCl. A solution of compound 2.4 (0.289 g) in 4N HCl/dioxane (7 mL) was stirred at 0° C. for 2 hours. Then it was allowed to warm to RT and it was concentrated under reduced pressure to half volume. Then ether was added to precipitate the product. The product was filtered, washed with excess ether and the trace solvent was removed under high vacuum overnight.

Compound 3, (S)-2-amino-3-(2-(4-(benzhydryloxy)phenyl)acetamido)propanoic acid, was synthesized according to the following synthetic route:

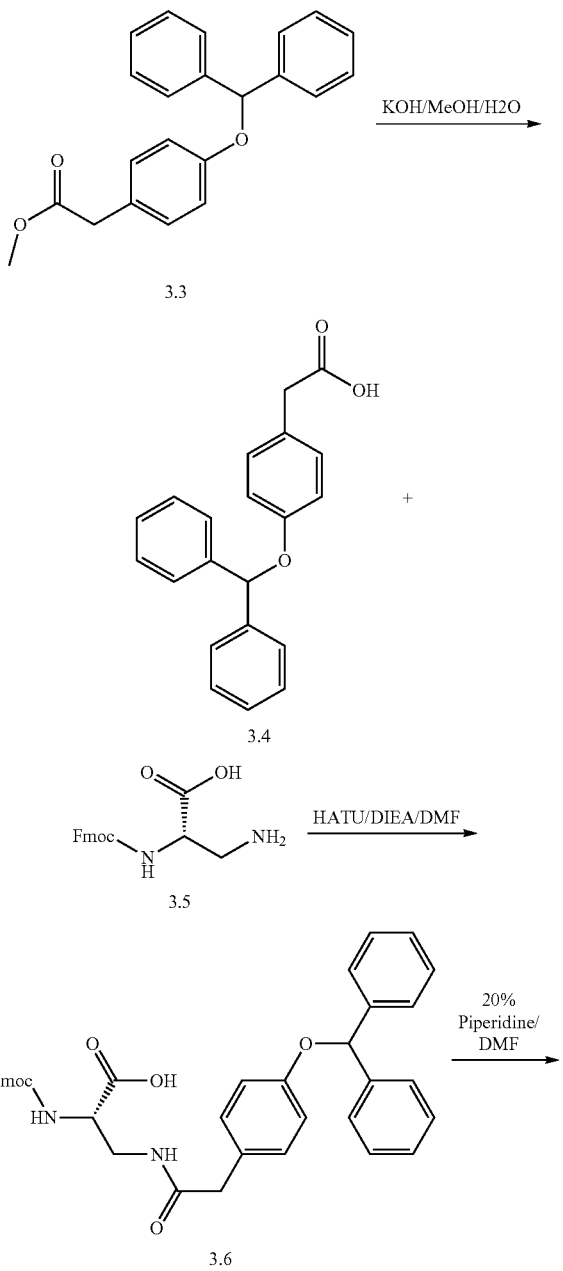

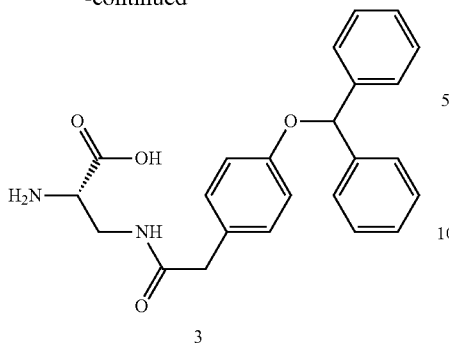

Methyl 2-(4-(benzhydryloxy)phenyl)acetate 3.2. To a solution of compound 3.1 (1.00 g) in dimethylformamide (DMF, 9 mL) were added $Cs_2CO_3$ (2.94 g) and a solution of benzhydryl bromide (1.56 g) in DMF (5 mL). The reaction mixture was stirred at room temperature (RT) overnight. The reaction mixture was quenched with ice and water. The solution was extracted with ethyl acetate (EtOAc, 2×35 mL), washed with water (20 mL) and brine (20 mL), and dried (over $Na_2SO_4$), and the solvent was removed under reduced pressure. The isolated product was applied on a 25 g precolumn that was attached to 25 g Gold column and eluted with 10% EtOAc/hexanes for 5 minutes followed by 10-30% EtOAc/hexanes over 30 minutes.

2-(4-(Benzhydryloxy)phenyl)acetic acid 3.4. To a solution of compound 3.3 (0.800 g) in methanol (MeOH, 25 mL) was added KOH (0.945 g) in water (10 mL). The reaction mixture was stirred at RT overnight. The solution was concentrated under reduced pressure, and ice was added before acidification to pH 3. The precipitated solid was filtered, washed with water, dried under suction and then under high vacuum overnight.

(S)-2-((((9H-fluoren-9-yl)methoxy)carbonyl)amino)-3-(2-(4-(benzhydryloxy)phenyl)acetamido)-propanoic acid 3.6. To a solution of benzhydrylacetic acid derivative 3.4 (0.212 g) in DMF (3 mL) were added diisopropylethylamine (DIEA, 0.35 mL) and 1-[bis(dimethylamino)methylene]-1H-1,2,3-triazolo[4,5-b]pyridinium 3-oxide hexafluorophosphate (HATU, 0.279 g). The reaction mixture was stirred at RT for 25 minutes. Then Fmoc-Dap-OH (0.217 g) was added, and the reaction mixture was stirred at RT for further 2 hours. Ice was added, and the solution acidified to pH 3. The precipitated solid was filtered, washed with water and dried in vacuum desiccator overnight. The product was applied on a 5 g precolumn that was attached to 25 g Gold column and eluted with 0.25% AcOH/DCM for 5 minutes followed by 0-5% MeOH/(0.25% AcOH-DCM) over 30 minutes. Fractions were pooled after thin-layer chromatography (TLC). Trace acetic acid was removed by dissolving the residue in EtOAc and adding n-heptane, then removing the volatiles at reduced pressure. The process was repeated with minimum DCM and n-heptane 2 times.

(S)-2-amino-3-(2-(4-(benzhydryloxy)phenyl)acetamido) propanoic acid 3. To a solution of compound 3.6 (0.220 g) in DMF (3.5 mL) was added piperidine (0.80 mL), and the reaction mixture was stirred at RT for 2 hours. The reaction mixture was poured over ice. The separated solid with the aqueous mixture was extracted with ether (3×20 mL). The separated aqueous layer was acidified to pH 3 and the separated solid was filtered, washed with excess water. It was dried under vacuum desiccator overnight.

Example 6. Synthesis of Compound 8

Compound 8 was synthesized using the following reactions.

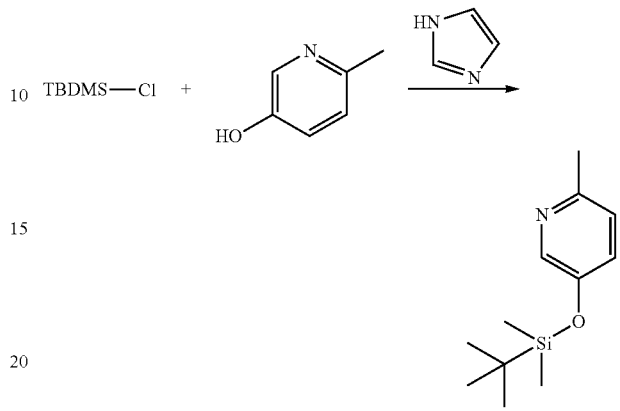

5-((Tert-butyldimethylsilyl)oxy)-2-methylpyridine. To a solution of 6-methylpyridin-3-ol (2.50 g) in DMF (40 mL) was added imidazole (3.12 g). The reaction mixture was stirred under nitrogen atmosphere. To this solution was added slowly a solution of tert-butyldimethylsilyl chloride (TBDMS-Cl; 4.66 g) in DMF (10 mL). The reaction mixture was stirred at RT for 3 h. Thin layer chromatography (TLC) indicated completion of reaction. The reaction mixture was quenched with water. The solution was extracted with ethyl acetate (EtOAc; 2×100 mL), washed with water (2×30 mL) and brine (20 mL), and dried over $Na_2SO_4$, and the solvent was removed under reduced pressure. The crude compound was applied on a precolumn that was attached to a 40 g gold column and eluted with 0-40% EtOAc/hexanes over 30 minutes. Fractions were pooled after TLC. The desired product was eluted around 15-25% EtOAc/hexanes to give 5-((tert-butyldimethylsilyl)oxy)-2-methylpyridine (4.76 g).

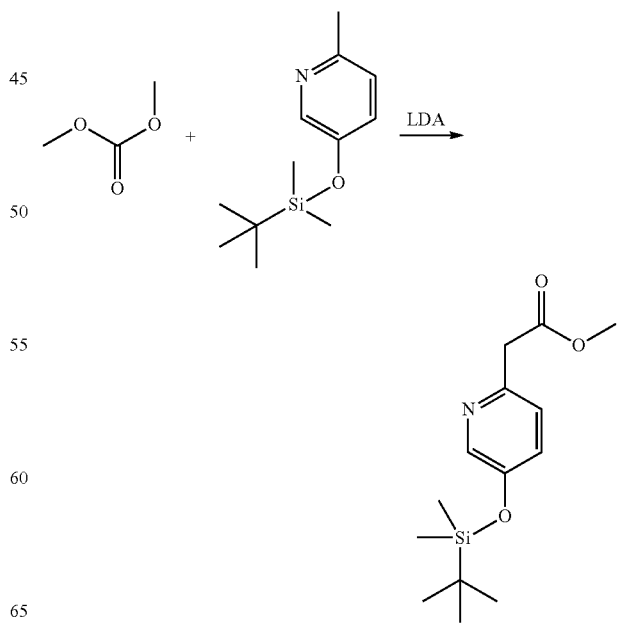

Methyl 2-(5-((tert-butyldimethylsilyl)oxy)pyridin-2-yl)acetate. To a solution of 5-((tert-butyldimethylsilyl)oxy)-2-methylpyridine (2.31 g) in tetrahydrofuran (THF; 50 mL) at −78° C. was added slowly lithium diisopropylamide (LDA) in THF (41.2 mL, 1 M). The reaction mixture was stirred at −78° C. for further 10 minutes. Then a solution of Me$_2$CO$_3$ (3.5 mL) was added. The reaction mixture was stirred at −78° C. for 1 h. The reaction mixture was quenched with saturated ammonium chloride solution (15 mL). The solution was extracted with EtOAc (2×75 mL), washed with water (2×30 mL) and brine (20 mL), and dried over Na$_2$SO$_4$, and the solvent was removed under reduced pressure. The crude compound was applied on a precolumn that was attached to a 40 g gold column and eluted first with 5% EtOAc/hexanes followed by up to 40% EtOAc/hexanes over 60 minutes. Fractions were pooled after TLC and concentrated to give methyl 2-(5-((tert-butyldimethylsilyl)oxy)pyridin-2-yl)acetate (0.720 g).

Methyl 2-(5-(naphthalen-1-ylmethoxy)pyridin-2-yl)acetate. To a solution of methyl 2-(5-hydroxypyridin-2-yl)acetate (0.405 g) in DMF (9 mL) were added Cs$_2$CO$_3$ (1.58 g) and 1-bromomethylnapthalene (0.562 g). The reaction mixture was stirred at RT for 3 h. TLC indicated completion of reaction. The reaction mixture was quenched with ice and water. The solution was extracted with EtOAc (2×25 mL), washed with water (2×10 mL) and brine (15 mL), and dried over Na$_2$SO$_4$, and the solvent was removed under reduced pressure. The crude compound was applied on a precolumn that was attached to a 12 g gold column and eluted with 10-40% EtOAc/hexanes over 40 minutes. Products eluted out between 30% and 40% EtOAc/hexanes. Fractions were pooled after TLC and concentrated to give methyl 2-(5-(naphthalen-1-ylmethoxy)pyridin-2-yl)acetate (510 mg).

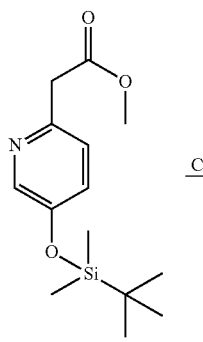 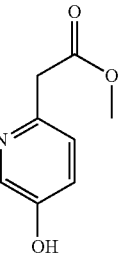 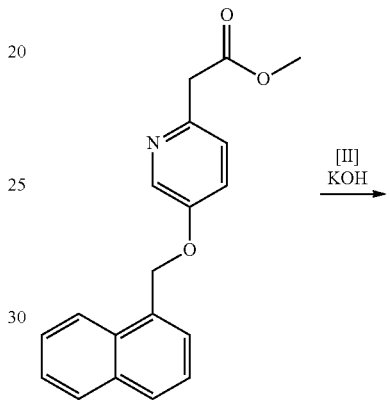

Methyl 2-(5-hydroxypyridin-2-yl)acetate. To a solution of methyl 2-(5-((tert-butyldimethylsilyl)oxy)pyridin-2-yl)acetate (0.698 g) in dimethylformamide (DMF; 8 mL) was added CsF (0.75 g). The reaction mixture was stirred at room temperature overnight. The reaction mixture was diluted with EtOAc (25 mL), the solution was washed with water (2×10 mL) and brine (10 mL), and dried over Na$_2$SO$_4$, and the solvent was removed under reduced pressure to give methyl 2-(5-hydroxypyridin-2-yl)acetate (0.415 g).

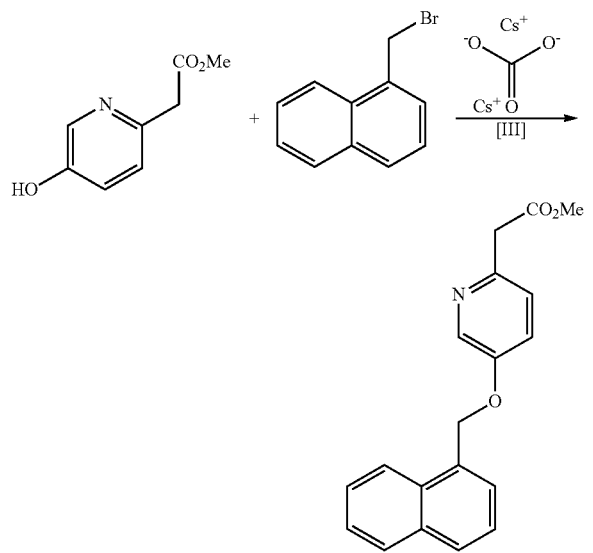

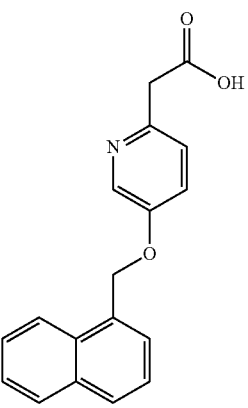

2-(5-(Naphthalen-1-ylmethoxy)pyridin-2-yl)acetic acid. To a solution of methyl 2-(5-(naphthalen-1-ylmethoxy)pyridin-2-yl)acetate (0.495 g) in methanol (40 mL) was added KOH (0.50 g) in water (6 mL). The reaction mixture was stirred at RT overnight. TLC indicated completion of reaction. The solution was concentrated under reduced pressure and acidified with 2N HCl (dropwise) after addition of ice. The solution was extracted with EtOAc (2×100 mL), washed with brine and dried (Na$_2$SO$_4$). The solvent was removed under reduced pressure to give 2-(5-(naphthalen-1-ylmethoxy)pyridin-2-yl)acetic acid (0.470 g). HPLC: 97.8%, MS: 294.1122 (M+1); 316.0953 (M+23).

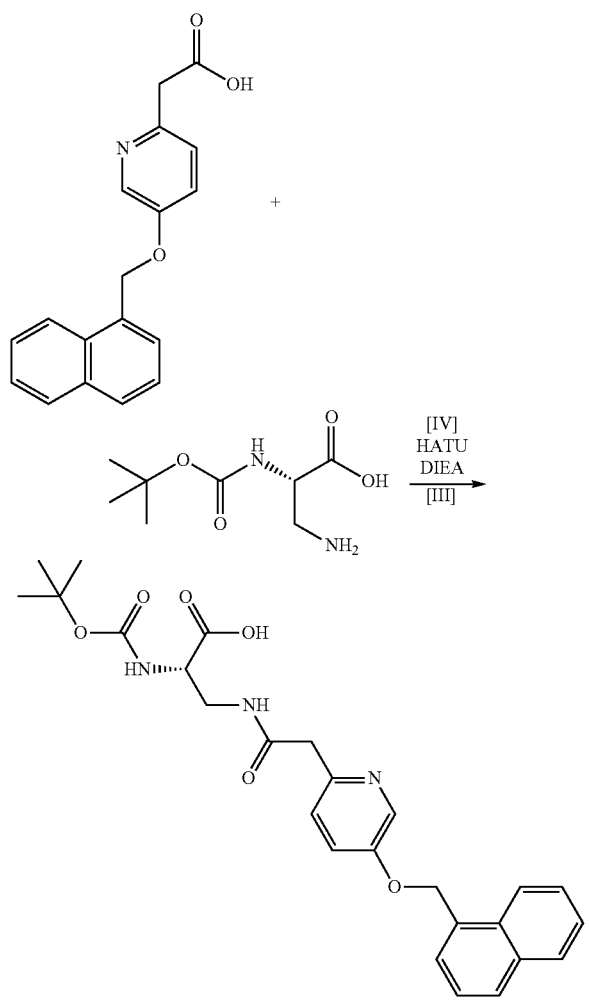

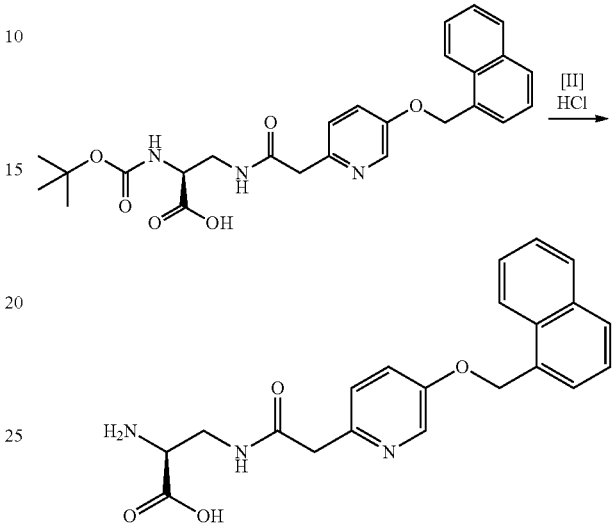

(S)-2-((tert-butoxycarbonyl)amino)-3-(2-(5-(naphthalen-1-ylmethoxy)pyridin-2-yl)acetamido)propanoic acid. To a solution of 2-(5-(naphthalen-1-ylmethoxy)pyridin-2-yl)acetic acid (0.420 g) in DMF (10 mL) were added diisopropylethylamine (DIEA; 0.28 mL) and 1-[bis(dimethylamino)methylene]-1H-1,2,3-triazolo[4,5-b]pyridinium 3-oxide hexafluorophosphate (HATU; 0.561 g). The reaction mixture was stirred at RT for 2.5 h. Then, (S)-3-amino-2-(tert-butoxycarbonyl)aminopropionic acid (Boc-Dap-OH; 0.292 g) and DIEA (0.27 mL) were added and the reaction mixture was stirred at RT for 4 h. TLC and high performance liquid chromatography (HPLC) indicated completion of reaction. The reaction was quenched with ice and the precipitated sticky substance was extracted with EtOAc (2×75 mL). The combined organics were washed with water (2×50 mL) and brine (30 mL), and the solvent was removed under reduced pressure. The residue was recrystallized from EtOAc, filtered, washed with EtOAc (5 mL) followed by about 50% EtOAc/hexanes (20 mL) and air dried under suction to give 126 mg of product.

MS: 666.3124 (M+H: 666.3139); 688.2954 (M+Na: 688.2959) indicated that the major product was from coupling of the desired product with Boc-Dap-OH. The compound was washed with EtOAc (30 mL) and the solvent was removed under suction. Solvent was removed from the mother liquor under reduced pressure and the crude product was applied on a 25 g precolumn that was attached to 25 g Gold column and eluted with 2-10% (0.25% AcOH/DCM)/MeOH over 40 minutes. Fractions were pooled after checking TLC to give 59 mg of (S)-2-((tert-butoxycarbonyl)amino)-3-(2-(5-(naphthalen-1-ylmethoxy)pyridin-2-yl)acetamido)propanoic acid. MS: 480.2119 (M+H: 480.2134); 502.1951 (M+Na: 502.1954).

(S)-2-Amino-3-(2-(5-(naphthalen-1-ylmethoxy)pyridin-2-yl)acetamido)propanoic acid. A solution of (S)-2-((tert-butoxycarbonyl)amino)-3-(2-(5-(naphthalen-1-ylmethoxy)pyridin-2-yl)acetamido)propanoic acid (0.050 g) in 4N HCl/dioxane (0.6 mL) was stirred at 0° C. for 3 h. Then it was allowed to warm up to RT and it was concentrated under reduced pressure (up to 40° C.) to half volume. Then, ether was added to the colloidal solution. The separated product was filtered and washed with excess ether, and the trace solvent was removed under high vacuum overnight to give (S)-2-amino-3-(2-(5-(naphthalen-1-ylmethoxy)pyridin-2-yl)acetamido)propanoic acid (40 mg).

HPLC: 96.3%, MS: 380.1605 (M+H: 380.1611); 402.1418 (M+Na: 402.1430), $^1$H NMR (700 MHz, dmso) δ 13.93 (s, 1H), 8.62 (s, 1H), 8.56 (s, 1H), 8.47-8.38 (m, 3H), 8.13 (d, J=8.1 Hz, 1H), 7.98 (dd, J=18.0, 8.1 Hz, 2H), 7.91 (s, 1H), 7.72 (d, J=7.0 Hz, 1H), 7.63-7.52 (m, 4H), 5.71 (s, 2H), 4.02 (s, 1H), 3.82 (s, 2H), 3.65 (dd, J=12.6, 7.0 Hz, 1H), 3.53-3.49 (m, 1H).

Example 7. Compound 2 Pharmacology in Human PBMCs

A series of experiments were performed to understand the pharmacology of Compound 2 in human peripheral blood mononuclear cells (PBMCs).

Figure 4A:
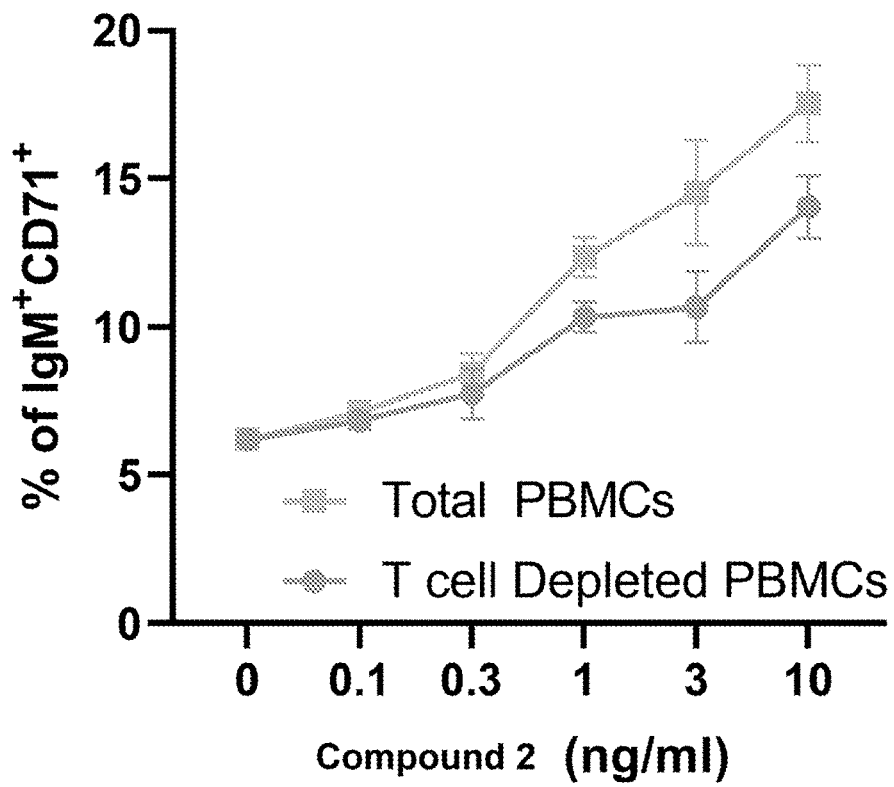
FIG. 4A is a graph of percentage of IgM$^+$CD71$^+$ cells versus concentration of Compound 2, and shows Compound 2 enhances human regulatory B-cells (CD19$^+$IgM$^+$CD71$^+$).

$2×10^5$ Total PBMCs or T-cell depleted PBMCs were cultured in a 96-well plate in the presence of ascending doses of Compound 2 ranging from 0 to 10 ng/ml for five days. At day 5, cells were washed and stained for CD19, CD71 and IgM for 30 minutes on ice, then cells were washed with PBS, and stained with viability dye to exclude dead cells. The results are shown in FIG. 4A.

Compound 2 enhances regulatory B cells (CD19$^+$CD71$^+$ IgM$^+$). More specifically, Compound 2 enhanced the expression of regulatory markers (CD71, IgM) on human B-cells in the absence of T-cells (T-cell depleted PBMCs), and the presence of T-cells increased the expression of these regulatory markers, suggesting that the effects of Compound 2 on regulatory B cells can be further enhanced by T-cell/B-cell interaction. For example, treatment with 10 ng/ml Compound 2 increased the percentage of B-reg in T-cell depleted PBMCs and total PBMC cultures from 6.19% to 14.0% and 17.5%, respectively. Other regulatory B cell markers of interest include CD24, CD38 and CD27.

Figure 4B:
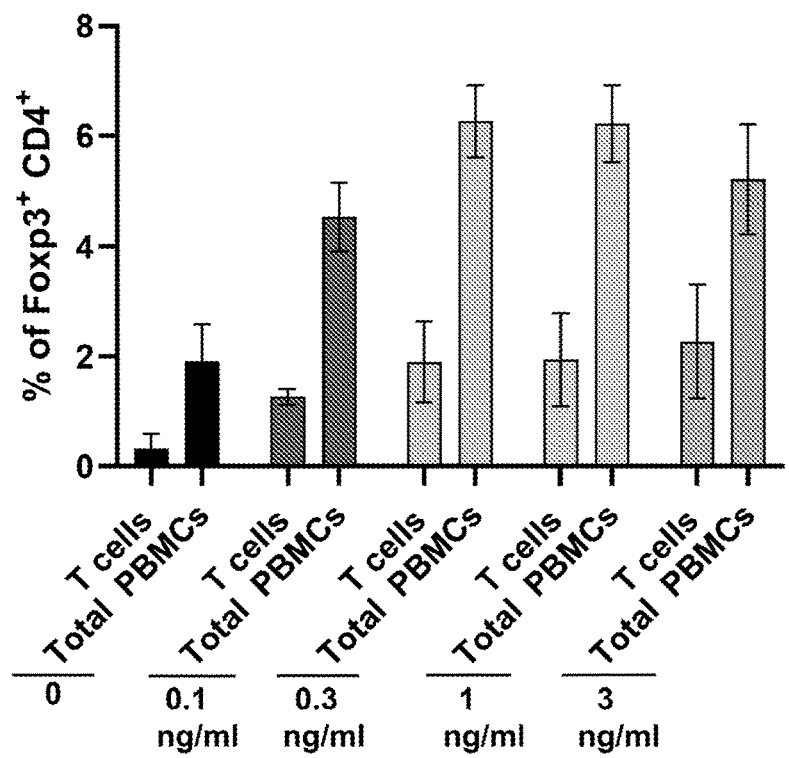
FIG. 4B is a bar graph, and shows Compound 2 acts directly on T-cells in the presence and absence of other immune cells to enhance $T_{regs}$ (FoxP3$^+$).

$2 \times 10^5$ Total PBMCs or sorted T-cells (CD3$^+$) were cultured in 96-well plates in the presence of ascending doses of Compound 2 ranging from 0 to 3 ng/ml for five days. On day 5, cells were washed and stained for CD3 and CD4 for 30 minutes on ice, then cells were washed with PBS and stained with viability dye to exclude dead cells. Stained cells were fixed/permeabilized and further stained for Foxp3. Finally, cells were washed and fixed for acquisition by Attune NXT flow cytometer. Data were analyzed by FlowJov10. The results are shown in FIG. 4B.

Treatment with 3 ng/ml of Compound 2 increased the percentage of CD4+/Foxp3+ T-cells in a culture of isolated T-cells (sorted) from 0.32% to 2.27% (a 606% increase). In total PBMC, treatment with 3 ng/ml of Compound 2 increased the percentage of CD4+/Foxp3+ T-cells from 1.9% to 5.2% (a 171% increase). These results show that Compound 2 acts directly on T-cells in the presence and absence of other immune cells to enhance Foxp3 expression.

Total human PBMCs isolated from healthy human volunteers were cultured in vitro in a Th17 polarizing environment as follows:
  Day 0: $2 \times 10^5$ cells/well were incubated in a 96 round bottomed-well plate (final volume 200 µl) with (i) anti CD3/CD28 microbead for T-cell activation (1 bead/10 cells), (ii) 10 ng/ml IL-6, 2 ng/ml TGFβ and 10 ng/ml IL-23, and (iii) 10 µg/ml anti-IFNγ and 10 µg/ml anti-IL-4.
  Day 4: Each well was split into two wells, and 100 µl of media containing the same cytokine/antibody cocktail used at day 0 was added to each well in the presence of ascending doses of Compound 2 (0, 0.1, 0.3, 1, and 3 ng/ml).
  Day 9: Cells were washed and stained for surface staining (CD3, CD4), then viability dye to exclude dead cells. Intranuclear staining was performed after cell fixation and permeabilization for transcription factors Foxp3 and RORγt. Cells were washed and fixed for acquisition by Attune NXT flow cytometer. Data were analyzed by FlowJov10.

Figure 4C:
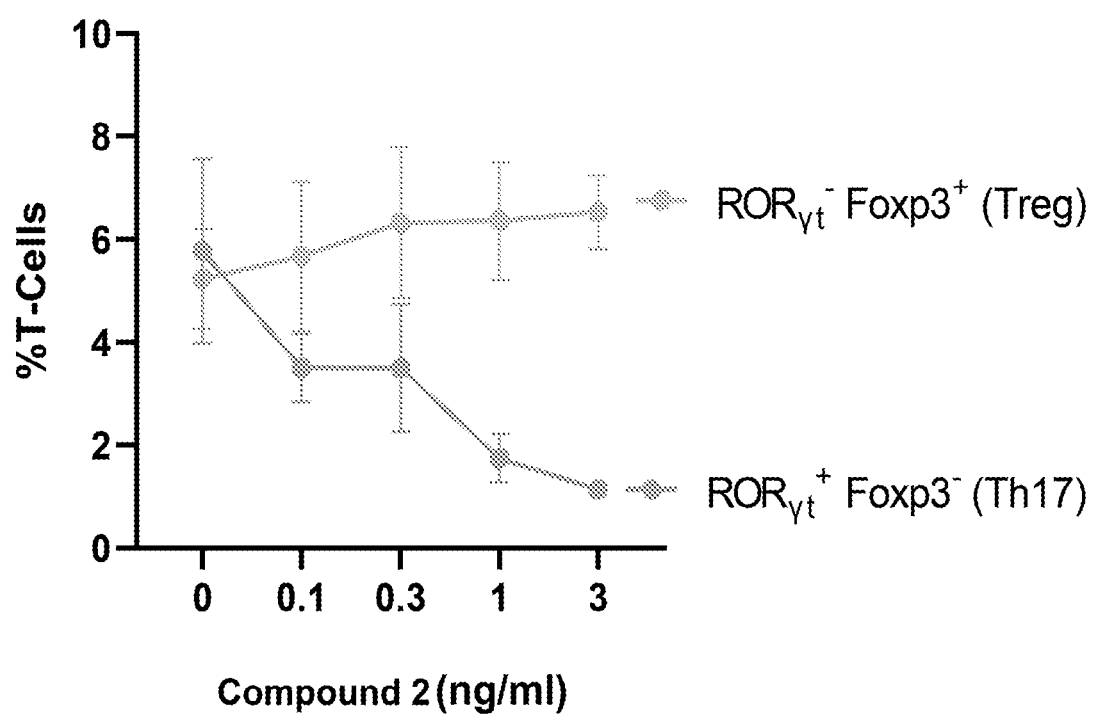
FIG. 4C is a graph of percentage of T-cells versus concentration of Compound 2, and shows Compound 2 maintains FoxP3 expression and inhibits RORγt expression in Th17 polarizing environment in vitro.

The results, shown in FIG. 4C, show that Compound 2 maintains Foxp3 expression and inhibits RORγt expression in Th17 polarizing environment (representative of a pro-inflammatory environment) in vitro. In a strongly pro-inflammatory environment, treatment with Compound 2 inhibited Th17, as evident by a statistically significant (t-test) reduction of percentage of Th17 from a mean of 5.8% to a mean of 1.1%, representing an 80% decrease in RORγt cells.

Total human PBMCs were isolated from six subjects with confirmed diagnosis of MS. On Day 0, $2 \times 10^5$ cells/well were incubated in a 96 round bottomed-well plate alone or with up to 2.5 µM Compound 2 for five days. On Day 5, cells were collected, washed and stained for surface staining (CD3, CD4), then viability dye to exclude dead cells. Intranuclear staining was performed after cell fixation and permeabilization for transcription factor FoxP3. Cells were washed and fixed for acquisition by Attune NXT flow cytometer. Data were analyzed by FlowJov10. The results are shown in FIG. 4D.

Figure 4D:
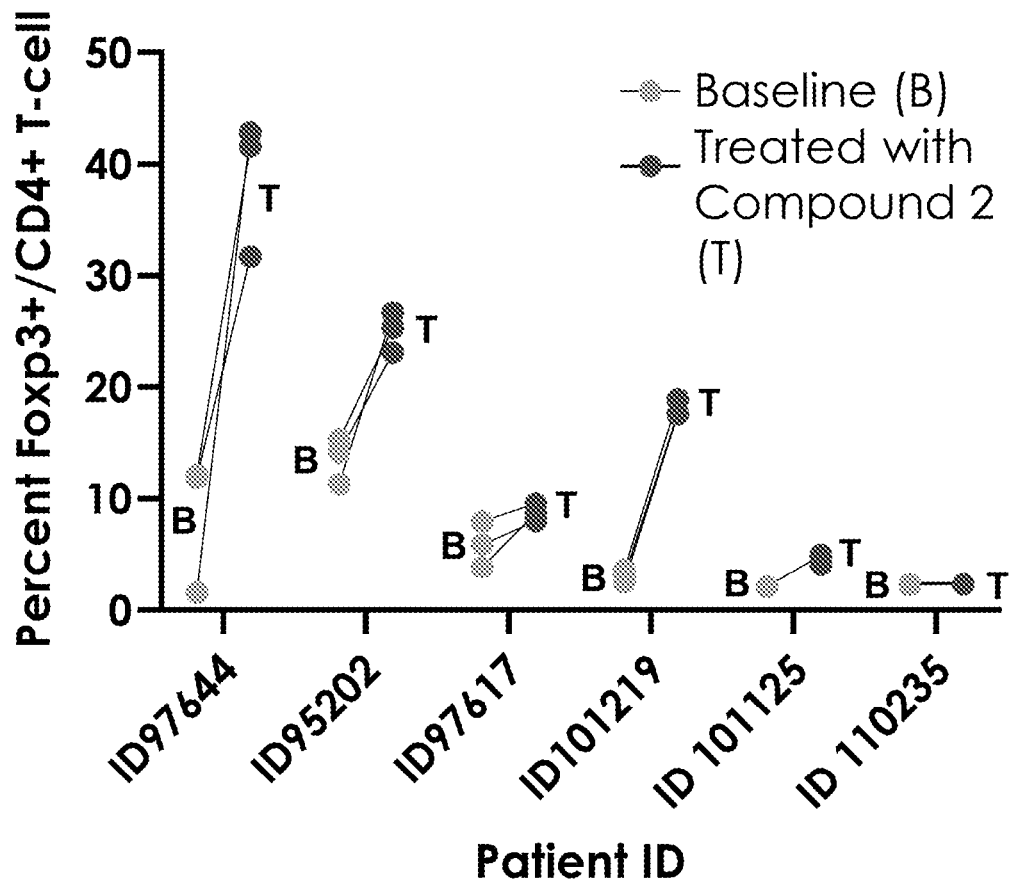
FIG. 4D is a graph of percentage of FoxP3$^+$/CD4$^+$ T-cells in multiple sclerosis patient samples before and after treatment with Compound 2, and shows changes in the patient samples in response to Compound 2.

T-cells derived from blood of five out of six MS patients responded to treatment with Compound 2 ex vivo, as seen in FIG. 4D by the increase in the percentage of Foxp3+/CD4+ T-cells.

Example 8. Evaluating the Therapeutic Effects of Compound 2 in an Escalation Treatment Paradigm in MOG$_{35-55}$-induced Murine EAE Model All animal studies were conducted under IACUC number B2020-91 and in compliance with Tufts University/Tufts Medical Center & Human Nutrition Research Center on Aging. Animals were housed four in a cage and had access to food and water ad libitum.

Table 7 lists materials and reagents used in this experiment.

TABLE 7

| Key materials and reagents | |
|---|---|
| Material/Reagent | Commercial Source (Catalog No.) |
| MOG$_{35-55}$ | R&D (25681) |
| Complete Freund's Adjuvant (CFA) | ThermoScientific (77140) |
| Pertussis Toxin (PT) | List Biological Laboratories Inc (NC0830484) |
| Natalizumab | MedChem Express (HY-108831). |
| Dimethyl Fumarate (DMF) | Sigma Aldrich (242926-100G) |
| METHOCEL ® | Sigma (64625-100G-F) |

Compound 2 (0.03 mg/ml) was formulated with hydroxypropyl beta cyclodextrin (HβCD) 1:80 (Compound 2:HβCD) and stored at 4° C. until use. Natalizumab, an anti-α4β1 integrin antibody is a monoclonal antibody that is approved by U.S. Food and Drug Administration (FDA) for the treatment of relapsing forms of MS. It is generally recommended for patients who have had an inadequate response to, or are unable to tolerate an alternate MS therapy. Natalizumab was diluted in PBS to a final concentration of 15 mg/ml before dosing. DMF is a disease-modifying therapy (DMT) recommended for the treatment of active relapsing multiple sclerosis. DMF (1 g) was dissolved in 50 ml of 4% solution of METHOCEL® to give a 20 mg/ml solution of DMF. The solution was stored at 4° C. until use.

Experimental autoimmune (allergic) encephalomyelitis (EAE) is considered to be the best non-clinical model of multiple sclerosis (MS). Over 6,000 papers have been published in scientific journals on this model. EAE is characterized by immune responses against CNS tissue and can be induced in animals by immunizing them against proteins of the CNS. In the active EAE model, mice are immunized with MOG$_{35-55}$ peptide emulsified in Complete Freund's Adjuvant (CFA) by subcutaneous injection at the tail base (100 µg of MOG$_{35-33}$ per mouse) under anesthesia. On the day of injection (Day 0) and two days later (Day 2), mice receive an intraperitoneal injection of pertussis toxin (PT) in PBS at 200 ng/mouse/dose (0.1 mL). Symptoms typically develop in mice 9-14 days after immunization (Day 0). Daily observation and scoring of mice start on Day 7 and continue until the end of the study. Table 5 (see Example 4 above) details the expected clinical symptoms and the scoring criteria used in this study.

Figure 5A:
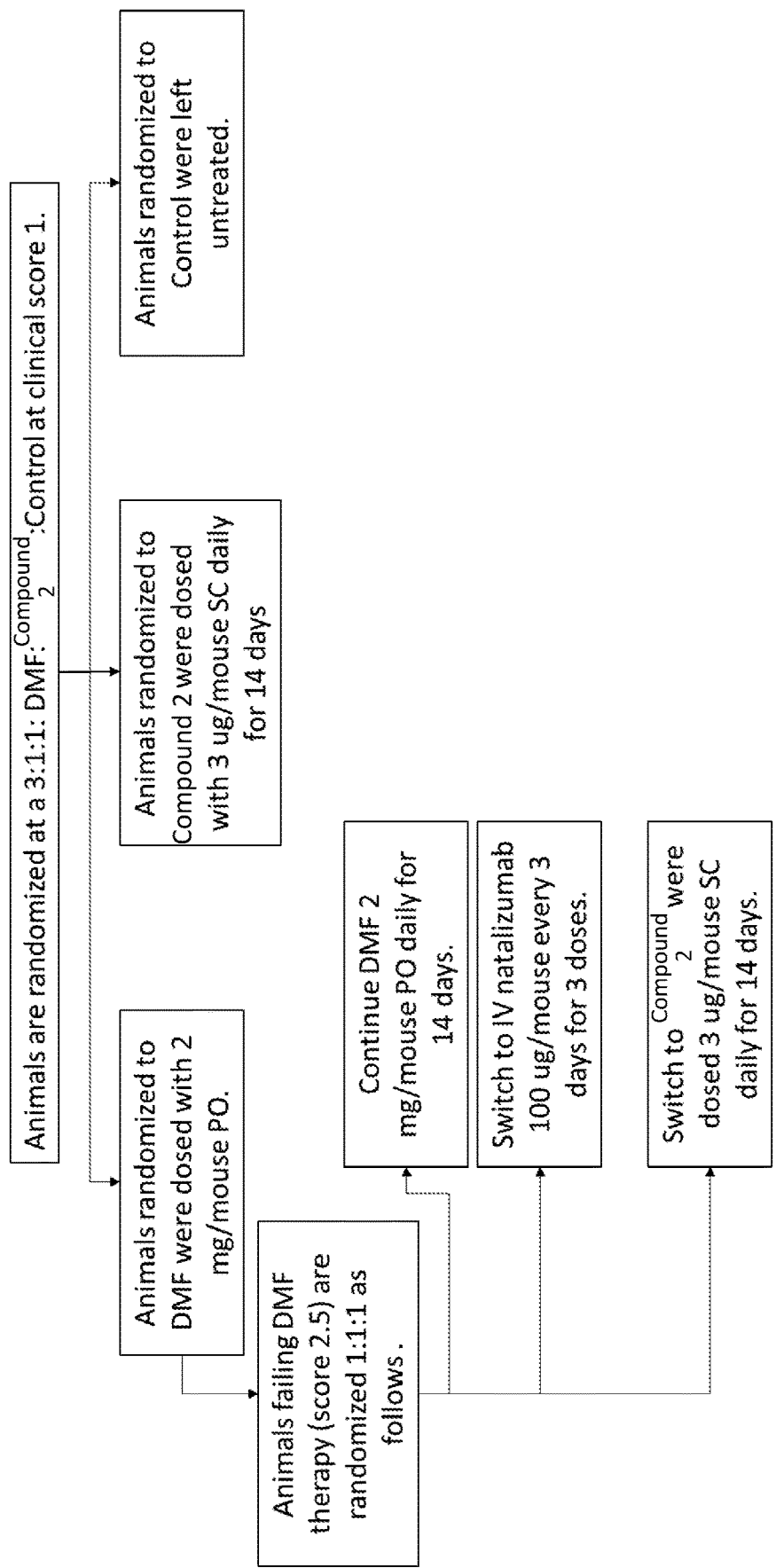
FIG. 5A shows the study design and randomization schedule of the study described in Example 8.

This study was designed to evaluate the early sustained use of Compound 2 versus DMF in a treatment escalation paradigm (sustained use cohort), and Compound 2 versus natalizumab after DMF failure (escalation cohort). All animals in the escalation cohorts received 14 doses of DMF or Compound 2, or 3 doses of natalizumab, as per group assignment. FIG. 5A shows the design and randomization schedule for animals in the study.

Probability of disease control: Disease control was defined as a clinical score of less than 2.5. Animals in the different treatment groups were monitored after the 3:1:1 randomization. A score of 2.5 was recorded as an event and analyzed by survival analysis in GraphPad Prism 9. Animals not reaching a clinical score of 2.5 by day 14, the end of the treatment period, were assigned a score of zero for the survival analysis.

Efficacy of Compound 2 versus DMF in early sustained use: Animals in the DMF group that reached a score of 2.5 were randomized 1:1:1, as per FIG. 5A. Animals randomized to continue DMF treatment were given the remainder of the 14 DMF doses. Animals from the first randomization that were treated with Compound 2 after disease onset continued treatment for a total of 14 doses. After the $14^{th}$ dose, treatment was stopped and clinical score and overall survival were monitored.

Efficacy of Compound 2 versus natalizumab in a treatment escalation cohort: Animals in the DMF group that reached a score of 2.5 were randomized 1:1:1, as per FIG. 5A. Animals randomized to natalizumab were dosed 100 µg/mouse IV every 3 days for 3 total doses starting the same day a score of 2.5 was recorded. Animals randomized to Compound 2 were dosed with 3 µg/mouse SC QD for 14 total doses starting on the same day a score of 2.5 was recorded.

Overall survival: Death due to the disease was monitored in the early sustained use cohort as well as the escalation cohort. Death by disease (clinical score of 5) was recorded as an event "1," death due to ulceration or for ex vivo analysis was recorded as "0." Animals surviving until the end of the study were recorded "0" on day 27. Survival analysis was done in GraphPad Prism 9.

Results: Disease incidence in this study was 97% (87/90 mice). Disease onset started on day 9 after immunization. Animals were randomized into treatment groups when they reached a disease score of "1," as shown in FIG. 5A. All animals were assigned a treatment group by day 15 after immunization.

IACUC guidelines mandate sacrifice of animals with immunization site ulcerations. If a sacrificed animal was assigned a treatment group, the data from that animal were used in the calculation of the average clinical score until the day the animal was put down. Euthanasia due to immunization site ulcerations was not assigned a clinical score of "5".

Figure 5B:
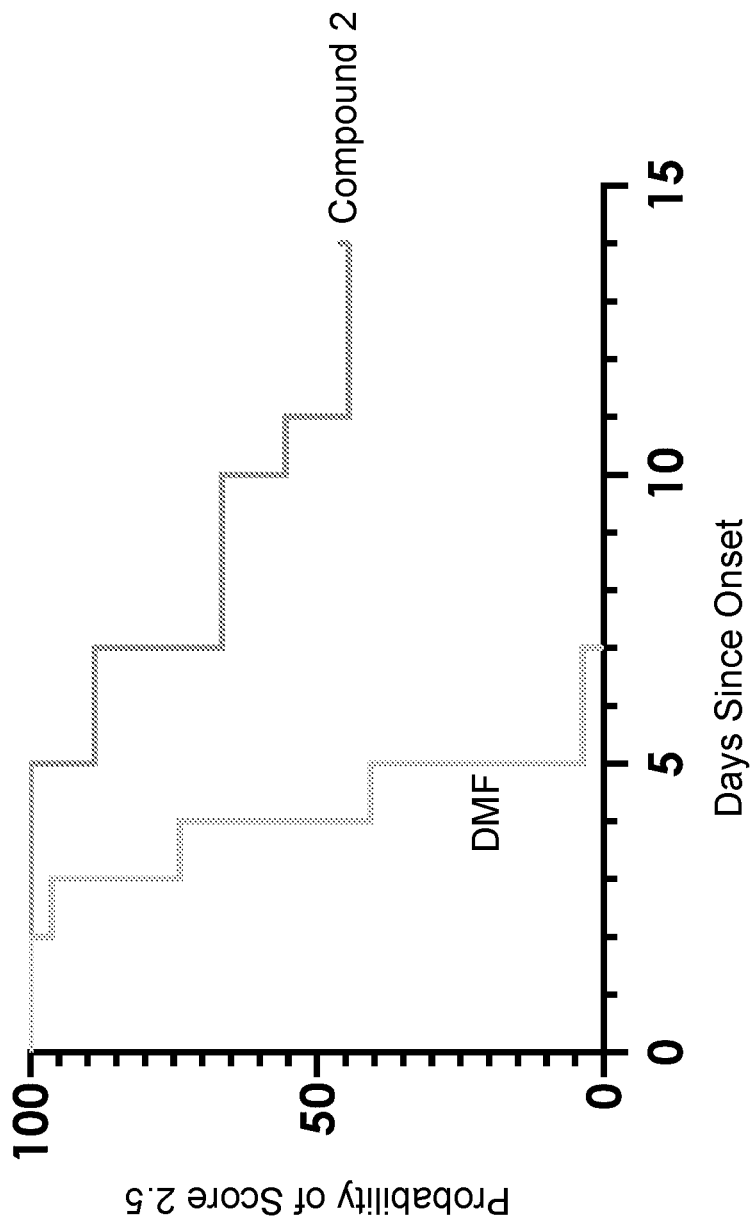
FIG. 5B shows probability of disease control (score <2.5) in Compound 2 or dimethyl fumarate (DMF) treatment groups from the study described in Example 8.

Upon disease onset (clinical score of 1), a total of 30 mice were randomized to the DMF group, 10 mice were randomized to the untreated control group, and 9 mice to the Compound 2 group (3:1:1 randomization). All animals (n=30) in the DMF treatment group progressed to a score of 2.5 within 7 days of disease onset. In contrast, just 5 of the 9 animals randomized to the Compound 2 treatment group progressed to a disease score of 2.5 over the entire treatment period (14 days)(FIG. 5B).

After reaching a score of 2.5, animals in the DMF treatment group were randomized in a 1:1:1, as per the study design. Animals in the Compound 2 group continued treatment with Compound 2, as per FIG. 5A. Of the 30 animals that progressed on DMF therapy, 9 were randomized to continue DMF therapy, 9 were randomized to natalizumab and 9 were randomized to Compound 2.

Figure 5C:
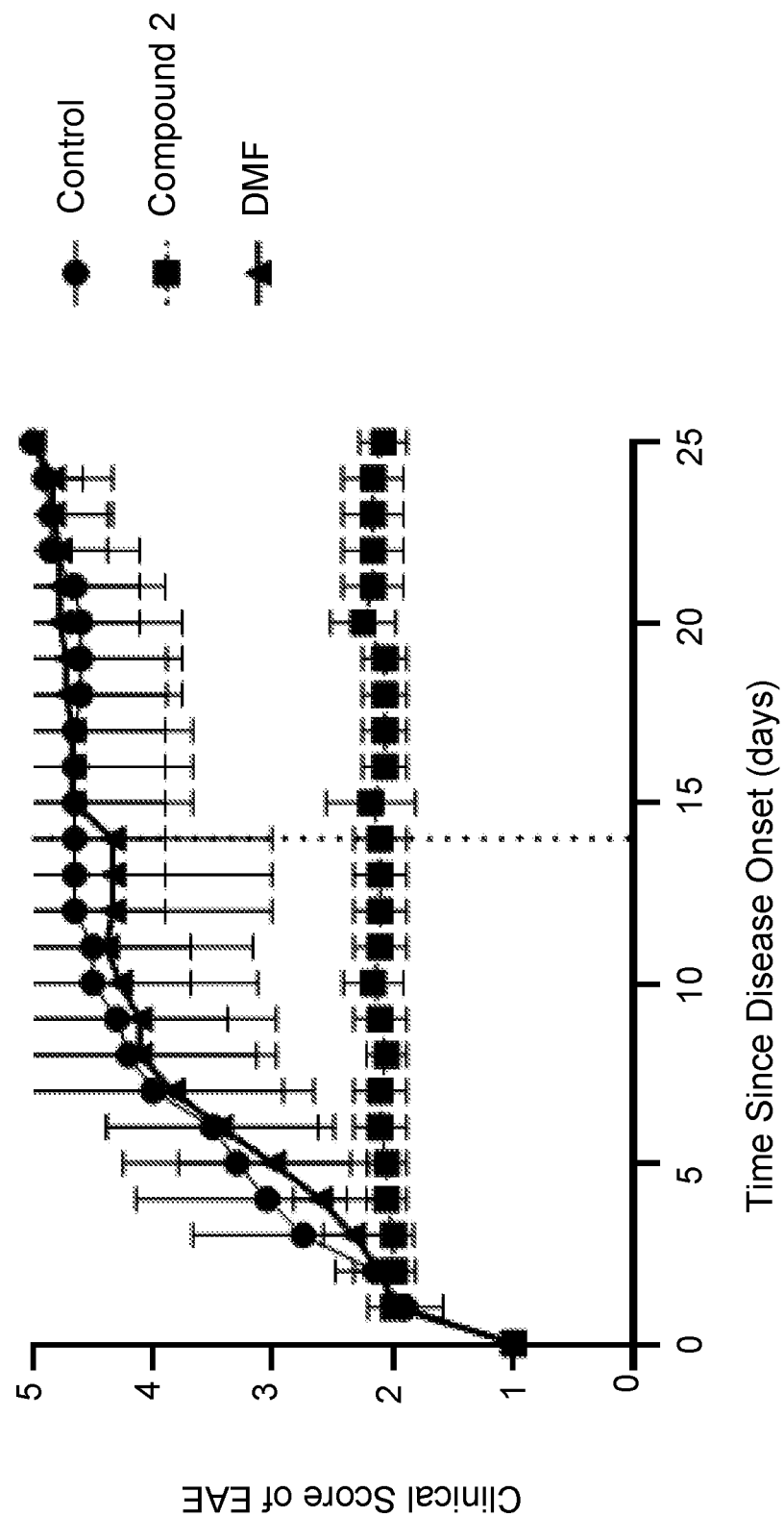
FIG. 5C shows therapeutic effects of early, sustained use of Compound 2 versus DMF in the study described in Example 8.
Figure 5D:
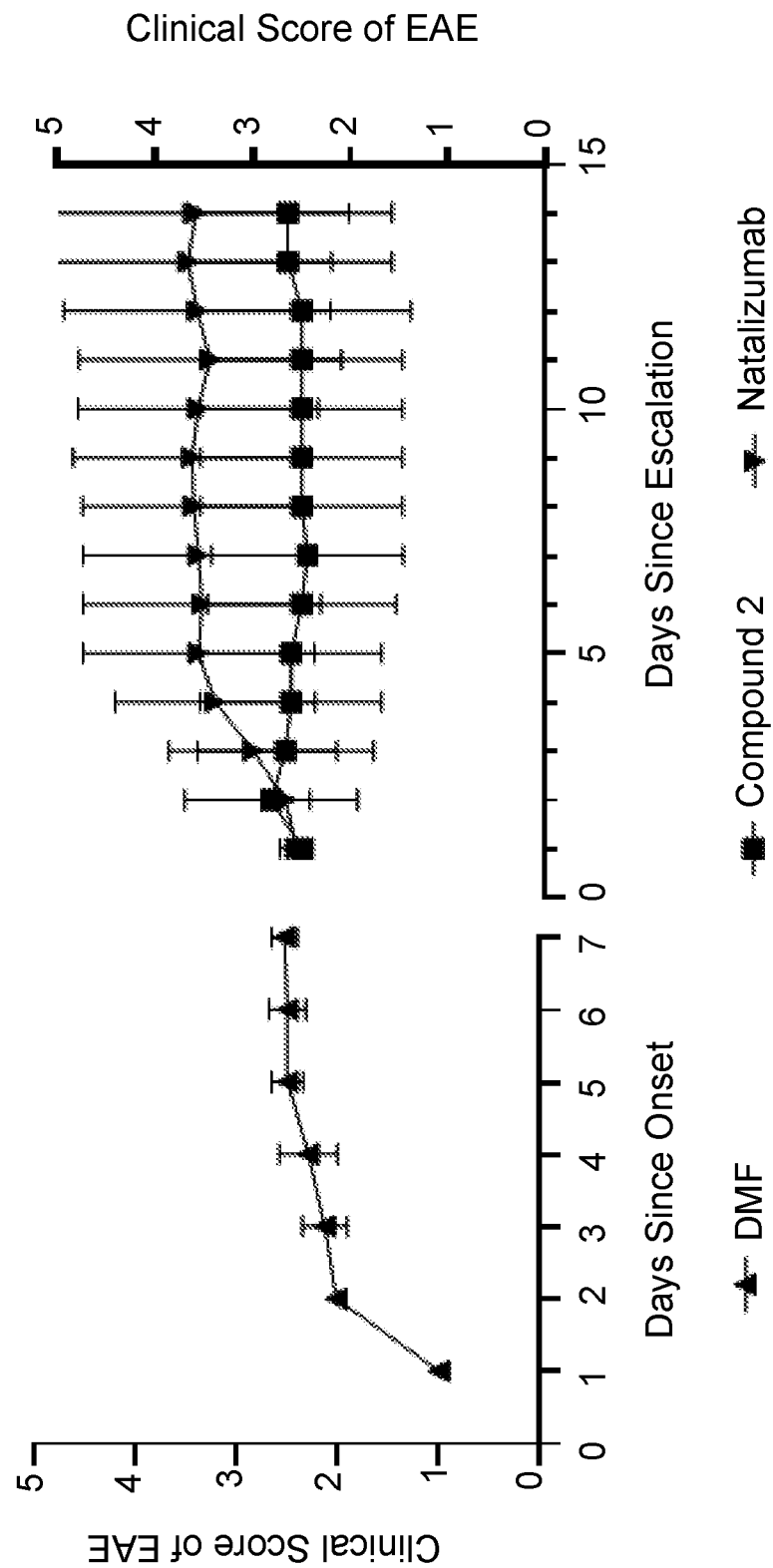
FIG. 5D shows therapeutic effects of Compound 2 versus natalizumab in a treatment escalation cohort from the study described in Example 8.

As seen in FIG. 5C, animals that continued DMF therapy progressed at the same rate as untreated control animals, with all animals reaching a clinical score of 5 by end of the study. In contrast, animals that were placed on Compound 2 treatment after disease onset had better overall disease control during therapy (day 1 to 14) and after stopping therapy (day 14 to end of study). As seen in FIG. 5D, animals switched from DMF to Compound 2 had a mean clinical score of 2.6 (SD=1.1) and a median score of 2.5 by day 14 after switching. Animals switch from DMF to natalizumab had a mean clinical score of 3.6 (SD=1.6) and a median of 3.75 after switching.

Figure 5E:
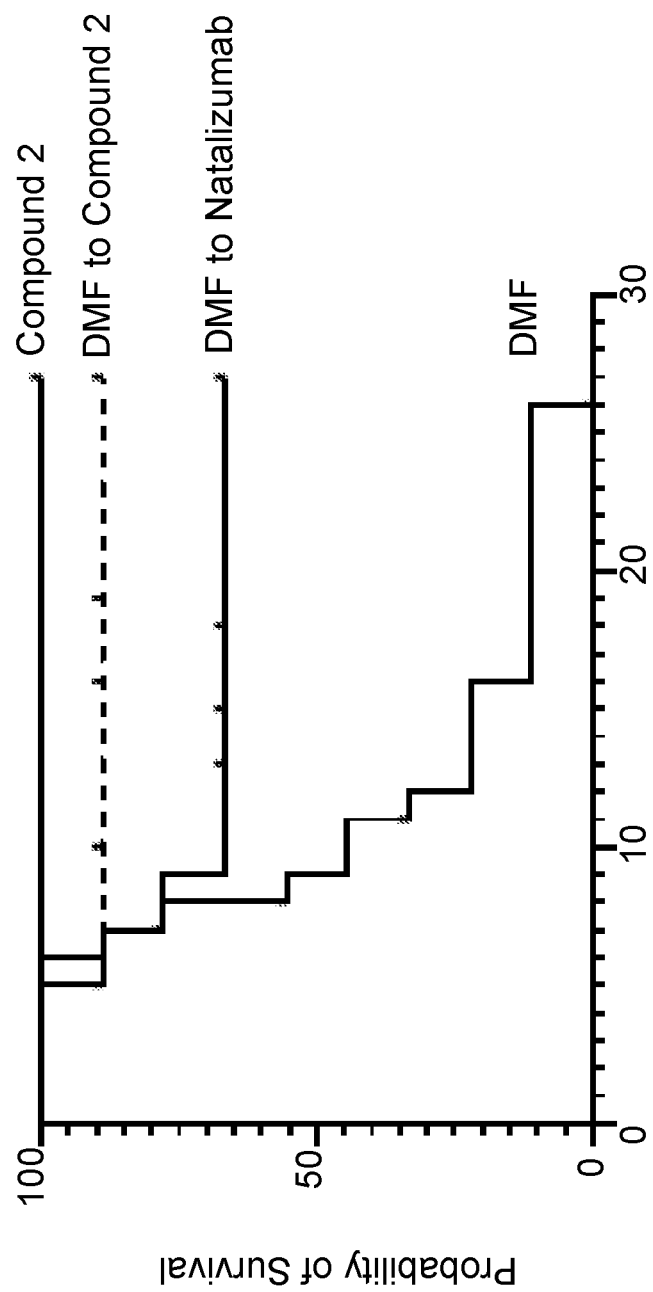
FIG. 5E shows overall survival of the various treatment groups from the study described in Example 8.

Animals treated with Compound 2 had a better overall survival regardless of the cohort (early sustained use or escalation cohort). In the early sustained use, all animals treated with Compound 2 survived until day 27. In contrast, all animals in the DMF-treated group died by day 26 (FIG. 5E). In the escalation cohort, 8 out of 9 animals that switched from DMF to Compound 2 survived until day 27 versus 6 out of 9 animals that switched from DMF to natalizumab.

The clinical management of MS patients currently follows one of two paradigms: the escalation paradigm or the induction/maintenance paradigm. In the escalation paradigm, medication of increasing efficacy and potency (and with greater risks of serious adverse events) are given following treatment failure with a lower-potency and lower-efficacy medication. High-potency disease-modifying therapies (DMT) include natalizumab, alemtuzumab, anti-B-cell and mitoxantrone. Lower efficacy therapies include glatiramer acetate, interferon beta, teriflunimide, DMF and fingolimob. Typically, treatment in the escalation treatment paradigm begins with treatment with glatiramer acetate, interferon beta and/or teriflunimude, is escalated upon treatment failure to fingolimod and/or dimethyl fumarate, is further escalated upon treatment failure to natalizumab and/or anti-B-cell, and is yet further escalated upon treatment failure to alemtuzumab and/or mitoxantrone.

Often, DMTs are reserved for subjects that have failed at least one or two low efficacy therapies. This is mainly driven by the risk/benefit of the high-potency DMT in mild cases. The main issue with this paradigm is the high failure rate and intolerability of the older and less potent DMTs and injectables. Furthermore, treatment with a low potency drug early means missing an opportunity for disease control early on.

There is a clinical need for a high efficacy molecule with a favorable safety/tolerability profile for early sustained use. Compound 2 has been shown to be a high efficacy molecule. Furthermore, the mechanism of action of Compound 2, which is hypothesized to be immune tolerance restoration, is expected to offer a better overall safety profile compared to immune modulators/suppressants.

Due to the rapid disease progression in the MOG EAE model in mice, a full escalation paradigm like the one currently used clinically and described above is not possible. A shorter version of the paradigm with only two escalation steps was used instead.

It is noteworthy that many published EAE models are performed prophylactically. In a prophylactic model, animals are treated after immunization but before any clinical symptoms are observed. In the EAE study described in this example, treatment was performed therapeutically, after disease symptoms appeared. This difference may explain the poor performance of therapies like glatiramer acetate and DMF in the models described herein; it also highlights the superior efficacy of Compound 2.

This study showed that early sustained use of Compound 2 was superior to DMF, and prevented disease escalation and improved overall survival better than DMF. Furthermore, switching from DMF after disease escalation to Compound 2 resulted in better disease control and improved overall survival compared to switching to natalizumab after DMF.

Example 9. Evaluating the Therapeutic Effects of Compound 2 in an Induction/Maintenance Treatment Paradigm in $MOG_{35-55}$-Induced Murine EAE Model The data in Example 8 suggested treatment with Compound 2 was superior to treatment with DMF in controlling disease and preventing symptom escalation when started at the onset of symptoms. Furthermore, Compound 2 was superior to natalizumab after disease control failure with DMF.

An emerging clinical treatment paradigm is the induction/maintenance treatment paradigm. In this paradigm, high potency disease-modifying therapies (DMTs) are used to induce disease control (induction phase) followed by a switch to safer, maintenance therapy (maintenance phase). In this study, the use of Compound 2 versus natalizumab during the induction phase was evaluated, as was use of Compound 2 versus DMF during the maintenance phase of treatment.

All animal studies were conducted in compliance with Tufts University/Tufts Medical Center & Human Nutrition Research Center on Aging. Animals were housed five in a cage and had access to food and water ad libitum.

Table 7 (see Example 8) lists materials and reagents used in this experiment. Compound 2, natalizumab and DMF were prepared as described in Example 8. Table 5 (see Example 4) details the expected clinical symptoms and scoring criteria used in this study.

This study was designed to evaluate the therapeutic effects of Compound 2 versus natalizumab in a treatment induction/maintenance paradigm (induction cohort), and Compound 2 versus DMF after natalizumab (maintenance cohort). In the induction cohorts, animals were randomized 2:1:1 natalizumab:Compound 2:control when they reached a score of 2.5, as per FIG. 6A. Animals in the natalizumab cohort were given 100 µg natalizumab/mouse every 3 days for 3 doses before being randomized to the maintenance cohort. Animals randomized into the maintenance cohort after natalizumab received maintenance doses of DMF or Compound 2 (1:1 randomization), as per their group assignment for 14 days. Animals in the Compound 2 induction cohort were dosed with 30 µg Compound 2/mouse SC QD for a maximum of 7 days, or 3 consecutive days of disease score <2.5, at which time they were placed on a maintenance dose of 3 µg/mouse SC QD for 14 days. All animals in all groups were monitored for 14 days after the last dose for disease score and survival.

Disease control (induction therapy): Disease control was defined as maintaining a clinical score of 2.5 or less after randomization. Animals in the different treatment groups were monitored after the 2:1:1 randomization. Clinical scores were recorded daily for all animals and plotted over time. A score of >2.5 was recorded as an event and analyzed by survival analysis in GraphPad Prism 9. Animals not reaching a clinical score of 2.5 by the end of the induction period (day 7) were assigned a score of zero for the survival analysis.

Survival (induction therapy): Death due to disease (clinical score 5) during the treatment induction period was recorded as an event "1", animals surviving until the end of the induction period, day 7 after randomization, were censored on day 7 for the purposes of survival analysis.

Disease control (maintenance therapy): At the end of the induction period with natalizumab, animals were randomized 1:1 to the DMF maintenance group or Compound 2 maintenance group as per FIG. 6A. Animals were dosed for 14 days, and clinical scores were monitored daily.

Survival (maintenance therapy): Death by disease (clinical score of 5) was recorded as an event "1", death due to ulceration or ex vivo analysis was recorded as "0". Animals surviving until the end of the study were recorded as "0" on the last day of the study. Survival analysis was done in GraphPad Prism 9.

Figure 6A:
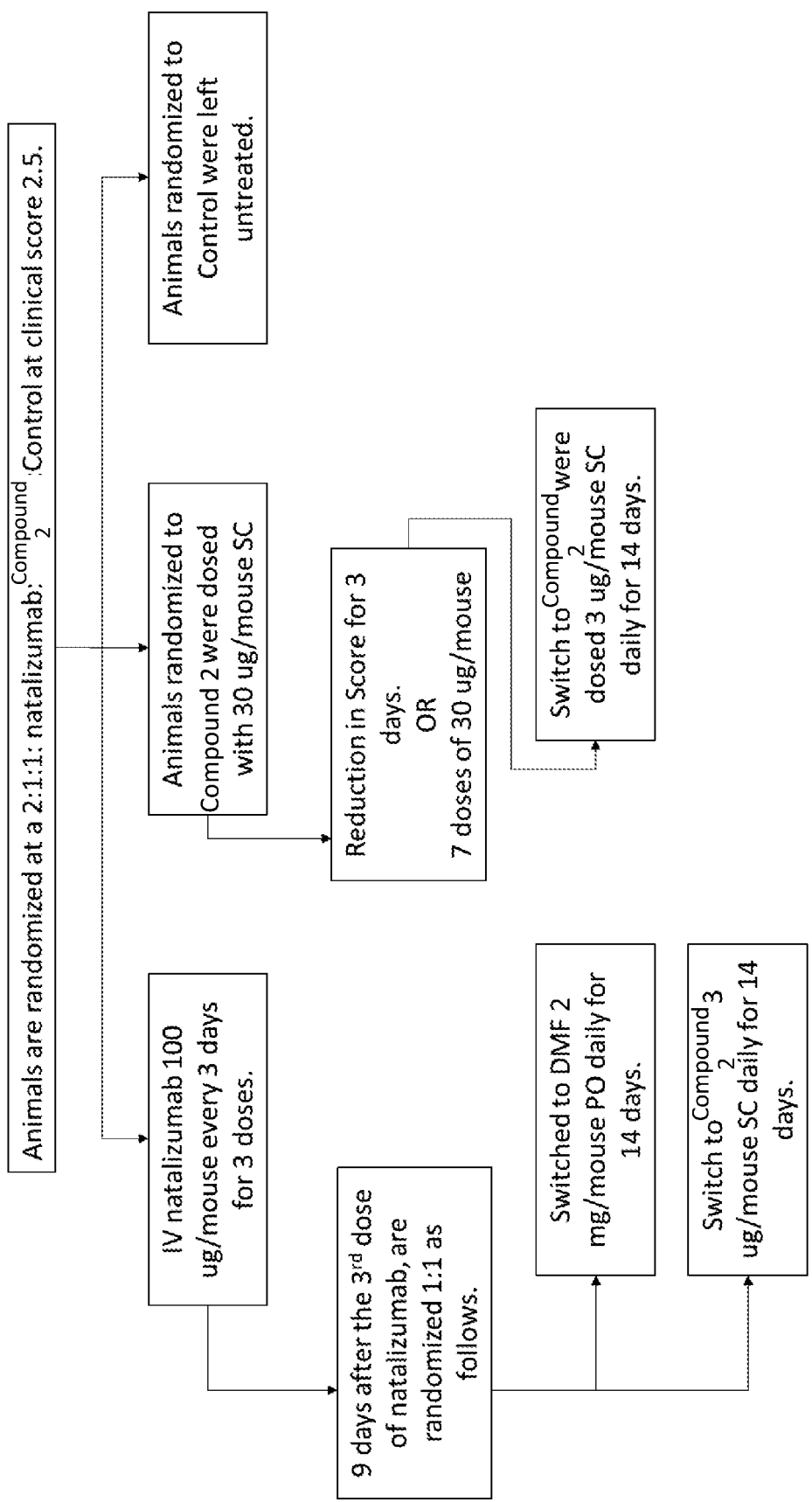
FIG. 6A shows the study design and randomization schedule of the study described in Example 9.

Results: Disease incidence in this study was 97% (87/90 mice). Disease onset started on day 9 after immunization. Animals were randomized into treatment groups when they reached a disease score of "2.5," as shown in FIG. 6A. All animals were assigned a treatment group by day 15 after immunization.

IACUC guidelines mandate that animals with immunization site ulcerations be put down. If the animal was assigned a treatment group, the data from that animal were used in the calculation of the average clinical score until the day the animal was put down. Euthanasia due to immunization site ulcerations was not assigned a clinical score of "5".

Figure 6B:
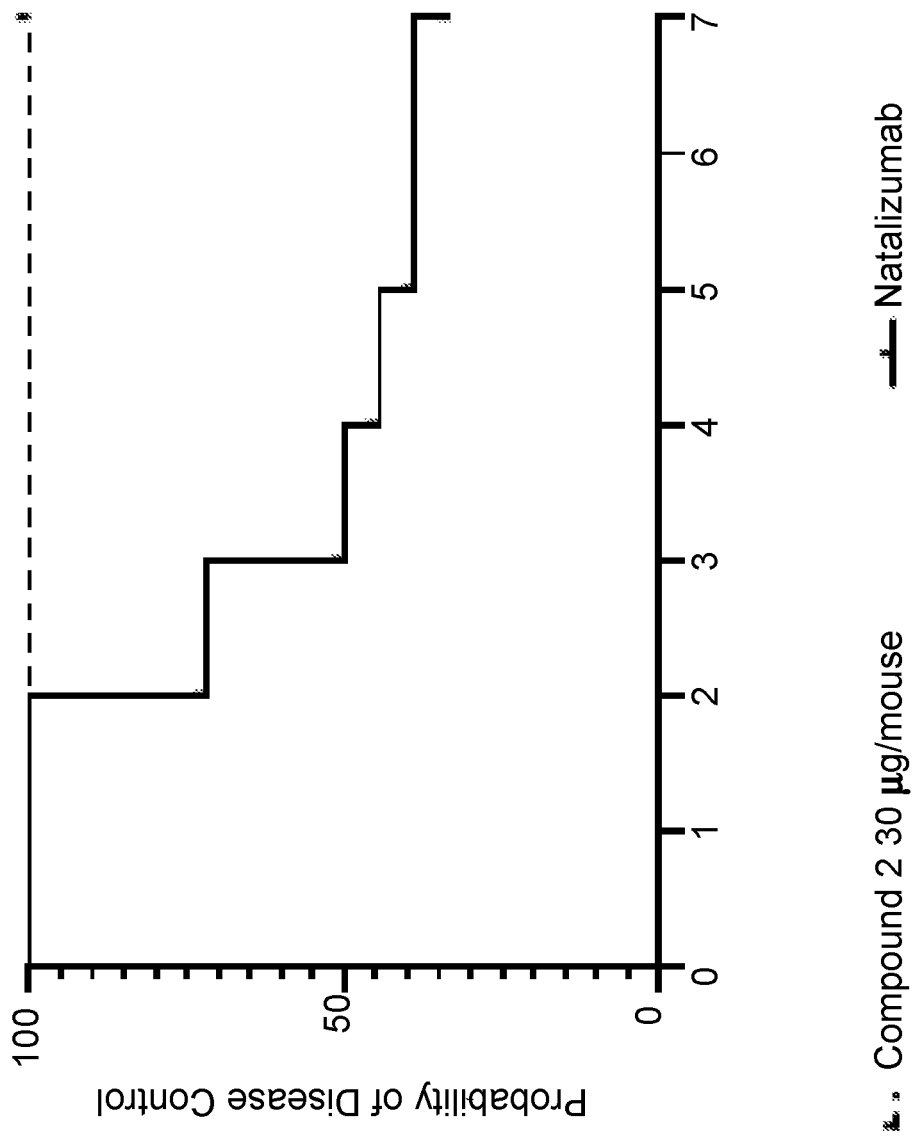
FIG. 6B shows probability of disease control (score <2.5) in treatment groups on induction therapy from the study described in Example 9.
Figure 6C:
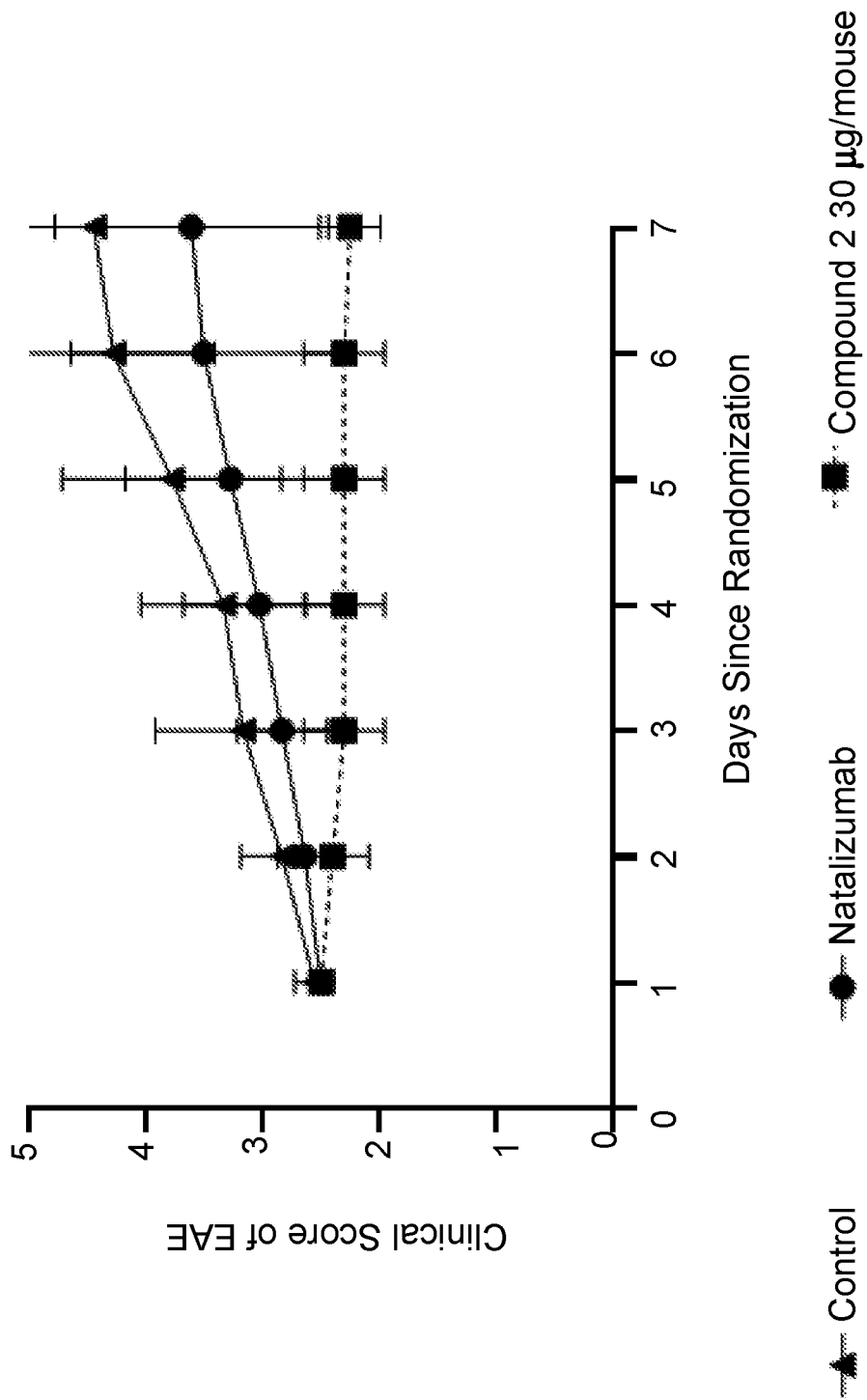
FIG. 6C shows clinical score in treatment groups on induction therapy from the study described in Example 9.
Figure 6D:
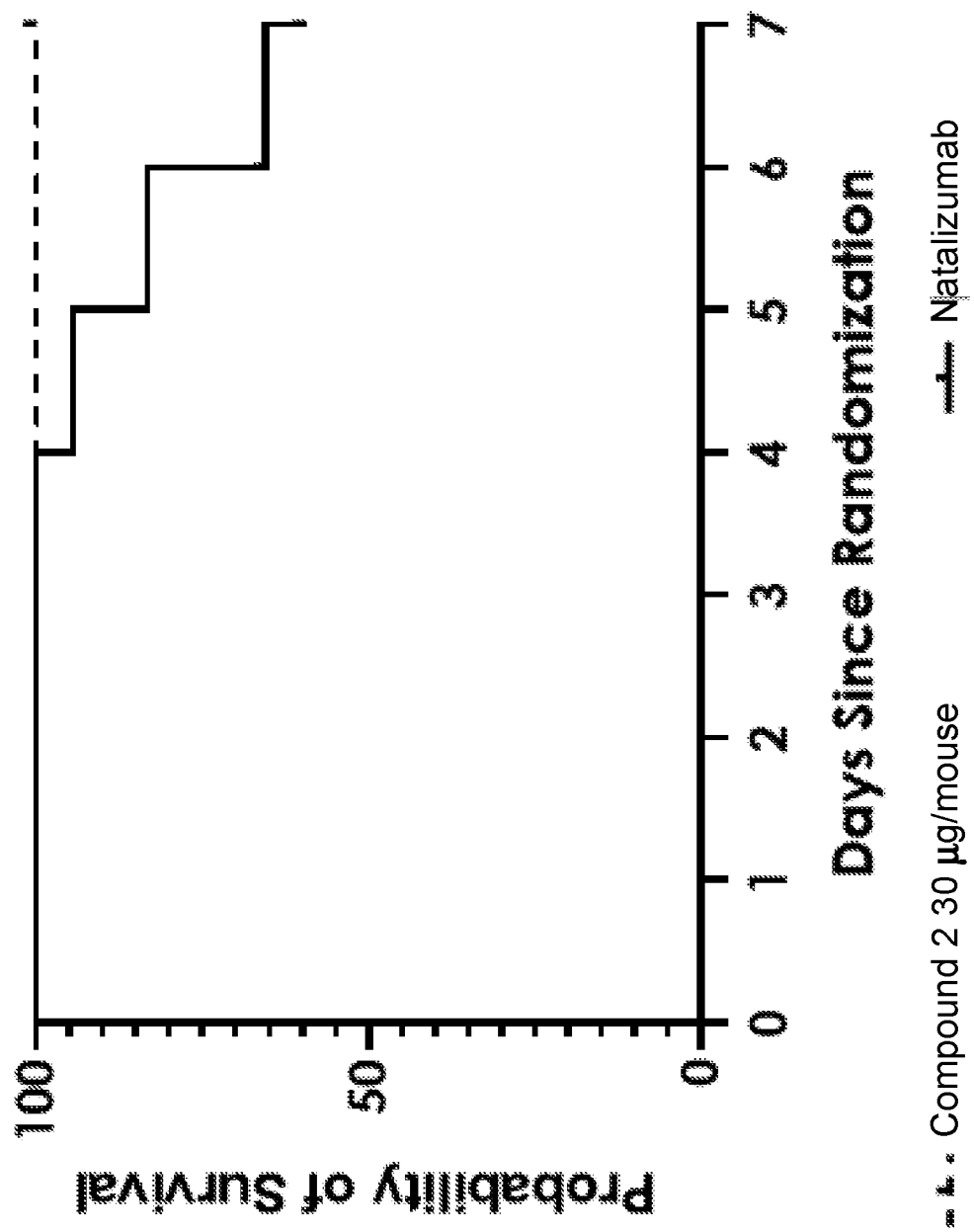
FIG. 6D shows survival in the treatment groups at the end of the induction therapy period from the study described in Example 9.

Animals were randomized at a clinical score of 2.5. A total of 18 mice were randomized to the natalizumab group, 9 mice were randomized to the untreated control group, and 10 mice to the 30 µg/mouse Compound 2 group (2:1:1 randomization). Of the 18 animals in the natalizumab group, 12 animals progressed to a clinical score >2.5. In contrast, 0/10 animals in the Compound 2 (30 µg SC group) progressed to a score >2.5 (FIG. 6B). The mean clinical score by day 7 was 4.44 (SD=0.85), 3.61 (SD=1.17) and 2.25 (SD=0.26) for the untreated control, natalizumab, and Compound 2 30 µg SC groups, respectively (FIG. 6C). Of the 18 animals that were randomized to the natalizumab group, 11/18 survived the treatment induction period. Of the 9 animals that were randomized to the Compound 2 30 µg SC group, 9/9 survived the induction period.

Figure 6E:
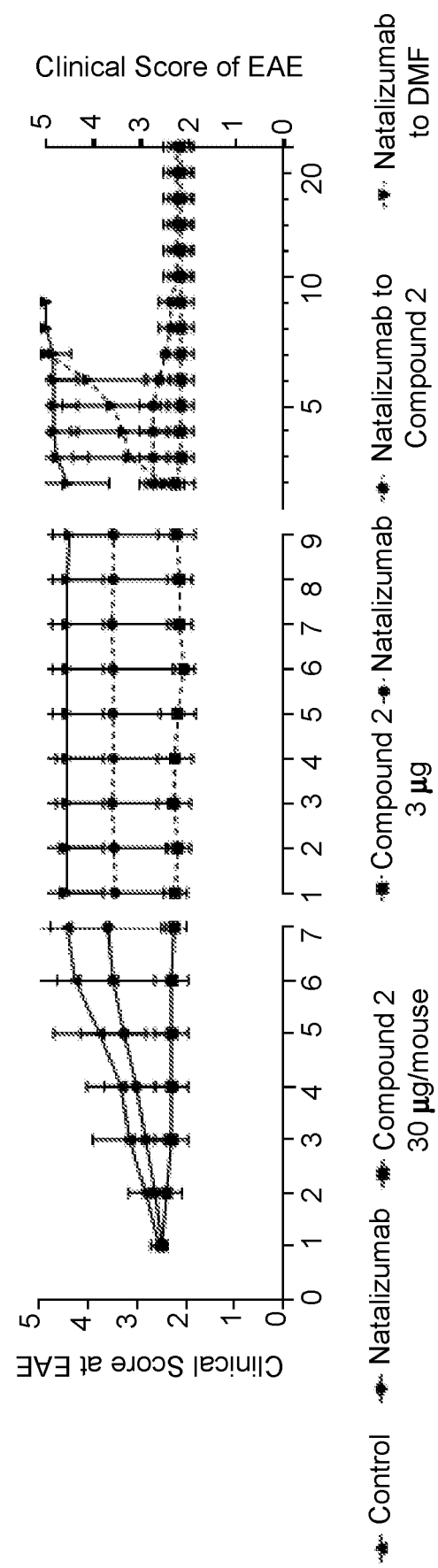
FIG. 6E shows therapeutic effects of Compound 2 versus natalizumab induction therapy followed by the indicated maintenance therapy from the study described in Example 9.

Of the 11 animals in the natalizumab group that survived the induction period, 4 were randomized to the DMF maintenance group and 4 to the Compound 2 group. The mean clinical score of animals randomized to the DMF and Compound 2 maintenance therapies was 2.5 (SD=0.4) and 2.8 (SD=0.3), respectively. The last measured score in the DMF maintenance group (day 7 after initiation of DMF maintenance) was 4.37 (SD=1.2). The last measured score in the Compound 2 group measured on day 7 after initiation of Compound 2 maintenance was 2.5 (SD=0). Animals in the Compound 2 maintenance group were monitored until the end of the 14-day dosing period. The mean clinical score at the end of day 14 was 2.3 (SD=0.3) (FIG. 6E).

All 9 animals randomized to the Compound 2 induction group were switched to Compound 2 maintenance therapy. The mean score on the first day of maintenance therapy was 2.3 (SD=0.4). The clinical score was stable throughout the maintenance treatment period—the clinical score recorded on the last day of dosing with Compound 2 was 2.2 (SD=0.3).

Figure 6F:
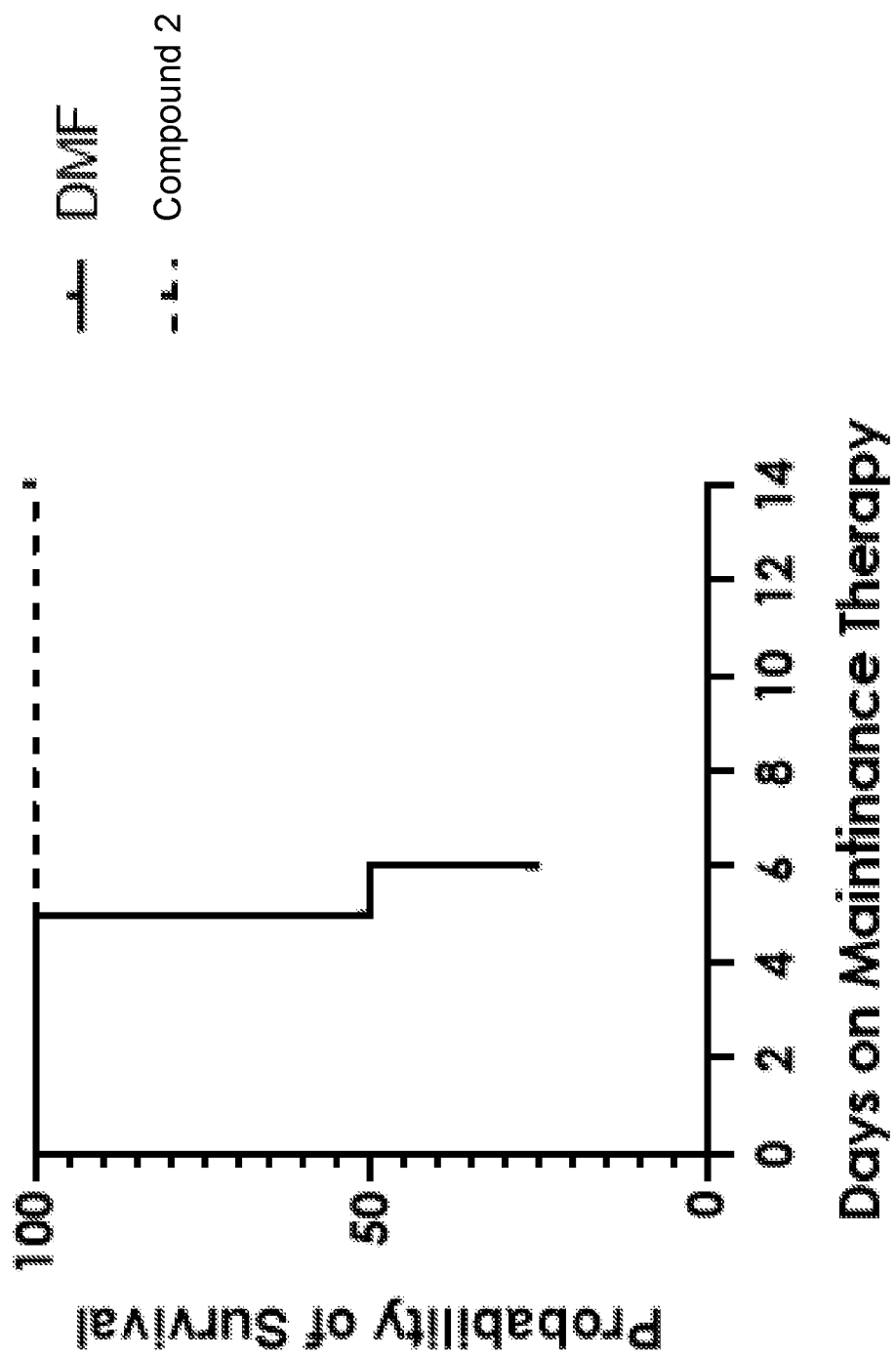
FIG. 6F shows overall survival in the maintenance cohorts from the study described in Example 9.

Of the animals randomized to the DMF maintenance after natalizumab induction, 3 out of 4 animals progressed to clinical score 5 (death by disease). All animals randomized to Compound 2 maintenance after natalizumab induction survived until the end of the study (FIG. 6F).

The induction/maintenance treatment paradigm in the management of MS is an emerging one. Patients with aggressive disease are placed on high potency (and less safe) DMTs to induce disease control followed by a switch to safer maintenance therapies. In this study, the therapeutic effects of Compound 2 were evaluated during both the induction phase versus natalizumab and the maintenance phase versus DMF. Furthermore, the effects of sustained use of Compound 2 were evaluated as both the induction and maintenance drug by varying the dose between the induction phase and the maintenance phase.

To mimic an aggressive disease that justifies an induction/maintenance paradigm, animals were allowed to reach a clinical score of 2.5 before randomization as per FIG. 6A. High-dose Compound 2 (30 µg/mouse SC) was superior to natalizumab in disease control and prevention of escalation during the induction period. Furthermore, the average clinical score in animals treated with Compound 2 dropped during the induction period in at least 4 out of the 10 mice randomized to Compound 2, showing clinical score improvement, and were switched to maintenance doses of Compound 2 before the end of treatment induction period, compared to 0/18 in the natalizumab group.

Surprisingly, 38.8% of mice randomized to the natalizumab induction therapy died before completing the induction therapy. This unexpected result meant that a smaller number of animals were available to randomize to the DMF or Compound 2 maintenance cohort. However, the 1:1 randomization resulted in n=4 in each group. Animals placed on DMF maintenance therapy had a mortality rate of 75% versus a mortality rate of 0% in the Compound 2 maintenance cohort. Furthermore, the clinical score in animals randomized to the Compound 2 maintenance cohort improved from 2.8 at the start of maintenance to 2.2 by the end of 14 days. This observation is in line with earlier studies showing Compound 2 can reduce clinical scores in animals with a prolonged stable high score.

Results in this study show that early sustained use of Compound 2 as both an induction and a maintenance drug can replace current induction/maintenance regimens. Furthermore, Compound 2 is a high efficacy molecule that can replace low efficacy maintenance therapy after high efficacy DMT, such as natalizumab. Overall, treatment with Compound 2 resulted in better disease control, improved clinical scores, and better survival regardless of regimen or sequence when compared to regimens lacking Compound 2 arms.

Example 10. Use of Compound 2 in Myasthenia Gravis (MG)

In this passive MG model in B6 mice, donor mice (n=20, aged 6-8 weeks) were immunized with complete Freund's adjuvant (CFA) and nicotinic acetylcholine receptor (AChR) emulsion weekly for four weeks. Seven days after the last immunization, splenocytes were collected, and $10^6$ cells/mouse were transferred to RAG2-/- mice. The recipient mice (n=10/group) were treated one day after adoptive transfer with prednisone (1 µg/mouse) SC daily for ten days after disease onset or Compound 2 3 µg SC daily for ten days after disease onset, or were left untreated. Minimal manifestation of disease was defined as a return to a clinical score of 1 after an exacerbation (score 2 or higher). Time to return to minimal score was logged, and the likelihood of return was plotted for untreated animals, and standard of care (SOC; prednisone)- and Compound 2-treated animals.

Figure 7:
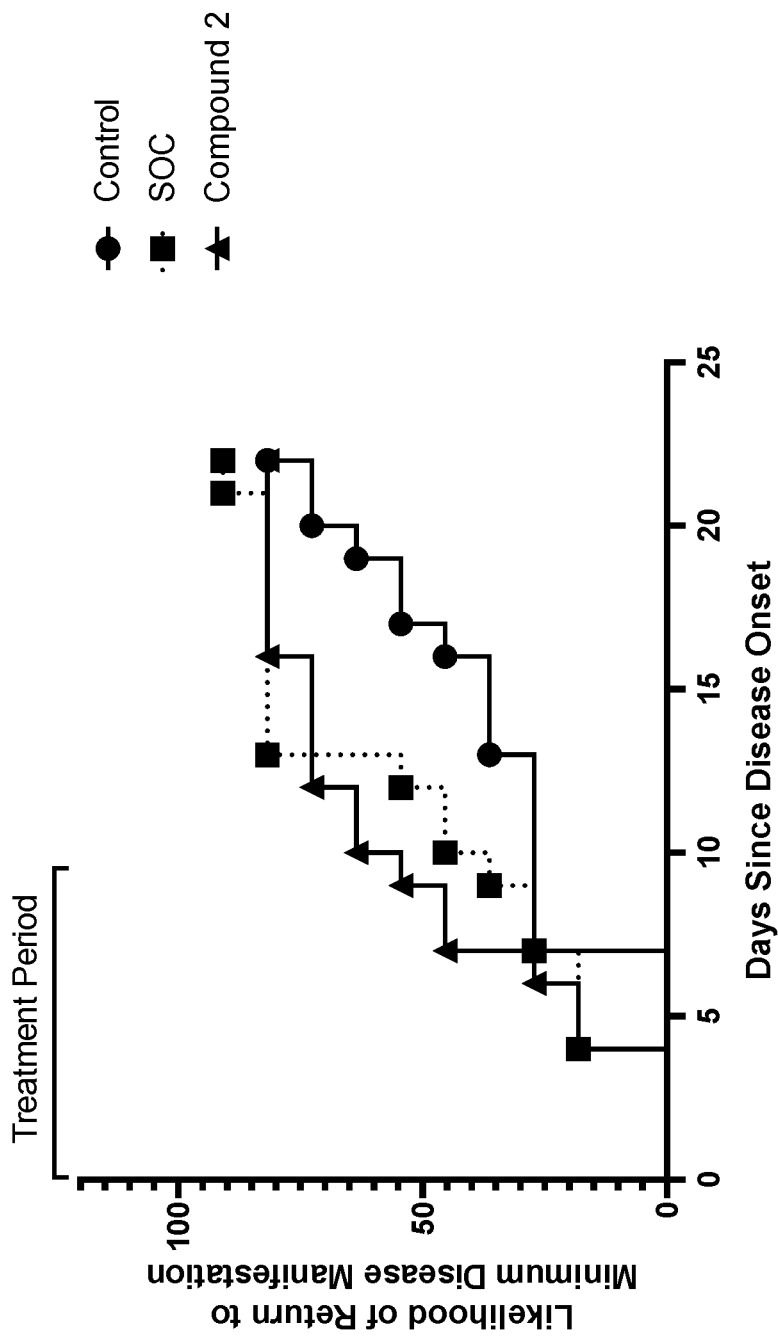
FIG. 7 shows likelihood of return to minimal manifestation of disease for the treatment groups from the study described in Example 10.

The results are depicted in FIG. 7. By day 10, 63% of animals treated with Compound 2 returned to minimal manifestation of disease (score 1) versus 46% for SOC (prednisone)-treated and 28% for untreated animals.

Example 11. Use of Compound 2 in Neuromyelitis Optica (NMO)

NMO is a CNS autoimmune inflammatory demyelinating disease that causes optico-spinal disorder leading to paralysis and vision loss. NMO mouse model was established by using AQP4-p201-p220 peptide (from Genemed Synthesis Inc.). Briefly, $C_{57}BL/6$ mice (n=30) were immunized on day 0 with 100 micrograms of the AQP4-p201-p220 peptide emulsified in CFA. Mice were injected subcutaneously at the tail base under anesthesia. On the day of injection (Day 0) and two days later, mice received intraperitoneal injection of pertussis toxin (PTx) in PBS at 200 ng/mouse/dose (0.1 ml).

Prior to immunizing the mice on day 0, both eyes of each of the mice were imaged by fundoscopy. Fundoscopy was employed to study (a) optic disc inflammation, and (b) retinal damage (exudates as evidence of inflammation). Mice were monitored for disease onset daily after one week of immunization (day 7) for clinical symptoms, as per the scoring system developed by Ramadan et al., Brain 2016. Mice with a score of 1.0 or any optimal symptoms were immediately randomized into either group A or group B treatment regimens to receive up to 14 days of treatment. Group A (n=10) received Compound 2 3 µg SC daily, and Group B (n=8) served as a control and was treated with a placebo.

Fundoscopy was conducted on day 6 post-immunization and was later performed approximately once every four days, i.e., on days 9, 13, 16, 22, and 26. Each eye was scored for inflammation in the optic disc and retinal damage evident by the appearance of 'exudates' (blotchiness) in the fundus image. Eye samples were collected during the onset of disease and post-randomization after at least 9-12 days of treatment and on day 14 (end of study) to assess the histology of both the optic nerve and the retina.

Exudate, a symptom of inflammation, was the most common finding in the pilot study. While NMO is an optic nerve disease, exudates have been reported clinically in the retina of patients suffering from NMO. The MS-like clinical symptoms in NMO are mild in general, and in this study, the scores were quite mild. Table 8 summarizes the outcome of the study.

TABLE 8

Summary of the Study

| NMO eyes status since randomization | Placebo Group (n = 8) | Compound 2 Group (n = 10) |
|---|---|---|
| Total number of eyes in the study | 16 | 20 |
| Cleared/Clearing eyes (recovery) | 0 | 4 |
| Maintained/No change | 9 | 14 |
| Worsening conditions | 3 | 0 |
| Eyes not counted since not treated for at least one week | 2 | 2 |
| Eyes with no data due to opacity | 2 | 0 |

Example 12. Therapeutic Effects of Compound 2 and Compound 8 in $MOG_{35-55}$-Induced Murine EAE Model Mice were immunized with 100 µg $MOG_{35-55}$ emulsified with CFA and pertussis toxin, as described in Example 4. At disease onset (clinical score 1), mice were randomized into two treatment groups, and received 3 µg/mouse/day SC of either Compound 2 or Compound 8.

Figure 8:
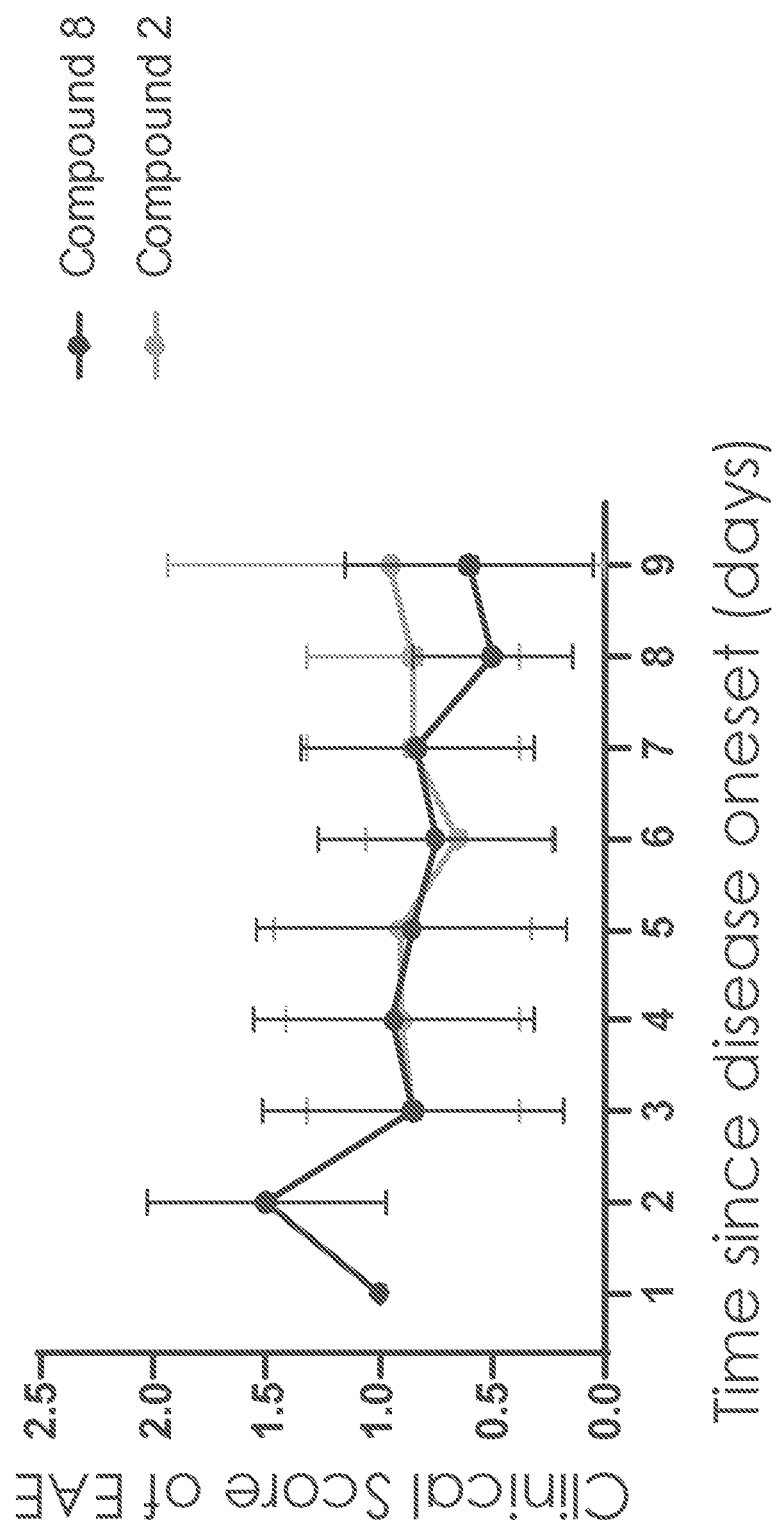
FIG. 8 shows the mean clinical score of mice treated with Compound 2 or Compound 8 in the murine EAE model described in Example 12.

FIG. 8 shows that after ten days of treatment, no statistical difference between the Compound 2 and Compound 8 groups was observed.

Example 13. Pristane-Induced Lupus Model

Four-week old female Balb/c mice received 0.5 ml IP injection of pristane (Sigma Aldrich). Eight weeks post pristane injection, all mice tested positive for anti-dsDNA antibody titers (FUJIFILM Wako Pure Chemical Corporation), indicating systemic disease onset. On Day 60, mice were randomized to treatment (n=12) (Compound 2, 3 µg SC daily) or control group (n=11), and treatment was started. Mice were monitored daily for cutaneous lupus symptoms by checking for the appearance of skin lesions.

Figure 9:
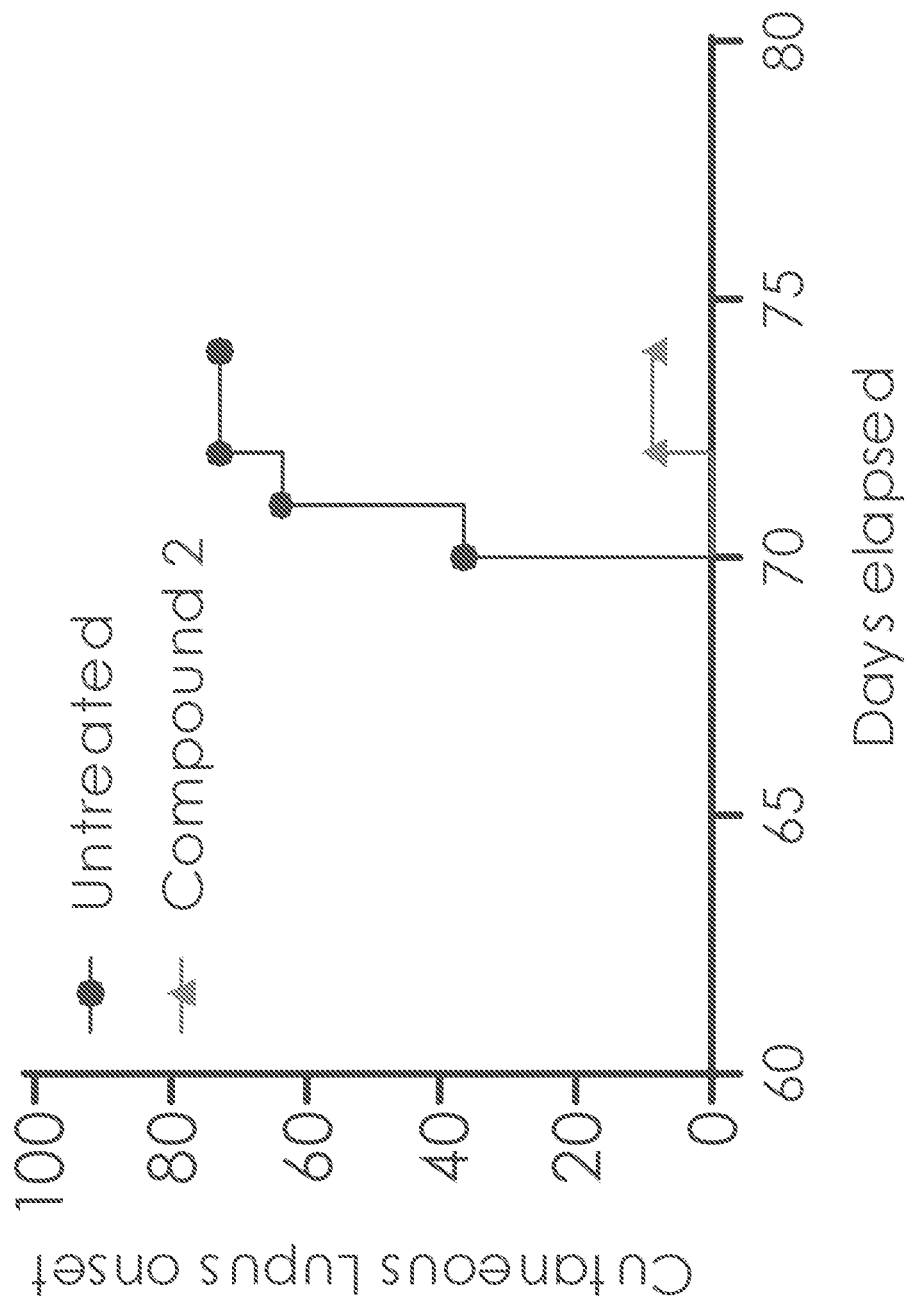
FIG. 9 is a graph of percentage of mice with cutaneous lupus onset versus days elapsed, and shows cutaneous lupus onset in the untreated control group and Compound 2-treated group from the pristine-induced lupus model described in Example 13.

Interim data from the study are shown in FIG. 9. While the study is ongoing, after two weeks of treatment, mice treated with Compound 2 had lower incidence of cutaneous lupus in comparison to untreated control (8% versus 73%, respectively). In addition, the onset of cutaneous symptoms was delayed by two days in Compound 2-treated mice compared to untreated control mice.

Example 14. Dextran Sulfate Sodium (DSS)-Induced IBD Model

IBD was induced in 6-8-week-old female $C_{57}/B6$ mice by adding 3% DSS (Sigma Aldrich) in their drinking water for 3 days on 2 different occasions (days 0, 1, and 2 of the induction phase and days 11, 12, and 13 of the re-exposure phase). One group (n=5) was treated with Compound 2 (30 µg SC for 7 days) during the disease induction phase followed by a lower dose of Compound 2 (3 µg SC for 7 days) during the disease re-exposure phase. The control group (n=5) did not receive any treatment. Mice body weight was monitored daily starting on day 0.

Figure 10:
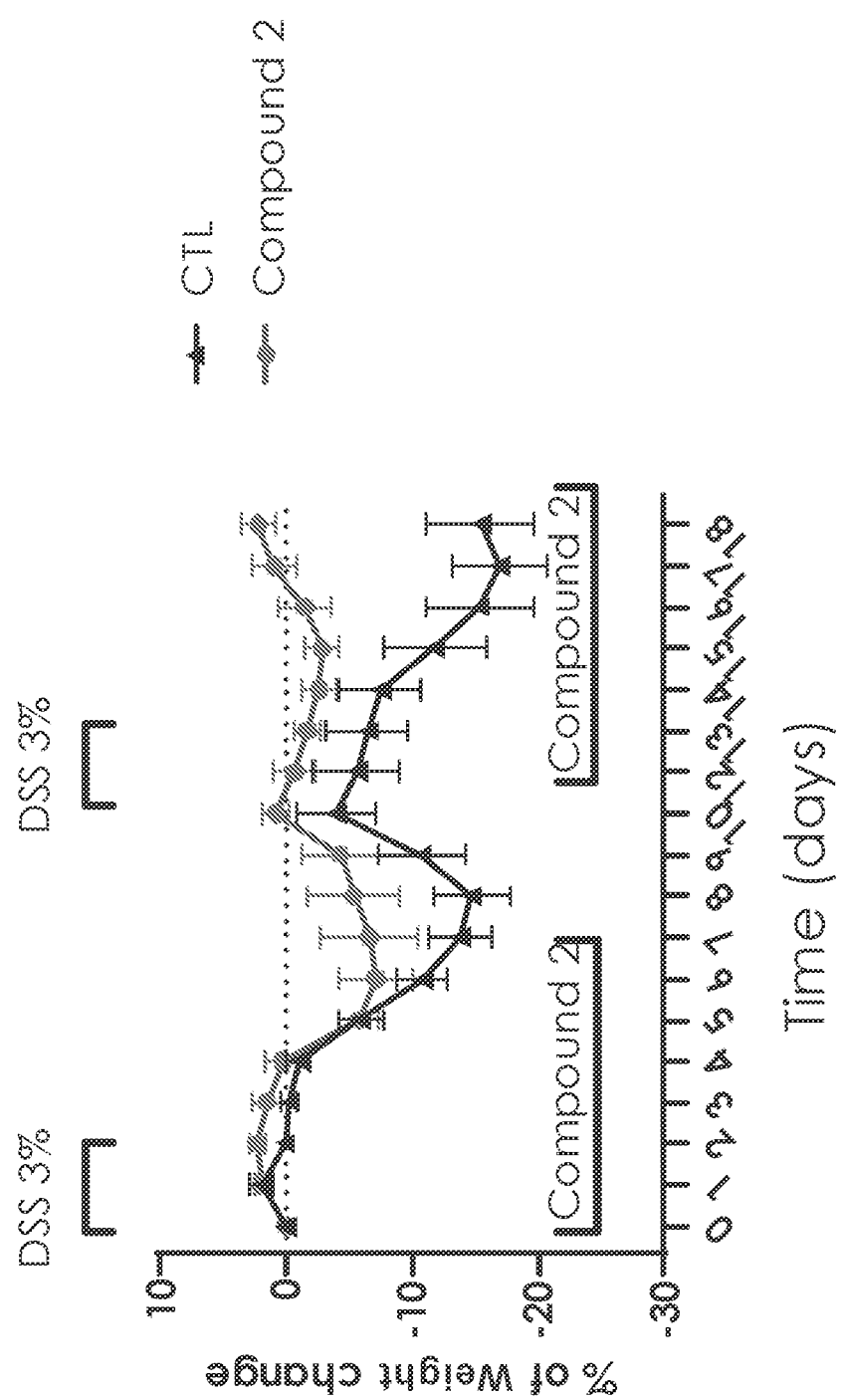
FIG. 10 shows percentage of weight change over time in the untreated control group and Compound 2-treated group from the dextran sulfate sodium (DSS)-induced IBD model described in Example 14.

As shown in FIG. 10, in both disease cycles, animals treated with Compound 2 had less weight loss and more rapid recovery than untreated animals, suggesting Compound 2 could be an effective treatment for IBD.

Example 15. Phase I Clinical Trial

A placebo-controlled study in healthy adult volunteers and adult subjects with confirmed diagnosis of primary progressive multiple sclerosis (PPMS), relapse remitting multiple sclerosis (RRMS), neuromyelitis optica (NMO), and myelin oligodendrocyte glycoprotein antibody disease (MOGAD) is to evaluate safety, tolerability, and pharmacokinetics after single and multiple doses of Compound 2 and pharmacodynamic and early response in these subjects after 12 weeks of oral dosing with Compound 2. The primary objectives of the study are to: (1) evaluate safety and tolerability of Compound 2 after single ascending oral doses of Compound 2 in healthy adult volunteers, and (2) evaluate safety and tolerability of Compound 2 after single ascending/multiple ascending oral doses of Compound 2 in adult subjects with PPMS, RRMS, NMO or MOGAD. The secondard objectives of the study are to: (1) evaluate the pharmacokinetics after single ascending oral doses of Compound 2 in healthy adult volunteers, and (2) evaluate the pharmacokinetics after single ascending/multiple ascending oral doses of Compound 2 in adult subjects with PPMS, RRMS, NMO, or MOGAD.

This is a single-blinded, single ascending dose/multiple ascending doses (SAD/MAD) phase I study in healthy volunteers and subjects with PPMS, RRMS, NMO, or MOGAD. The phase I SAD will consist of six cohorts of eight subjects each (6+2 treatment+placebo enrolled in a 1:1 and 1:4 design). Cohorts 1, 2 and 3 will enroll healthy volunteers. Cohorts 4 and 5 will enroll subjects with PPMS or RRMS. Cohort 6 may enroll healthy volunteers or subjects with PPMS or RRMS.

Phase I MAD will be initiated after cohort 3 SAD has cleared. The MAD portion of the study will consist of three cohorts of 10 subject in each cohort with RRMS or PPMS. Subjects will be dosed daily for up to 28 days. Subjects will be allowed to maintain their concomitant MS medication during the MAD portion of the study.

Healthy volunteers will be administered a single dose of Compound 2 as per cohort assignment. Healthy volunteer involvement in the study will conclude after 14 days of follow-up, or as appropriate for SAD study. Subjects with RRMS or PPMS will be administered a single oral dose of Compound 2 during the SAD portion of the study, and daily oral doses of Compound 2 for up to 28 days during the MAD portion of the study. RRMS and PPMS subjects will be allowed to continue their MS medication during this phase of the study. Subjects in the MAD portion of the study will have the choice to continue in the Phase Ib study. Subjects not wishing to continue will be discharged from the study after a follow-up period (e.g., of 30 days, six months). Projected dosing for the phase I SAD/MAD study is shown in Table 9.

TABLE 9

Projected Dosing Per Cohort

| Cohort | Dose |
| --- | --- |
| 1 (Healthy volunteers) | 15 mg |
| 2 (Healthy volunteers) | 30 mg |
| 3 (Healthy volunteers) | 50 mg |
| 4 (MS patients) | 100 mg |
| 5 (MS patients) | 125 mg |
| 6 (MS patients) | 150 mg |

The safety and tolerability of Compound 2 will be evaluated based on recorded adverse events (AEs), physical examinations, vital sign measurements, electrocardiograms, and clinical laboratory assessments. Adverse events will be coded using the Medical Dictionary for Regulatory Activities (MedDRA). Adverse events and clinical laboratory values will be graded using NCI CTCAE v5.0. Blood/plasma samples will be collected at specified time points to assess the pharmacokinetics of Compound 2 using validated liquid chromatography-mass spectrometry/mass spectrometry (LC-MS/MS) assays.

Inclusion criteria include:
1. Subject, or their legally authorized representative, must be willing and able to provide appropriate written informed consent.
2. Healthy volunteers with no known acute or chronic medical conditions (respiratory, gastrointestinal, renal, hepatic, hematological, lymphatic, neurological, cardiovascular, psychiatric, musculoskeletal, genitourinary, immunological, dermatological, endocrine, etc.) at the time of enrollment.
3. All males or non-pregnant females aged 18-70 years will be included in the study irrespective of their ethnicity, socioeconomic, or educational status.
4. Body Mass Index (BMI) 18.0-35.0 kg/m$^2$, inclusive (<56 years of age), at screening; BMI 18.0-30.0 kg/m$^2$, inclusive (>56 years of age), at screening.

5. Subjects with a confirmed diagnosis of PPMS or RRMS, by revised 2017 McDonald criteria.
6. Subjects with a confirmed diagnosis of NMO by neurological exam, Mill scan, and a positive autoantibody antibody NMO-IgG test.
7. Subjects with a confirmed diagnosis of MOGAD by meeting three of the following criteria: (a) laboratory finding: serum positive MOG-IgG by cell-based assay; (b) clinical findings of any of the following presentations:
   (i) ADEM;
   (ii) optic neuritis, including chronic relapsing optic neuropathy (CRION);
   (iii) transverse myelitis (short or long segment);
   (iv) brain or brainstem syndrome compatible with demyelination; or
   (v) any combination of the above.
8. Kurtzke Expanded Disability Status Scale (EDSS) score of between 0-9.5.
9. Subject must have undergone a 3T MRI brain and/or spinal cord within 6 months-1 year before enrollment.
10. Subjects who are willing and able to adhere to study protocol requirements including scheduled visits, maintaining a study drug diary, laboratory tests, and other study procedures such as EKG, 3T MRI brain and/or spinal cord, ophthalmic exam, etc.
11. Clinical laboratory evaluations performed in the past six months including the white blood cell (WBC), hemoglobin (Hgb), platelets (PLTs), alanine transaminase (ALT), aspartate transaminase (AST), alkaline phosphatase (ALP), total bilirubin (T. Bili), lipase, BUN, creatinine, prothrombin time (PT), and partial thromboplastin time (PTT) are within acceptable normal reference ranges (Grade-1 abnormality will be excluded from the study).
12. Female subjects in the reproductive age group and subjects with female partners of childbearing potential must agree to use an acceptable contraception method. This criterion must be followed from the time of the first dose of study medication until the follow-up visit (for subjects and their partners) and with an additional period of 90 days (for subjects themselves).

Exclusion criteria include:
1. Subjects diagnosed with CIS, which describes the first episode of neurological symptoms that last at least 24 hours caused by inflammation or demyelination in the central nervous system. It usually occurs in young adults and affects optic nerves, brainstem and/or spinal cord.
2. Blood loss of >250 mL or donated blood within 56 days, or donated plasma within 7 days, of study screening.
3. Subjects with a history of HIV or HIV-related disease conditions, hepatitis B or C, or other infectious diseases.
4. Subjects with Grade-3 lymphocytopenia (<500-200/mm$^3$ or <0.5-0.2*10e9/L) over the past 6 months.
5. Subjects who have been treated with immune depleting medications within the three months preceding blood collection for this study or before sample collection and processing for PBMCs or anticipating the need for immunosuppressive treatment within the next six months.
6. History of cancer treatment with either chemotherapy or radiation therapy or both in the past five years prior to enrollment in the study.
7. Subject has COVID-19 positive status (confirmed by clinical signs and symptoms and positive SARS-CoV-2 NAAT result COVID test) while enrolling in the trial or has had recent COVID-19 vaccination including booster dose in the past 30 days or has received anti-viral therapy intended to prevent COVID-19 such as paxlovid, remdesivir, molnupiravir, interferons, anti-SARS-CoV-2 monoclonal antibodies, IVIG-SARS-CoV-2, COVID-19 convalescent plasma, etc.
8. Recent vaccination with live attenuated vaccines such as influenza, MMR, herpes zoster, varicella, yellow fever, rotavirus vaccine, etc., or inactivated vaccines such as hepatitis A, rabies vaccine, etc. in the past 30 days.
9. Subject has participated in another investigational study involving any investigational product within 60 days, or 5 half-lives, whichever is longer, before the first vaccine administration study drug, biologic, or device.
10. Pregnant or lactating women or women currently undergoing infertility treatments or women who intend to become pregnant during the time of study enrollment.
11. Any psychiatric condition including recent (e.g., within one year of study enrollment) or active suicidal ideation/behavior or laboratory abnormality that may increase the risk of study participation or in the investigator's judgment make the subject inappropriate for the study.

A minimum of 54 subjects will be enrolled in the study: up to 24 healthy volunteers and 30 subjects with RRMS or PPMS (4:1 ratio). For the SAD study, approximately 12 to 24 healthy volunteers will be enrolled into each of cohorts 1, 2, and 3 in a 4:1 randomization treatment to placebo. The total sample size per cohort will be determined by dose limiting toxicities (DLTs). Between 12 to 24 subjects with RRMA and/or PPMA will be enrolled in Cohorts 4, 5, and 6 without randomization to dose. The total sample size per cohort will be determined by DLTs. For the MAD study, approximately 30 subjects with RRMS or PPMS will be enrolled into MAD cohorts 1, 2, and 3. Subjects will be randomized to achieve a 4:1 ratio of RRMS to PPMS in each cohort.

Example 16. Drug Product

Compounding is conducted in compliance with USP <795> guidelines. Briefly, compounding is conducted by transferring 24,000 mg of hydroxypropyl beta cyclodextrin (HPBCD) and 300 mg of Compound 2 into a suitable container. Approximately 100 mL of water is added to the container, followed by alternating periods of stirring and sonication until a clear solution is achieved. The final preparation is transferred to a PET container for clinical use.

Oral dosing solutions of different concentrations of Compound 2 were compounded ranging from 0.02 mg/ml to 3 mg/ml using a 1:80 ratio of Compound 2:HPBCD. Briefly, the compounding was performed by weighing and dissolving HPBCD in sterile HPLC grade water. Then, Compound 2 was weighed and added to the HPBCD solution in an appropriate container. To enhance dissolution, sonication and magnetic stirring were alternated to obtain a clear solution. Then, the solution was dispensed into PET amber bottles, appropriately labeled and stored under refrigeration until dosing.

A pilot stability study was performed on a 0.7 mg/ml Compound 2 oral solution at three temperatures: −20° C., 4°

C., and room temperature (RT). Potency was maintained over a minimum period of three months at all storage conditions.

Samples were also subjected to three freeze-thaw cycles (−20° C. to room temperature). Solutions were evaluated for clarity. No precipitation was observed, and all solutions maintained clarity after the freeze-thaw cycles. The potency of these solutions was also determined using an LC/MS assay. Potency was maintained after 3-month storage and several freeze-thaw cycles between −80° C. and room temperature, indicating the stability of this formulation.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound of the following structural formula:

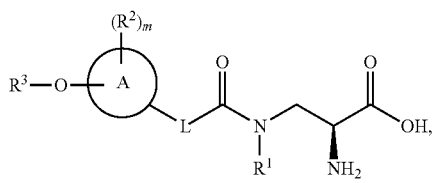

(I)

or a pharmaceutically acceptable salt of the foregoing, wherein:

Ring A is phenyl or $(C_5-C_6)$heteroaryl;
L is $-(CH_2)_n-$, $-C(O)-$ or $-C(OH)_2-$;
$R^1$ is H or $(C_1-C_5)$alkyl;
each $R^2$ is independently chloro or fluoro;
$R^3$ is $(C_1-C_3)$alkyl substituted with one or more independently selected $(C_6-C_{15})$aryl or $(C_5-C_{15})$heteroaryl, wherein the $(C_6-C_{15})$aryl and $(C_5-C_{15})$heteroaryl are each independently substituted with $-(R^{30})_p$;
each $R^{30}$ is independently halo, $(C_1-C_5)$alkoxy, $(C_1-C_5)$haloalkoxy, $(C_1-C_5)$alkyl or $(C_1-C_5)$haloalkyl, or two $R^{30}$ attached to adjacent ring atoms, taken together, form $-(CH_2)_q-$ or $-O(CH_2)_rO-$;
n is 1, 2 or 3;
m is 0, 1, 2, 3 or 4;
each p is independently 0, 1, 2, 3, 4, 5, 6, 7, 8, 9 or 10;
each q is independently 3, 4, 5 or 6; and
each r is independently 1, 2, 3 or 4.

2. The compound of claim 1, of the following structural formula:

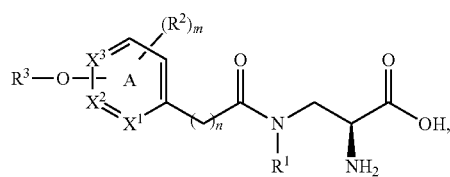

(II)

or a pharmaceutically acceptable salt thereof, wherein:
$X^1$, $X^2$ and $X^3$ are each >C(H);
$X^1$ is N, and $X^2$ and $X^3$ are each >C(H);

$X^1$ and $X^2$ are each >C(H), and $X^3$ is N; or
$X^1$ and $X^3$ are each >C(H), and $X^2$ is N.

3. The compound of claim 2, wherein $X^1$, $X^2$ and $X^3$ are each >C(H).

4. The compound of claim 2, wherein $X^1$ is N, and $X^2$ and $X^3$ are each >C(H).

5. The compound of claim 2, wherein the $-OR^3$ is attached to the ring atom of Ring A which is meta or para to $-(CH_2)_n-$.

6. The compound of claim 2, wherein $R^1$ is H.

7. The compound of claim 2, wherein $R^3$ is methyl substituted with one or two independently selected $(C_6-C_{15})$aryl or $(C_5-C_{15})$heteroaryl, each independently substituted with $-(R^{30})_p$.

8. The compound of claim 2, wherein $R^3$ is methyl substituted with one or two independently selected $(C_0-C_{15})$aryl or $(C_5-C_{15})$heteroaryl independently selected from phenyl, naphthyl, pyridinyl, quinolinyl, isoquinolinyl or benzo[d]imidazolyl, each independently substituted with $-(R^{30})_p$.

9. The compound of claim 2, wherein n is 1.

10. The compound of claim 2, wherein m is 0.

11. The compound of claim 2, wherein each p is independently 0, 1 or 2.

12. The compound of claim 2, wherein each q is independently 3 or 4, and each r is independently 1 or 2.

13. A compound of any of the following structural formulas:

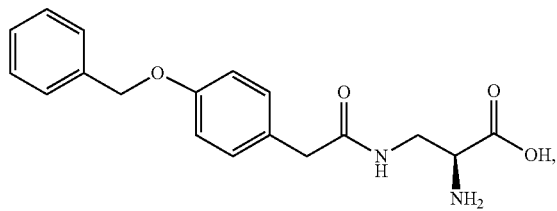

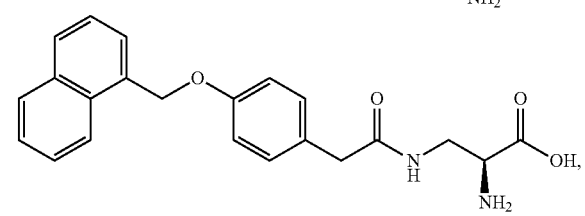

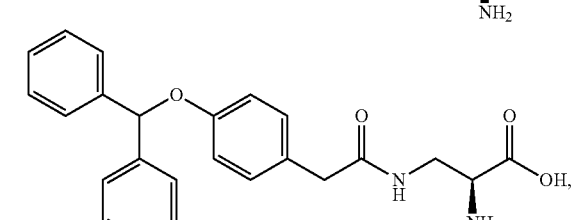

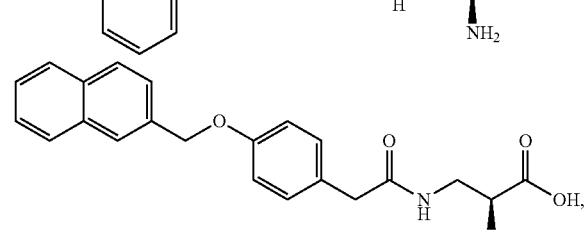

-continued

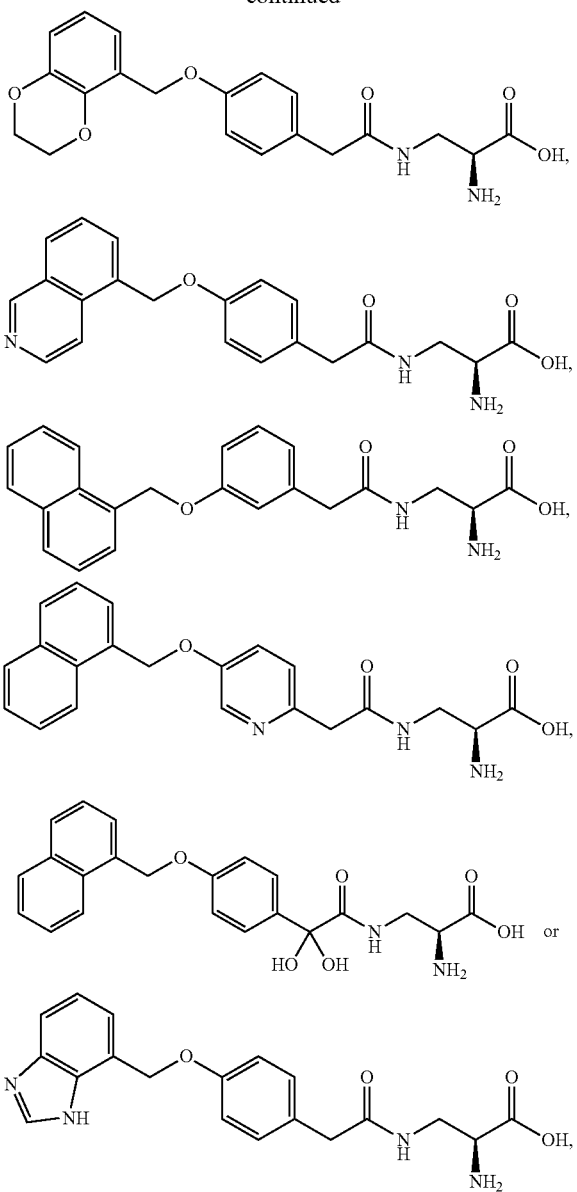

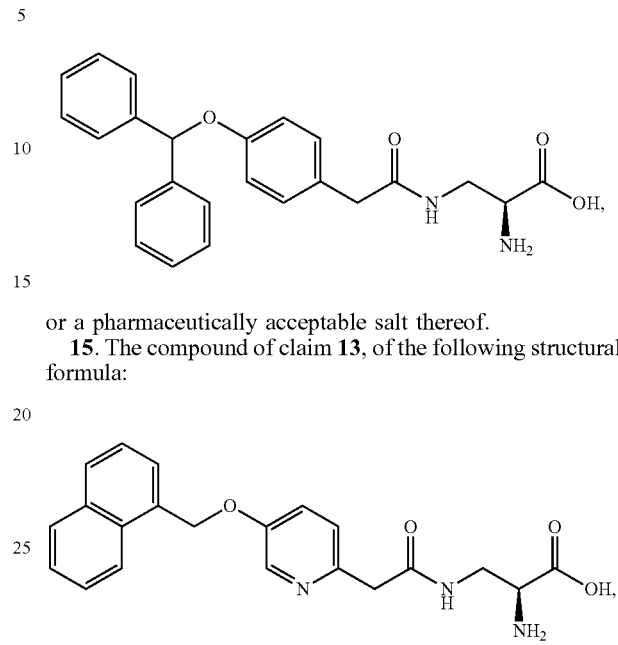

or a pharmaceutically acceptable salt of any of the foregoing.

14. The compound of claim 13, of the following structural formula:

or a pharmaceutically acceptable salt thereof.

15. The compound of claim 13, of the following structural formula:

or a pharmaceutically acceptable salt thereof.

16. A composition comprising a compound of claim 1, or a pharmaceutically acceptable salt thereof, and a pharmaceutically acceptable carrier.

17. The composition of claim 16, formulated for oral administration.

18. A combination comprising a compound of claim 1, or a pharmaceutically acceptable salt thereof, and an additional therapeutic agent.

19. A composition comprising a compound of claim 2, or a pharmaceutically acceptable salt thereof, and a pharmaceutically acceptable carrier.

20. The composition of claim 19, formulated for oral administration.

21. A combination comprising a compound of claim 2, or a pharmaceutically acceptable salt thereof, and an additional therapeutic agent.

* * * * *

UNITED STATES PATENT AND TRADEMARK OFFICE
CERTIFICATE OF CORRECTION

| | |
|---|---|
| PATENT NO. | : 12,016,836 B2 |
| APPLICATION NO. | : 18/168128 |
| DATED | : June 25, 2024 |
| INVENTOR(S) | : Anas Fathallah, Scott D. Larsen and Abdulraouf Ramadan |

It is certified that error appears in the above-identified patent and that said Letters Patent is hereby corrected as shown below:

In the Claims

Column 70, Claim 8, Line 19, "substituted with one or two independently selected $(C_0-C_{15})$" should be -- substituted with one or two independently selected $(C_6-C_{15})$ --

Signed and Sealed this
Seventh Day of January, 2025

Derrick Brent
*Acting Director of the United States Patent and Trademark Office*